United States Patent
Blankenstein et al.

(10) Patent No.: US 10,377,808 B2
(45) Date of Patent: Aug. 13, 2019

(54) HIGH AVIDITY ANTIGEN RECOGNIZING CONSTRUCTS

(71) Applicant: Max-Delbrück-Centrum für moledulare Medizin (MDC) Berlin-Buch, Berlin (DE)

(72) Inventors: Thomas Blankenstein, Berlin (DE); Matthias Obenaus, Berlin (DE); Catarina Leitão, Lisbon (PT)

(73) Assignee: Max-Delbrück-Centrum Für Molekulare Medizin (MDC) Berlin-Buch, Berlin (DE)

( * ) Notice: Subject to any disclaimer, the term of this patent is extended or adjusted under 35 U.S.C. 154(b) by 0 days.

(21) Appl. No.: 14/763,421

(22) PCT Filed: Jan. 29, 2014

(86) PCT No.: PCT/EP2014/051726
§ 371 (c)(1),
(2) Date: Jul. 24, 2015

(87) PCT Pub. No.: WO2014/118236
PCT Pub. Date: Aug. 7, 2014

(65) Prior Publication Data
US 2015/0353622 A1 Dec. 10, 2015

(30) Foreign Application Priority Data
Jan. 29, 2013 (EP) ..................................... 13153081

(51) Int. Cl.
| | | |
|---|---|---|
| *C07K 14/725* | (2006.01) | |
| *G01N 33/574* | (2006.01) | |
| *C07K 16/28* | (2006.01) | |
| *C07K 14/705* | (2006.01) | |
| *C07K 16/30* | (2006.01) | |

(52) U.S. Cl.
CPC .... *C07K 14/7051* (2013.01); *C07K 14/70503* (2013.01); *C07K 16/2803* (2013.01); *C07K 16/30* (2013.01); *G01N 33/57484* (2013.01); *C07K 2317/565* (2013.01); *C07K 2317/76* (2013.01); *G01N 2333/705* (2013.01)

(58) Field of Classification Search
None
See application file for complete search history.

(56) References Cited

U.S. PATENT DOCUMENTS 8,519,100 B2 * 8/2013 Jakobsen ........... C07K 14/7051
530/350
2009/0304679 A1 12/2009 Weidanz

FOREIGN PATENT DOCUMENTS

WO 9523164 A1 8/1995

OTHER PUBLICATIONS

Janeway et al., Immunobiology, 5th Ed., Garland Science, 2001, pp. 106-108, 117-118 and 260-263.*
Manning et al., Immunity, 1998, 8:413-425.*
Garcia et al., Cell, 2005, 122: 333-336.*
Goyarts et al., Molecular Immunology, 1998, 35:593-607.*
Kessels et al., Proceeding of the National Academy Science, 2000, 97:14578-83.*
Naklefski et al. (Journal of Experimental Medicine, 1992, 175:1553-1563).*
Venturi et al. (Journal of Immunology, 2011, 186:4285-4294).*
Deng et al. (PNAS, 2012, 109:14960-14965).*
Chames, Patrick et al., "Direct selection of a human antibody fragment directed against the tumor T-cell epitope HLA-A1-MAGE-A1 from a nonimmunized phage-Fab library," *PNAS*, Jul. 5, 2000, 97(14):7969-7974.
Database Geneseq, "Human T-cell receptor beta-chain protein," *XP002712966*, retrieved from EBI accession No. GSP:AFS46936, Jun. 14, 2007.
Database Geneseq, "HIV Gag TCR alpha chain (optimized for expression in human T cells)," *XP002699806*, retrieved from EBI accession No. GSP:AEK68686, Nov. 30, 2006.
Engels, Boris et al., "Redirecting Human T Lymphocytes Toward Renal Cell Carcinoma Specificity by Retroviral Transfer of T Cell Receptor Genes," *Human Gene Therapy*, Jul. 2005, 16:799-810.
Matkovic, Bozica et al., "Expression of MAGE-A and NY-ESO-1 cancer/testis antigens in medullary breast cancer: retrospective immunohistochemical study," *Croatian Medical Journal*, 2011, 52(2):171-177.
Orentas, Rimas J. et al., "Retroviral Transduction of a T Cell Receptor Specific for an Epstein-Barr Virus-Encoded Peptide," *Clinical Immunology*, Feb. 2001, 98(2):220-228.
Ottaviani, Sabrina et al., "A MAGE-1 antigenic peptide recognized by human cytolytic T lymphocytes on HLA-A2 tumor cells," *Cancer Immunology: Immunotherapy: CII*, 2005, 54(12):1214-1220.
Sommermeyer, Daniel et al., "Designer T cells by T cell receptor replacement," *Eur. J. Immunol.*, 2006, 36:3052-3059.

(Continued)

*Primary Examiner* — Julie Wu
(74) *Attorney, Agent, or Firm* — Saliwanchik, Lloyd & Eisenschenk

(57) ABSTRACT

The present invention pertains to novel high avidity antigen recognizing constructs, such as antibodies or T cell receptors, which specifically bind to the melanoma associated antigen (MAGE) A1. The constructs of the invention are particularly useful for the diagnosis, prevention or therapy of tumorous diseases which are characterized by the specific expression of the MAGE-A1 antigen. Furthermore provided are nucleic acids, vectors and host cells—such as CD4 or CD8 positive T cells—which encode, comprise or present the antigen recognizing constructs of the invention. The invention thus provides new means for immune therapy, specifically adoptive T cell therapy, for treating cancer.

8 Claims, 16 Drawing Sheets

Specification includes a Sequence Listing.

(56) References Cited

OTHER PUBLICATIONS

Sharma, P., Kranz, D.M., "Subtle changes at the variable domain interface of the T-cell receptor can strongly increase affinity." Journal of Biological Chemistry, Dec. 2017, 293(5): 1820-1834.
Li, Liang-Ping, et al., "Transgenic mice with a diverse human T cell antigen receptor repertoire." Nature Medicine, Sep. 2010, 16(9): 1029-1034.

* cited by examiner

SEQUENCE LISTING

```
<160> NUMBER OF SEQ ID NOS: 55

<210> SEQ ID NO 1
<211> LENGTH: 15
<212> TYPE: PRT
<213> ORGANISM: Artificial
<220> FEATURE:
<223> OTHER INFORMATION: CDR3

<400> SEQUENCE: 1

Cys Ala Glu Ser Ile Gly Ser Asn Ser Gly Tyr Ala Leu Asn Phe
1               5                   10                  15

<210> SEQ ID NO 2
<211> LENGTH: 14
<212> TYPE: PRT
<213> ORGANISM: artificial
<220> FEATURE:
<223> OTHER INFORMATION: CDR3

<400> SEQUENCE: 2

Cys Ala Ala Arg Pro Asn Ser Gly Asn Thr Pro Leu Val Phe
1               5                   10

<210> SEQ ID NO 3
<211> LENGTH: 12
<212> TYPE: PRT
```

```
<213> ORGANISM: Artificial
<220> FEATURE:
<223> OTHER INFORMATION: CDR3

<400> SEQUENCE: 3

Cys Ala Met Ser Asp Thr Gly Asn Gln Phe Tyr Phe
1               5                   10

<210> SEQ ID NO 4
<211> LENGTH: 13
<212> TYPE: PRT
<213> ORGANISM: Artificial
<220> FEATURE:
<223> OTHER INFORMATION: CDR3

<400> SEQUENCE: 4

Cys Ala Ser Arg Gly Leu Ala Gly Tyr Glu Gln Tyr Phe
1               5                   10

<210> SEQ ID NO 5
<211> LENGTH: 14
<212> TYPE: PRT
<213> ORGANISM: Artificial
<220> FEATURE:
<223> OTHER INFORMATION: CDR3

<400> SEQUENCE: 5

Cys Ser Val Glu Gln Asp Thr Asn Thr Gly Glu Leu Phe Phe
1               5                   10

<210> SEQ ID NO 6
<211> LENGTH: 15
<212> TYPE: PRT
<213> ORGANISM: Artificial
<220> FEATURE:
<223> OTHER INFORMATION: CDR3

<400> SEQUENCE: 6

Cys Ala Ser Ser Phe Arg Gly Gly Gly Ala Asn Val Leu Thr Phe
1               5                   10                  15

<210> SEQ ID NO 7
<211> LENGTH: 11
<212> TYPE: PRT
<213> ORGANISM: Homo sapiens

<400> SEQUENCE: 7

Cys Ala Glu Ser Tyr Asn Ala Arg Leu Met Phe
1               5                   10

<210> SEQ ID NO 8
<211> LENGTH: 13
<212> TYPE: PRT
<213> ORGANISM: Homo sapiens

<400> SEQUENCE: 8

Cys Ala Gly Ser Gly Gly Gly Thr Asp Lys Leu Ile Phe
1               5                   10

<210> SEQ ID NO 9
<211> LENGTH: 16
<212> TYPE: PRT
<213> ORGANISM: Homo sapiens

<400> SEQUENCE: 9

Cys Ser Ala Arg Glu Pro Gly Gln Gly Pro Tyr Glu Gln Tyr Phe Gly
```

<210> SEQ ID NO 10
<211> LENGTH: 11
<212> TYPE: PRT
<213> ORGANISM: Homo sapiens

<400> SEQUENCE: 10

Cys Ala Ser Leu Ser Gly Val Tyr Thr Phe Gly
1               5                   10

<210> SEQ ID NO 11
<211> LENGTH: 9
<212> TYPE: PRT
<213> ORGANISM: Homo sapiens

<400> SEQUENCE: 11

Lys Val Leu Glu Tyr Val Ile Lys Val
1               5

<210> SEQ ID NO 12
<211> LENGTH: 9
<212> TYPE: PRT
<213> ORGANISM: Mus musculus

<400> SEQUENCE: 12

Lys Val Leu Gln Phe Phe Ala Ser Ile
1               5

<210> SEQ ID NO 13
<211> LENGTH: 7278
<212> TYPE: DNA
<213> ORGANISM: artificial
<220> FEATURE:
<223> OTHER INFORMATION: pMP71-TCR1367hc

<400> SEQUENCE: 13

| | |
|---|---|
| tcaaggttag gaacagagag acagcagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgataga ctgcgtcgcc cgggtacccg tattcccaat aaagcctctt gctgtttgca | 420 |
| tccgaatcgt ggactcgctg atccttggga gggtctcctc agattgattg actgcccacc | 480 |
| tcgggggtct ttcatttgga ggttccaccg agatttggag accctgccc agggaccacc | 540 |
| gacccccccg ccgggaggta agctggccag cggtcgtttc gtgtctgtct ctgtctttgt | 600 |
| gcgtgtttgt gccggcatct aatgtttgcg cctgcgtctg tactagttgg ctaactagat | 660 |
| ctgtatctgg cggtcccgcg gaagaactga cgagttcgta ttcccggccg cagcccctgg | 720 |
| gagacgtccc agcggcctcg ggggcccgtt ttgtggccca ttctgtatca gttaacctac | 780 |
| ccgagtcgga cttttggag ctccgccact gtccgagggg tacgtggctt tgttggggga | 840 |
| cgagagacag agacacttcc cgccccgtc tgaattttg ctttcggttt tacgccgaaa | 900 |
| ccgcgccgcg cgtcttgtct gctgcagcat cgttctgtgt tgtctctgtc tgactgtgtt | 960 |
| tctgtatttg tctgaaaatt agctcgacaa agttaagtaa tagtccctct ctccaagctc | 1020 |

```
acttacaggc ggccgccacc atgggaatca gactgctgtg cagagtggcc ttctgcttcc   1080
tggccgtggg cctggtggac gtgaaagtga cccagagcag cagatacctc gtgaagcgga   1140
ccggcgagaa ggtgttcctg gaatgcgtgc aggacatgga ccacgagaat atgttctggt   1200
acagacagga ccccggcctg ggcctgcggc tgatctactt cagctacgac gtgaagatga   1260
aggaaaaggg cgacatcccc gagggctaca gcgtgtccag agagaagaaa gagcggttca   1320
gcctgatcct ggaaagcgcc agcaccaacc agaccagcat gtacctgtgc gccagcagag   1380
gcctggccgg ctacgagcag tattttggcc ctggcacccg gctgaccgtg accgaggacc   1440
tgaagaacgt gttccccccc gaggtggccg tgttcgagcc cagcgaggcc gagatcagcc   1500
acacccagaa agccaccctg gtgtgcctgg ccaccggctt ctaccccgac cacgtggagc   1560
tgtcttggtg ggtgaacggc aaagaggtgc acagcggcgt cagcaccgac ccccagcccc   1620
tgaaagagca gcccgccctg aacgacagcc ggtactgcct gagcagccgg ctgagagtga   1680
gcgccacctt ctggcagaac ccccggaacc acttccggtg ccaggtgcag ttctacggcc   1740
tgagcgagaa cgacgagtgg acccaggaca gagccaagcc cgtgacccag atcgtgagcg   1800
ccgaggcctg gggcagagcc gactgcggct tcaccagcga gagctaccag cagggcgtgc   1860
tgtccgccac aatcctgtac gagatcctgc tgggcaaggc cacctgtac gccgtgctgg   1920 tgtccgccct ggtgctgatg gccatggtga gcggaagga cagccggggc ggcagcggcg   1980
ccaccaactt tagcctgctg aaacaggccg gcgacgtgga agagaaccct ggccccatga   2040
agaccttcgc cggcttcagc ttcctgttcc tgtggctgca gctggactgc atgagcaggg   2100
gcgaggacgt ggaacagagc ctgtttctga gcgtgcgcga gggcgacagc agcgtgatca   2160
attgcaccta caccgacagc tccagcacct acctgtactg gtacaagcag gaacctggcg   2220
ccggactgca gctgctgacc tacatcttca gcaacatgga catgaagcag gaccagagac   2280
tgaccgtgct gctgaacaag aaggacaagc acctgagcct gcggatcgcc gatacccaga   2340
caggcgacag cgccatctac ttttgcgccg agagcatcgg cagcaacagc ggctacgccc   2400
tgaacttcgg caagggcaca agcctgctcg tgaccccctc catccagaac cccgaccccg   2460
ccgtgtacca gctgcgggac agcaagagca gcgacaagag cgtgtgcctg ttcaccgact   2520
tcgacagcca gaccaacgtg agccagagca aggactccga cgtgtacatc accgacaaga   2580
ccgtgctgga catgcggagc atggacttca gagcaactc cgccgtggcc tggtccaaca   2640
agagcgactt cgcctgcgcc aacgccttca caacagcat catccccgag gacacctttt   2700
tccccagccc cgagagcagc tgcgacgtga actggtggga aagagcttc gagaccgaca   2760 ccaacctgaa cttccagaac ctgtccgtga tcggcttccg gatcctgctg ctgaaggtgg   2820
ccggcttcaa cctgctgatg acactgcggc tgtggagcag ctgaattcga gcatcttacc   2880
gccatttatt cccatatttg ttctgttttt cttgatttgg gtatacattt aaatgttaat   2940
aaaacaaaat ggtggggcaa tcatttacat tttatgggat atgtaattac tagttcaggt   3000
gtattgccac aagacaaaca tgttaagaaa ctttcccgtt atttacgctc tgttcctgtt   3060
aatcaacctc tggattacaa aatttgtgaa agattgactg atattcttaa ctatgttgct   3120
ccttttacgc tgtgtggata tgctgcttta atgcctctgt atcatgctat tgcttcccgt   3180
acggctttcg ttttctcctc cttgtataaa tcctggttgc tgtctcttta tgaggagttg   3240
tggcccgttg tccgtcaacg tggcgtggtg tgctctgtgt ttgctgacgc aacccccact   3300 ggctgggca ttgccaccac ctgtcaactc ctttctggga ctttcgcttt cccctcccg   3360 atcgccacgg cagaactcat cgccgcctgc cttgcccgct gctggacagg ggctaggttg   3420
```

```
ctgggcactg ataattccgt ggtgttgtcg gggaagctga cgtcctttcc atggctgctc    3480
gcctgtgttg ccaactggat cctgcgcggg acgtccttct gctacgtccc ttcggctctc    3540
aatccagcgg acctcccttc ccgaggcctt ctgccggttc tgcggcctct cccgcgtctt    3600
cgctttcggc ctccgacgag tcggatctcc ctttgggccg cctccccgcc tgtttcgcct    3660
cggcgtccgg tccgtgttgc ttggtcgtca cctgtgcaga attgcgaacc atggattcca    3720
ccgtgaactt tgtctcctgg catgcaaatc gtcaacttgg catgccaaga attaattcgg    3780
atccaagctt aggcctgctc gctttcttgc tgtcccattt ctattaaagg ttcctttgtt    3840
ccctaagtcc aactactaaa ctgggggata ttatgaaggg ccttgagcat ctggattctg    3900
cctagcgcta agcttaacac gagccataga tagaataaaa gattttattt agtctccaga    3960
aaaagggggg aatgaaagac cccacctgta ggtttggcaa gctagcttaa gtaacgccat    4020
tttgcaaggc atggaaaata cataactgag aatagagaag ttcagatcaa ggttaggaac    4080
agagagacag cagaatatgg gccaaacagg atatctgtgg taagcagttc ctgccccggc    4140
tcagggccaa gaacagttgg aacagcagaa tatgggccaa acaggatatc tgtggtaagc    4200
agttcctgcc ccggctcagg gccaagaaca gatggtcccc agatgcggtc ccgccctcag    4260
cagtttctag agaaccatca gatgtttcca gggtgcccca aggacctgaa atgaccctgt    4320
gccttatttg aactaaccaa tcagttcgct tctcgcttct gttcgcgcgc ttctgctccc    4380
cgagctcaat aaaagagccc acaaccctc actcggcgcg ccagtcctcc gatagactgc    4440
gtcgcccggg tacccgtgtt ctcaataaac cctcttgcag ttgcatccga ctcgtggtct    4500
cgctgttcct tgggagggtc tcctctgagt gattgactgc ccacctcggg ggtctttcat    4560
tctcgagcag cttggcgtaa tcatggtcat agctgtttcc tgtgtgaaat tgttatccgc    4620
tcacaattcc acacaacata cgagccggaa gcataaagtg taaagcctgg ggtgcctaat    4680
gagtgagcta actcacatta attgcgttgc gctcactgcc cgctttccag tcgggaaacc    4740
tgtcgtgcca gctgcattaa tgaatcggcc aacgcgcggg gagaggcggt ttgcgtattg    4800
ggcgctcttc cgcttcctcg ctcactgact cgctgcgctc ggtcgttcgg ctgcggcgag    4860
cggtatcagc tcactcaaag gcggtaatac ggttatccac agaatcaggg gataacgcag    4920
gaaagaacat gtgagcaaaa ggccagcaaa aggccaggaa ccgtaaaaag gccgcgttgc    4980
tggcgttttt ccataggctc cgcccccctg acgagcatca caaaaatcga cgctcaagtc    5040
agaggtggcg aaacccgaca ggactataaa gataccaggc gtttccccct ggaagctccc    5100
tcgtgcgctc tcctgttccg accctgccgc ttaccggata cctgtccgcc tttctccctt    5160
cgggaagcgt ggcgctttct catagctcac gctgtaggta tctcagttcg gtgtaggtcg    5220
ttcgctccaa gctgggctgt gtgcacgaac cccccgttca gcccgaccgc tgcgccttat    5280
ccggtaacta tcgtcttgag tccaacccgg taagacacga cttatcgcca ctggcagcag    5340
ccactggtaa caggattagc agagcgaggt atgtaggcgg tgctacagag ttcttgaagt    5400
ggtggcctaa ctacggctac actagaagaa cagtatttgg tatctgcgct ctgctgaagc    5460
cagttacctt cggaaaaaga gttggtagct cttgatccgg caaacaaacc accgctggta    5520
gcggtggttt ttttgtttgc aagcagcaga ttacgcgcag aaaaaaagga tctcaagaag    5580
atcctttgat cttttctacg gggtctgacg ctcagtggaa cgaaaactca cgttaaggga    5640
ttttggtcat gagattatca aaaaggatct tcacctagat ccttttaaat taaaaatgaa    5700
gttttaaatc aatctaaagt atatatgagt aaacttggtc tgacagttac caatgcttaa    5760
```

```
tcagtgaggc acctatctca gcgatctgtc tatttcgttc atccatagtt gcctgactcc    5820
ccgtcgtgta gataactacg atacgggagg gcttaccatc tggccccagt gctgcaatga    5880
taccgcgaga cccacgctca ccggctccag atttatcagc aataaaccag ccagccggaa    5940
gggccgagcg cagaagtggt cctgcaactt tatccgcctc catccagtct attaattgtt    6000
gccgggaagc tagagtaagt agttcgccag ttaatagttt gcgcaacgtt gttgccattg    6060
ctacaggcat cgtggtgtca cgctcgtcgt ttggtatggc ttcattcagc tccggttccc    6120
aacgatcaag gcgagttaca tgatccccca tgttgtgcaa aaaagcggtt agctccttcg    6180
gtcctccgat cgttgtcaga agtaagttgg ccgcagtgtt atcactcatg gttatggcag    6240
cactgcataa ttctcttact gtcatgccat ccgtaagatg cttttctgtg actggtgagt    6300
actcaaccaa gtcattctga aatagtgta tgcggcgacc gagttgctct tgcccggcgt     6360
caatacggga taataccgcg ccacatagca gaactttaaa agtgctcatc attggaaaac    6420
gttcttcggg gcgaaaactc tcaaggatct taccgctgtt gagatccagt tcgatgtaac    6480
ccactcgtgc acccaactga tcttcagcat cttttacttt caccagcgtt tctgggtgag    6540
caaaaacagg aaggcaaaat gccgcaaaaa agggaataag ggcgacacgg aaatgttgaa    6600
tactcatact cttcctttt caatattatt gaagcattta tcagggttat tgtctcatga    6660
gcggatacat atttgaatgt atttagaaaa ataaacaaat aggggttccg cgcacatttc    6720
cccgaaaagt gccacctgac gtctaagaaa ccattattat catgacatta acctataaaa    6780
ataggcgtat cacgaggccc tttcgtctcg cgcgtttcgg tgatgacggt gaaaacctct    6840
gacacatgca gctcccggag acggtcacag cttgtctgta gcggatgcc gggagcagac     6900
aagcccgtca gggcgcgtca gcgggtgttg gcgggtgtcg ggctggctt aactatgcgg      6960
catcagagca gattgtactg agagtgcacc atatgcggtg tgaaataccg cacagatgcg    7020
taaggagaaa ataccgcatc aggcgccatt cgccattcag gctgcgcaac tgttgggaag    7080
ggcgatcggt gcgggcctct tcgctattac gccagctggc gaaagggga gtgtgctgcaa    7140
ggcgattaag ttgggtaacg ccagggtttt cccagtcacg acgttgtaaa acgacggcca    7200
gtgaattagt actctagctt aagtaacgcc attttgcaag gcatggaaaa tacataactg    7260
agaatagaga agttcaga                                                   7278
```

<210> SEQ ID NO 14
<211> LENGTH: 7248
<212> TYPE: DNA
<213> ORGANISM: Artificial
<220> FEATURE:
<223> OTHER INFORMATION: pMP71_1367_mc

<400> SEQUENCE: 14

```
tcaaggttag gaacagagag acagcagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgataga ctgcgtcgcc cgggtacccg tattcccaat aaagcctctt gctgtttgca     420
tccgaatcgt ggactcgctg atccttggga gggtctcctc agattgattg actgcccacc     480
tcggggggtct ttcatttgga ggttccaccg agatttggag acccctgccc agggaccacc     540
```

```
gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttggag ctccgccact gtccgagggg tacgtggctt tgttgggga     840
cgagagacag agacacttcc cgcccccgtc tgaattttg ctttcggttt tacgccgaaa     900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atgggaatca gactgctgtg cagagtggcc ttctgcttcc   1080
tggccgtggg cctggtggac gtgaaagtga cccagagcag cagataccte gtgaagcgga   1140
ccggcgagaa ggtgttcctg gaatgcgtgc aggacatgga ccacgagaat atgttctggt   1200
acagacagga ccccggcctg gcctgcggc tgatctactt cagctacgac gtgaagatga   1260
aggaaaaggg cgacatcccc gagggctaca gcgtgtccag agagaagaaa gagcggttca   1320
gcctgatcct ggaaagcgcc agcaccaacc agaccagcat gtacctgtgc gccagcagag   1380
gcctggccgg ctacgagcag tattttggcc ctggcacccg gctgaccgtg accgaggatc   1440
tgagaaacgt gaccccccccc aaggtgtccc tgttcgagcc tagcaaggcc gagatcgcca   1500
acaaacagaa agccaccctc gtgtgcctgg ccagaggctt cttccccgac cacgtggaac   1560
tgtcttggtg ggtcaacggc aaagaggtgc acagcggcgt gtccaccgat ccccaggcct   1620
acaaagagag caactacagc tactgcctga gcagcaggct gcgggtgtcc gccaccttct   1680
ggcacaaccc ccggaaccac ttcagatgcc aggtgcagtt tcacggcctg agcgaagagg   1740
acaagtggcc cgagggaagc cccaagcccg tgacacagaa tatcagcgcc gaagcctggg   1800
gcagagccga ctgtggaatc accagcgcca gctatcacca gggcgtgctg agcgccacaa   1860
tcctgtacga gatcctgctg ggcaaggcca ccctgtacgc cgtgctggtg tctggcctgg   1920
tgctgatggc catggtcaag aagaagaaca gcggcagcgg cgccaccaac tttagcctgc   1980
tgaaacaggc cggcgacgtg gaagagaacc ctggcccat gaagaccttc gccggcttca   2040
gcttcctgtt cctgtggctg cagctggact gcatgagcag gggcgaggac gtggaacaga   2100
gcctgttct gagcgtgcgc gagggcgaca gcagcgtgat caattgcacc tacaccgaca   2160
gctccagcac ctacctgtac tggtacaagc aggaacctgg cgccggactg cagctgctga   2220
cctacatctt cagcaacatg gacatgaagc aggaccagag actgaccgtg ctgctgaaca   2280
agaaggacaa gcacctgagc ctgcggatcg ccgatccca gacaggcgac agcgccatct   2340
actttgcgc cgagagcatc ggcagcaaca cgggctacgc cctgaacttc ggcaagggca   2400
caagcctgct cgtgacccct cacatccaga accctgagcc agccgtgtac cagctgaagg   2460
acccagaag ccaggacagc accctgtgcc tgttcaccga cttcgacagc cagatcaacg   2520
tgcccaagac catggaaagc ggcacctca tcaccgacaa gacagtgctg gatatgaagg   2580
ccatggacag caagagcaac ggcgccattg cctggtccaa tcagacaagc ttcacatgcc   2640
aggacatctt caaagagaca aacgccacct acccccagcg cgacgtgccc tgtgatgcca   2700
ccctgaccga gaagtccttc gagacagaca tgaacctgaa tttccagaac ctgtccgtga   2760
tgggcctgag aatcctgctg ctgaaggtgg ccggcttcaa cctgctgatg accctgagac   2820
tgtggtccag ctgaattcga gcatcttacc gccatttatt cccatatttg ttctgttttt   2880
```

-continued

```
cttgatttgg gtatacattt aaatgttaat aaaacaaaat ggtggggcaa tcatttacat    2940
tttatgggat atgtaattac tagttcaggt gtattgccac aagacaaaca tgttaagaaa    3000 cttttcccgtt atttacgctc tgttcctgtt aatcaacctc tggattacaa aatttgtgaa    3060
agattgactg atattcttaa ctatgttgct ccttttacgc tgtgtggata tgctgcttta    3120
atgcctctgt atcatgctat tgcttcccgt acggctttcg ttttctcctc cttgtataaa    3180
tcctggttgc tgtctctta tgaggagttg tggcccgttg tccgtcaacg tggcgtggtg    3240
tgctctgtgt ttgctgacgc aaccccact ggctgggca ttgccaccac ctgtcaactc    3300
cttctctgga ctttcgcttt cccctcccg atcgccacgg cagaactcat cgccgcctgc    3360
cttgcccgct gctggacagg ggctaggttg ctgggcactg ataattccgt ggtgttgtcg    3420
gggaagctga cgtcctttcc atggctgctc gcctgtgttg ccaactggat cctgcgcggg    3480
acgtccttct gctacgtccc ttcggctctc aatccagcgg acctcccttc ccgaggcctt    3540
ctgccggttc tgcggcctct cccgcgtctt cgctttcggc ctccgacgag tcggatctcc    3600
ctttgggccg cctccccgcc tgtttcgcct cggcgtccgg tccgtgttgc ttggtcgtca    3660
cctgtgcaga attgcgaacc atggattcca ccgtgaactt tgtctcctgg catgcaaatc    3720
gtcaacttgg catgccaaga attaattcgg atccaagctt aggcctgctc gctttcttgc    3780
tgtcccattt ctattaaagg ttcctttgtt ccctaagtcc aactactaaa ctgggggata    3840
ttatgaaggg ccttgagcat ctggattctg cctagcgcta agcttaacac gagccataga    3900
tagaataaaa gattttattt agtctccaga aaagggggg aatgaaagac cccacctgta    3960
ggtttggcaa gctagcttaa gtaacgccat tttgcaaggc atgaaaaata caactgag    4020 aatagagaag ttcagatcaa ggttaggaac agagagacag cagaatatgg ccaaacagg    4080 atatctgtgg taagcagttc ctgccccggc tcagggccaa gaacagttgg aacagcagaa    4140
tatgggccaa acaggatatc tgtggtaagc agttcctgcc ccggtcagg gccaagaaca    4200 gatggtcccc agatgcggtc ccgccctcag cagtttctag agaaccatca gatgtttcca    4260
gggtgcccca aggacctgaa atgaccctgt gccttattg aactaaccaa tcagttcgct    4320
tctcgcttct gttcgcgcgc ttctgctccc cgagctcaat aaaagagccc acaacccctc    4380
actcggcgcg ccagtcctcc gatagactgc gtcgcccggg tacccgtgtt ctcaataaac    4440
cctcttgcag ttgcatccga tcgtggtct cgctgttcct tgggagggtc tcctctgagt    4500
gattgactgc ccacctcggg ggtctttcat tctcgagcag cttggcgtaa tcatggtcat    4560 agctgttttcc tgtgtgaaat tgttatccgc tcacaattcc acacaacata cgagccggaa    4620
gcataaagtg taaagcctgg ggtgcctaat gagtgagcta actcacatta attgcgttgc    4680
gctcactgcc cgctttccag tcgggaaacc tgtcgtgcca gctgcattaa tgaatcggcc    4740
aacgcgcggg gagaggcggt ttgcgtattg ggcgctcttc cgcttcctcg ctcactgact    4800
cgctgcgctc ggtcgttcgg ctgcggcgag cggtatcagc tcactcaaag gcggtaatac    4860
ggttatccac agaatcaggg gataacgcag gaaagaacat gtgagcaaaa ggccagcaaa    4920
aggccaggaa ccgtaaaaag gccgcgttgc tggcgttttt ccataggctc cgcccccctg    4980
acgagcatca caaaaatcga cgctcaagtc agaggtggcg aaacccgaca ggactataaa    5040
gataccaggc gtttccccct ggaagctccc tcgtgcgctc tcctgttccg accctgccgc    5100
ttaccggata cctgtccgcc tttctccctt cgggaagcgt ggcgctttct catagctcac    5160
gctgtaggta tctcagttcg gtgtaggtcg ttcgctccaa gctgggctgt gtgcacgaac    5220
cccccgttca gcccgaccgc tgcgccttat ccggtaacta tcgtcttgag tccaacccgg    5280
```

| | |
|---|---|
| taagacacga cttatcgcca ctggcagcag ccactggtaa caggattagc agagcgaggt | 5340 |
| atgtaggcgg tgctacagag ttcttgaagt ggtggcctaa ctacggctac actagaagaa | 5400 |
| cagtatttgg tatctgcgct ctgctgaagc cagttacctt cggaaaaaga gttggtagct | 5460 |
| cttgatccgg caaacaaacc accgctggta gcggtggttt ttttgtttgc aagcagcaga | 5520 |
| ttacgcgcag aaaaaaagga tctcaagaag atcctttgat cttttctacg ggtctgacg | 5580 |
| ctcagtggaa cgaaaactca cgttaaggga ttttggtcat gagattatca aaaggatct | 5640 |
| tcacctagat ccttttaaat taaaaatgaa gttttaaatc aatctaaagt atatatgagt | 5700 |
| aaacttggtc tgacagttac caatgcttaa tcagtgaggc acctatctca gcgatctgtc | 5760 |
| tatttcgttc atccatagtt gcctgactcc ccgtcgtgta gataactacg atacgggagg | 5820 |
| gcttaccatc tggccccagt gctgcaatga taccgcgaga cccacgctca ccggctccag | 5880 |
| atttatcagc aataaaccag ccagccggaa gggccgagcg cagaagtggt cctgcaactt | 5940 |
| tatccgcctc catccagtct attaattgtt gccgggaagc tagagtaagt agttcgccag | 6000 |
| ttaatagttt gcgcaacgtt gttgccattg ctacaggcat cgtggtgtca cgctcgtcgt | 6060 |
| ttggtatggc ttcattcagc tccggttccc aacgatcaag gcgagttaca tgatccccca | 6120 |
| tgttgtgcaa aaaagcggtt agctccttcg gtcctccgat cgttgtcaga agtaagttgg | 6180 |
| ccgcagtgtt atcactcatg gttatggcag cactgcataa ttctcttact gtcatgccat | 6240 |
| ccgtaagatg cttttctgtg actggtgagt actcaaccaa gtcattctga atagtgta | 6300 |
| tgcggcgacc gagttgctct tgcccggcgt caatacggga taataccgcg ccacatagca | 6360 |
| gaactttaaa agtgctcatc attggaaaac gttcttcggg gcgaaaactc tcaaggatct | 6420 |
| taccgctgtt gagatccagt tcgatgtaac ccactcgtgc acccaactga tcttcagcat | 6480 |
| cttttacttt caccagcgtt tctgggtgag caaaaacagg aaggcaaaat gccgcaaaaa | 6540 |
| agggaataag ggcgacacgg aaatgttgaa tactcatact cttcctttt caatattatt | 6600 |
| gaagcattta tcagggttat tgtctcatga gcggatacat atttgaatgt atttagaaaa | 6660 |
| ataaacaaat aggggttccg cgcacatttc cccgaaaagt gccacctgac gtctaagaaa | 6720 |
| ccattattat catgacatta acctataaaa ataggcgtat cacgaggccc tttcgtctcg | 6780 |
| cgcgtttcgg tgatgacggt gaaaacctct gacacatgca gctcccggag acggtcacag | 6840 |
| cttgtctgta agcggatgcc gggagcagac aagcccgtca gggcgcgtca gcgggtgttg | 6900 |
| gcgggtgtcg ggctggctt aactatgcgg catcagagca gattgtactg agagtgcacc | 6960 |
| atatgcggtg tgaaataccg cacagatgcg taaggagaaa ataccgcatc aggcgccatt | 7020 |
| cgccattcag gctgcgcaac tgttgggaag ggcgatcggt gcgggcctct tcgctattac | 7080 |
| gccagctggc gaaggggga tgtgctgcaa ggcgattaag ttgggtaacg ccagggtttt | 7140 |
| cccagtcacg acgttgtaaa acgacggcca gtgaattagt actctagctt aagtaacgcc | 7200 |
| attttgcaag gcatggaaaa tacataactg agaatagaga agttcaga | 7248 |

<210> SEQ ID NO 15
<211> LENGTH: 7278
<212> TYPE: DNA
<213> ORGANISM: artificial
<220> FEATURE:
<223> OTHER INFORMATION: pMP71-TCR1367mmc

<400> SEQUENCE: 15

| | |
|---|---|
| tcaaggttag gaacagagag acagcagaat atgggccaaa caggatatct gtggtaagca | 60 |

-continued

```
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc cccaaggacc    240
tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtctcctc agattgattg actgcccacc    480 tcggggtct  ttcatttgga ggttccaccg agatttggag accctgccc  agggaccacc    540 gaccccccg  ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttggag  ctccgccact gtccgagggg tacgtggctt tgttggggga    840
cgagagacag agacacttcc cgcccccgtc tgaattttg  ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atgggaatca gactgctgtg cagagtggcc ttctgcttcc   1080
tggccgtggg cctggtggac gtgaaagtga cccagagcag cagataccte gtgaagcgga   1140 ccggcgagaa ggtgttcctg gaatgcgtgc aggacatgga ccacgagaat atgttctggt   1200
acagacagga ccccggcctg ggcctgcggc tgatctactt cagctacgac gtgaagatga   1260
aggaaaaggg cgacatcccc gagggctaca gcgtgtccag agagaagaaa gagcggttca   1320
gcctgatcct ggaaagcgcc agcaccaacc agaccagcat gtacctgtgc gccagcagag   1380
gcctggccgc ctacgagcag tattttggcc ctggcacccg gctgaccgtg accgaggacc   1440
tgaagaacgt gttccccccc gaggtggccg tgttcgagcc cagcaaggcc gagatcgccc   1500
acacccagaa agccaccctg gtgtgcctgg ccaccggctt ctaccccgac cacgtggaac   1560
tgtcttggtg ggtgaacggc aaagaggtgc acagcggcgt gtgtaccgac ccccagcccc   1620
tgaaagagca gcctgccctg aacgactccc ggtactgcct gagcagccgg ctgagagtgt   1680
ccgccacctt ctggcagaac ccccggaacc acttcagatg ccaggtgcag ttctacggcc   1740
tgagcgagaa cgacgagtgg acccaggacc gggccaagcc cgtgacccag attgtgtctg   1800
ccgaggcctg gggcagagct gattgtggca tcaccagcgc cagctaccac cagggcgtgc   1860
tgagcgccac catcctgtac gagatcctgc tgggcaaggc caccctgtac gccgtgctgg   1920
tgtccgccct ggtgctgatg gccatggtga acggaagga  cagcagaggc ggcagcggcg   1980
ccaccaactt tagcctgctg aaacaggccg cgacgtgga  agagaaccct ggccccatga   2040
agaccttcgc cggcttcagc ttcctgttcc tgtggctgca gctggactgc atgagcaggg   2100
gcgaggacgt ggaacagagc ctgtttctga gcgtgcgcga gggcgacagc agcgtgatca   2160
attgcaccta caccgacagc tccagcacct acctgtactg gtacaagcag gaacctggcg   2220
ccggactgca gctgctgacc tacatcttca gcaacatgga catgaagcag gaccagagac   2280
tgaccgtgct gctgaacaag aaggacaagc acctgagcct gcggatcgcc gatacccaga   2340
caggcgacag cgccatctac tttgcgccg  agagcatcgg cagcaacagc ggctacgccc   2400
tgaacttcgg caagggcaca agcctgctcg tgaccccctca catccagaac cccgacccg   2460
```

-continued

```
ccgtgtacca gctgcgggac agcaagagca gcgacaagag cgtgtgcctg ttcaccgact   2520
tcgacagcca gaccaacgtg tcccagagca aggacagcga cgtgtacatc accgacaagt   2580
gcgtgctgga catgcggagc atggacttca agagcaactc cgccgtggcc tggtccaaca   2640
agagcgactt cgcctgcgcc aacgccttca acaacagcat catccccgag acacattct   2700 tccccagctc cgacgtgccc tgcgacgtga agctggtgga aaagagcttc gagacagaca   2760
ccaacctgaa cttccagaac ctgagcgtga tcggcttccg gatcctgctg ctgaaggtgg   2820
ctggcttcaa cctgctgatg accctgcggc tgtggagcag ctgaattcga gcatcttacc   2880
gccatttatt cccatatttg ttctgttttt cttgatttgg gtatacattt aaatgttaat   2940
aaaacaaaat ggtggggcaa tcatttacat tttatgggat atgtaattac tagttcaggt   3000
gtattgccac aagacaaaca tgttaagaaa ctttcccgtt atttacgctc tgttcctgtt   3060
aatcaacctc tggattacaa aatttgtgaa agattgactg atattcttaa ctatgttgct   3120
ccttttacgc tgtgtggata tgctgcttta atgcctctgt atcatgctat tgcttcccgt   3180
acggctttcg ttttctcctc cttgtataaa tcctggttgc tgtctcttta tgaggagttg   3240
tggcccgttg tccgtcaacg tggcgtggtg tgctctgtgt ttgctgacgc aaccccact   3300 ggctggggca ttgccaccac ctgtcaactc cttcctggga cttcgctttt cccctcccg   3360 atcgccacgg cagaactcat cgccgcctgc cttgcccgct gctggacagg gctaggttg   3420 ctgggcactg ataattccgt ggtgttgtcg gggaagctga cgtcctttcc atggctgctc   3480
gcctgtgttg ccaactggat cctgcgcggg acgtccttct gctacgtccc ttcggctctc   3540
aatccagcgg acctcccttc ccgaggcctt ctgccggttc tgcggcctct cccgcgtctt   3600
cgctttcggc ctcgacgagt cggatctcc ctttgggccg cctccccgcc tgtttcgcct   3660
cggcgtccgg tccgtgttgc ttggtcgtca cctgtgcaga attgcgaacc atggattcca   3720
ccgtgaactt tgtctcctgg catgcaaatc gtcaacttgg catgccaaga attaattcgg   3780
atccaagctt aggcctgctc gctttcttgc tgtcccattt ctattaaagg ttcctttgtt   3840
ccctaagtcc aactactaaa ctgggggata ttatgaaggg ccttgagcat ctggattctg   3900
cctagcgcta agcttaacac gagccataga tagaataaaa gattttattt agtctccaga   3960 aaaaggggg aatgaaagac cccacctgta ggtttggcaa gctagcttaa gtaacgccat   4020
tttgcaaggc atggaaaata cataactgag aatagaaag ttcagatcaa ggttaggaac   4080
agagagacag cagaatatgg gccaaacagg atatctgtgg taagcagttc ctgccccggc   4140
tcagggccaa gaacagttgg aacagcagaa tatgggccaa acaggatatc tgtggtaagc   4200
agttcctgcc ccggctcagg gccaagaaca gatggtcccc agatgcggtc cgccctcag   4260 cagtttctag agaaccatca gatgtttcca gggtgcccca aggacctgaa atgaccctgt   4320
gccttatttg aactaaccaa tcagttcgct tctcgcttct gttcgcgcgc ttctgctccc   4380
cgagctcaat aaaagagccc acaaccctc actcggcgcg ccagtcctcc gatagactgc   4440
gtcgcccggg tacccgtgtt ctcaataaac cctcttgcag ttgcatccga ctcgtggtct   4500
cgctgttcct tgggagggtc tcctctgagt gattgactgc ccactcgggg gtctttcat   4560 tctcgagcag cttggcgtaa tcatggtcat agctgtttcc tgtgtgaaat tgttatccgc   4620
tcacaattcc acacaacata cgagccggaa gcataaagtg taaagcctgg ggtgcctaat   4680
gagtgagcta actcacatta attgcgttgc gctcactgcc cgctttccag tcgggaaacc   4740
tgtcgtgcca gctgcattaa tgaatcggcc aacgcgcggg gagaggcggt ttgcgtattg   4800
```

-continued

```
ggcgctcttc cgcttcctcg ctcactgact cgctgcgctc ggtcgttcgg ctgcggcgag    4860
cggtatcagc tcactcaaag gcggtaatac ggttatccac agaatcaggg gataacgcag    4920
gaaagaacat gtgagcaaaa ggccagcaaa aggccaggaa ccgtaaaaag gccgcgttgc    4980
tggcgttttt ccataggctc cgcccccctg acgagcatca caaaaatcga cgctcaagtc    5040
agaggtggcg aaacccgaca ggactataaa gataccaggc gtttccccct ggaagctccc    5100
tcgtgcgctc tcctgttccg accctgccgc ttaccggata cctgtccgcc tttctccctt    5160
cgggaagcgt ggcgctttct catagctcac gctgtaggta tctcagttcg gtgtaggtcg    5220
ttcgctccaa gctgggctgt gtgcacgaac cccccgttca gcccgaccgc tgcgccttat    5280
ccggtaacta tcgtcttgag tccaacccgg taagacacga cttatcgcca ctggcagcag    5340
ccactggtaa caggattagc agagcgaggt atgtaggcgg tgctacagag ttcttgaagt    5400
ggtggcctaa ctacggctac actagaagaa cagtatttgg tatctgcgct ctgctgaagc    5460
cagttacctt cggaaaaaga gttggtagct cttgatccgg caaacaaacc accgctggta    5520
gcggtggttt ttttgtttgc aagcagcaga ttacgcgcag aaaaaaagga tctcaagaag    5580
atcctttgat cttttctacg gggtctgacg ctcagtggaa cgaaaactca cgttaaggga    5640
ttttggtcat gagattatca aaaaggatct tcacctagat ccttttaaat taaaaatgaa    5700
gttttaaatc aatctaaagt atatatgagt aaacttggtc tgacagttac caatgcttaa    5760
tcagtgaggc acctatctca gcgatctgtc tatttcgttc atccatagtt gcctgactcc    5820
ccgtcgtgta gataactacg atacgggagg gcttaccatc tggccccagt gctgcaatga    5880
taccgcgaga cccacgctca ccggctccag atttatcagc aataaaccag ccagccggaa    5940
gggccgagcg cagaagtggt cctgcaactt tatccgcctc catccagtct attaattgtt    6000
gccgggaagc tagagtaagt agttcgccag ttaatagttt cgcaacgtt gttgccattg    6060 ctacaggcat cgtggtgtca cgctcgtcgt ttggtatggc ttcattcagc tccggttccc    6120
aacgatcaag gcgagttaca tgatccccca tgttgtgcaa aaaagcggtt agctccttcg    6180
gtcctccgat cgttgtcaga agtaagttgg ccgcagtgtt atcactcatg gttatggcag    6240
cactgcataa ttctcttact gtcatgccat ccgtaagatg cttttctgtg actggtgagt    6300
actcaaccaa gtcattctga atagtgta tgcggcgacc gagttgctct tgcccggcgt    6360
caatacggga taataccgcg ccacatagca gaactttaaa agtgctcatc attggaaaac    6420
gttcttcggg gcgaaaactc tcaaggatct taccgctgtt gagatccagt tcgatgtaac    6480
ccactcgtgc acccaactga tcttcagcat cttttacttt caccagcgtt tctgggtgag    6540
caaaaacagg aaggcaaaat gccgcaaaaa agggaataag ggcgacacgg aaatgttgaa    6600
tactcatact cttccttttt caatattatt gaagcattta tcagggttat tgtctcatga    6660
gcggatacat atttgaatgt atttagaaaa ataaacaaat aggggttccg cgcacatttc    6720
cccgaaaagt gccacctgac gtctaagaaa ccattattat catgacatta acctataaaa    6780
ataggcgtat cacgaggccc tttcgtctcg cgcgtttcgg tgatgacggt gaaaacctct    6840
gacacatgca gctcccggag acggtcacag cttgtctgta agcggatgcc gggagcagac    6900
aagcccgtca gggcgcgtca gcgggtgttg gcgggtgtcg ggctggctt aactatgcgg    6960 catcagagca gattgtactg agagtgcacc atatgcggtg tgaaataccg cacagatgcg    7020
taaggagaaa ataccgcatc aggcgccatt cgccattcag gctgcgcaac tgttgggaag    7080
ggcgatcggt gcgggcctct tcgctattac gccagctggc gaaagggga tgtgctgcaa    7140 ggcgattaag ttgggtaacg ccagggtttt cccagtcacg acgttgtaaa acgacggcca    7200
```

```
gtgaattagt actctagctt aagtaacgcc attttgcaag gcatggaaaa tacataactg    7260
agaatagaga agttcaga                                                  7278

<210> SEQ ID NO 16
<211> LENGTH: 7269
<212> TYPE: DNA
<213> ORGANISM: artificial
<220> FEATURE:
<223> OTHER INFORMATION: pMP71-TCR1405hc

<400> SEQUENCE: 16
tcaaggttag gaacagagag acagcagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgataga ctgcgtcgcc cgggtacccg tattcccaat aaagcctctt gctgtttgca     420
tccgaatcgt ggactcgctg atccttggga gggtcctc agattgattg actgcccacc      480 tcggggtct ttcatttgga ggttccaccg agatttggag acccctgccc agggaccacc      540
gacccccccg ccgggaggta agctggccag cggtcgtttc gtgtctgtct ctgtctttgt     600
gcgtgtttgt gccggcatct aatgtttgcg cctgcgtctg tactagttgg ctaactagat     660
ctgtatctgg cggtcccgcg gaagaactga cgagttcgta ttcccggccg cagcccctgg     720
gagacgtccc agcggcctcg ggggcccgtt ttgtggccca ttctgtatca gttaacctac     780
ccgagtcgga cttttggag ctccgccact gtccgagggg tacgtggctt tgttggggga     840
cgagagacag agacacttcc cgcccccgtc tgaattttg ctttcggttt tacgccgaaa     900
ccgcgccgcg cgtcttgtct gctgcagcat cgttctgtgt tgtctctgtc tgactgtgtt     960
tctgtatttg tctgaaaatt agctcgacaa agttaagtaa tagtccctct ctccaagctc    1020
acttacaggc ggccgccacc atgctgtctt gttgctgct gctgctgggc ctgggcagcg    1080
tgttctctgc cgtgatcagc cagaagccca ccggacat ctgccagaga ggcaccagcc    1140
tgaccatcca gtgccaggtg acagccaag tgaccatgat gttctggtac agacagcagc    1200
ccggccagag cctgaccctg atcgccacag ccaatcaggg cagcgaggcc acatacgaga    1260
gcggcttcgt gatcgacaag ttccccatca gccgcccaa cctgaccttc agcaccctga    1320
ccgtgtccaa catgagcccc gaggacagca gcatctacct gtgcagcgtg aacaggaca    1380 ccaacaccgg cgagctgttc ttcggcgagg gcagcagact gaccgtgctg gaagacctga    1440
agaacgtgtt ccccccgag gtggccgtgt tcgagcccag cgaggccgag atcagccaca    1500
cccagaaagc caccctggtg tgcctggcca ccggcttcta ccccgaccac gtggagctgt    1560
cttggtgggt gaacggcaaa gaggtgcaca gcggcgtcag caccgacccc cagcccctga    1620
aagagcagcc cgccctgaac gacagccggt actgctgag cagccggctg agagtgagcg    1680
ccaccttctg gcagaacccc ggaaccact tccggtgcca ggtgcagttc tacggcctga    1740
gcgagaacga cgagtggacc caggacagag ccaagcccgt gacccagatc gtgagcgccg    1800
aggcctgggg cagagccgac tgcggcttca ccagcgagag ctaccagcag ggcgtgctgt    1860
ccgccacaat cctgtacgag atcctgctgg gcaaggccac cctgtacgcc gtgctggtgt    1920
```

```
ccgccctggt gctgatggcc atggtgaagc ggaaggacag ccggggcggc agcggcgcca    1980
ccaactttag cctgctgaaa caggccggcg acgtggaaga aaccctggcc cctatgacca    2040
gcatccgggc cgtgttcatc ttcctgtggc tgcagctgga cctcgtgaac ggcgagaatg    2100
tggaacagca cccctccacc ctgagcgtgc aggaaggcga tagcgccgtg attaagtgca    2160
cctacagcga cagcgccagc aactacttcc cctggtacaa gcaggaactg ggaaagggcc    2220
cccagctgat catcgacatc cggtccaacg tgggcgagaa gaaggaccag agaatcgccg    2280
tgaccctgaa caagaccgcc aagcacttca gcctgcacat caccgagaca cagcccgagg    2340
actccgccgt gtacttctgt gccgccgacc caacagcgg caacacccct ctggtgttcg    2400
gcaagggcac acggctgagc gtgatcgcca atatccagaa ccccgacccc gccgtgtacc    2460
agctgcggga cagcaagagc agcgacaaga gcgtgtgcct gttcaccgac ttcgacagcc    2520
agaccaacgt gagccagagc aaggactccg acgtgtacat caccgacaag accgtgctgg    2580
acatgcggag catggacttc aagagcaact ccgccgtggc ctggtccaac aagagcgact    2640
tcgcctgcgc caacgccttc aacaacagca tcatccccga ggacaccttt ttccccagcc    2700
ccgagagcag ctgcgacgtg aaactggtgg agaagagctt cgagaccgac accaacctga    2760
acttccagaa cctgtccgtg atcggcttcc ggatcctgct gctgaaggtg gccggcttca    2820
acctgctgat gaccctgcgg ctgtggagca gctgaattcg agcatcttac cgccatttat    2880
tcccatattt gttctgtttt tcttgatttg ggtatacatt taaatgttaa taaaacaaaa    2940
tggtggggca atcatttaca ttttatggga tatgtaatta ctagttcagg tgtattgcca    3000
caagacaaac atgttaagaa actttcccgt tatttacgct ctgttcctgt taatcaacct    3060
ctggattaca aaatttgtga agattgact gatattctta actatgttgc tccttttacg    3120
ctgtgtggat atgctgcttt aatgcctctg tatcatgcta ttgcttcccg tacggctttc    3180
gttttctcct ccttgtataa atcctggttg ctgtctcttt atgaggagtt gtggcccgtt    3240
gtccgtcaac gtggcgtggt gtgctctgtg tttgctgacg caaccccac tggctggggc    3300
attgccacca cctgtcaact ccttctggg actttcgctt ccccctccc gatcgccacg    3360
gcagaactca tcgccgcctg ccttgcccgc tgctggacag gggctaggtt gctgggcact    3420
gataattccg tggtgttgtc ggggaagctg acgtcctttc catggctgct cgcctgtgtt    3480
gccaactgga tcctgcgcgg gacgtccttc tgctacgtcc cttcggctct caatccagcg    3540
gacctccctt cccgaggcct tctgccggtt ctgcggcctc tcccgcgtct cgctttcgg    3600
cctccgacga gtcggatctc cctttgggcc gcctccccgc ctgtttcgcc tcggcgtccg    3660
gtccgtgttg cttggtcgtc acctgtgcag aattgcgaac catggattcc accgtgaact    3720
ttgtctcctg gcatgcaaat cgtcaacttg gcatgccaag aattaattcg gatccaagct    3780
taggcctgct cgctttcttg ctgtcccatt tctattaaag gttccttgt tccctaagtc    3840
caactactaa actgggggat attatgaagg gccttgagca tctggattct gcctagcgct    3900
aagcttaaca cgagccatag atagaataaa agattttatt tagtctccag aaaaagggg    3960
gaatgaaaga ccccacctgt aggtttggca agctagctta agtaacgcca ttttgcaagg    4020
catgaaaaat acataactga gaatagagaa gttcagatca aggttaggaa cagagagaca    4080
gcagaatatg ggccaaacag gatatctgtg gtaagcagtt cctgccccgg ctcagggcca    4140
agaacagttg gaacagcaga atatgggcca acaggatat ctgtggtaag cagttcctgc    4200
cccggctcag ggccaagaac agatggtccc cagatgcggt cccgccctca gcagtttcta    4260
gagaaccatc agatgtttcc agggtgcccc aaggacctga aatgaccctg tgccttattt    4320
```

```
gaactaacca atcagttcgc ttctcgcttc tgttcgcgcg cttctgctcc ccgagctcaa    4380
taaaagagcc cacaacccct cactcggcgc gccagtcctc cgatagactg cgtcgcccgg    4440
gtacccgtgt tctcaataaa ccctcttgca gttgcatccg actcgtggtc tcgctgttcc    4500
ttgggagggt ctcctctgag tgattgactg cccacctcgg gggtctttca ttctcgagca    4560
gcttggcgta atcatggtca tagctgtttc ctgtgtgaaa ttgttatccg ctcacaattc    4620
cacacaacat acgagccgga agcataaagt gtaaagcctg gggtgcctaa tgagtgagct    4680
aactcacatt aattgcgttg cgctcactgc ccgctttcca gtcgggaaac ctgtcgtgcc    4740
agctgcatta atgaatcggc caacgcgcgg ggagaggcgg tttgcgtatt gggcgctctt    4800
ccgcttcctc gctcactgac tcgctgcgct cggtcgttcg gctgcggcga gcggtatcag    4860
ctcactcaaa ggcggtaata cggttatcca cagaatcagg ggataacgca ggaaagaaca    4920
tgtgagcaaa aggccagcaa aaggccagga accgtaaaaa ggccgcgttg ctggcgtttt    4980
tccataggct ccgcccccct gacgagcatc acaaaaatcg acgctcaagt cagaggtggc    5040
gaaacccgac aggactataa agataccagg cgtttccccc tggaagctcc ctcgtgcgct    5100
ctcctgttcc gaccctgccg cttaccggat acctgtccgc ctttctccct tcgggaagcg    5160
tggcgctttc tcatagctca cgctgtaggt atctcagttc ggtgtaggtc gttcgctcca    5220
agctgggctg tgtgcacgaa ccccccgttc agcccgaccg ctgcgcctta tccggtaact    5280
atcgtcttga gtccaacccg gtaagacacg acttatcgcc actggcagca gccactggta    5340
acaggattag cagagcgagg tatgtaggcg gtgctacaga gttcttgaag tggtggccta    5400
actacggcta cactagaaga acagtatttg gtatctgcgc tctgctgaag ccagttacct    5460
tcggaaaaag agttggtagc tcttgatccg gcaaacaaac caccgctggt agcggtggtt    5520
tttttgtttg caagcagcag attacgcgca gaaaaaaagg atctcaagaa gatcctttga    5580
tcttttctac ggggtctgac gctcagtgga acgaaaactc acgttaaggg attttggtca    5640
tgagattatc aaaaaggatc ttcacctaga tccttttaaa ttaaaaatga agttttaaat    5700
caatctaaag tatatatgag taaacttggt ctgacagtta ccaatgctta atcagtgagg    5760
cacctatctc agcgatctgt ctatttcgtt catccatagt tgcctgactc cccgtcgtgt    5820
agataactac gatacgggag ggcttaccat ctggccccag tgctgcaatg ataccgcgag    5880
acccacgctc accggctcca gatttatcag caataaacca gccagccgga agggccgagc    5940
gcagaagtgg tcctgcaact ttatccgcct ccatccagtc tattaattgt tgccgggaag    6000
ctagagtaag tagttcgcca gttaatagtt tgcgcaacgt tgttgccatt gctacaggca    6060
tcgtggtgtc acgctcgtcg tttggtatgg cttcattcag ctccggttcc caacgatcaa    6120
ggcgagttac atgatccccc atgttgtgca aaaaagcggt tagctccttc ggtcctccga    6180
tcgttgtcag aagtaagttg gccgcagtgt tatcactcat ggttatggca gcactgcata    6240
attctcttac tgtcatgcca tccgtaagat gcttttctgt gactggtgag tactcaacca    6300
agtcattctg agaatagtgt atgcggcgac cgagttgctc ttgcccggcg tcaatacggg    6360
ataataccgc gccacatagc agaactttaa aagtgctcat cattggaaaa cgttcttcgg    6420
ggcgaaaact ctcaaggatc ttaccgctgt tgagatccag ttcgatgtaa cccactcgtg    6480
cacccaactg atcttcagca tcttttactt tcaccagcgt ttctgggtga gcaaaaacag    6540
gaaggcaaaa tgccgcaaaa aagggaataa gggcgacacg gaaatgttga atactcatac    6600
tcttcctttt tcaatattat tgaagcattt atcagggtta ttgtctcatg agcggataca    6660
```

```
tatttgaatg tatttagaaa aataaacaaa tagggtttcc gcgcacattt ccccgaaaag    6720
tgccacctga cgtctaagaa accattatta tcatgacatt aacctataaa aataggcgta    6780
tcacgaggcc ctttcgtctc gcgcgtttcg gtgatgacgg tgaaaacctc tgacacatgc    6840
agctcccgga cacggtcaca gcttgtctgt aagcggatgc cgggagcaga caagcccgtc    6900
agggcgcgtc agcgggtgtt ggcgggtgtc ggggctggct taactatgcg gcatcagagc    6960
agattgtact gagagtgcac catatgcggt gtgaaatacc gcacagatgc gtaaggagaa    7020
aataccgcat caggcgccat tcgccattca ggctgcgcaa ctgttgggaa gggcgatcgg    7080
tgcgggcctc ttcgctatta cgccagctgg cgaaaggggg atgtgctgca aggcgattaa    7140
gttgggtaac gccagggttt tcccagtcac gacgttgtaa aacgacggcc agtgaattag    7200
tactctagct taagtaacgc cattttgcaa ggcatggaaa atacataact gagaatagag    7260
aagttcaga                                                             7269

<210> SEQ ID NO 17
<211> LENGTH: 7239
<212> TYPE: DNA
<213> ORGANISM: artificial
<220> FEATURE:
<223> OTHER INFORMATION: pMP71_1405_mc

<400> SEQUENCE: 17
tcaaggttag gaacagagag acagcagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgataga ctgcgtcgcc cgggtacccg tattcccaat aaagcctctt gctgtttgca     420
tccgaatcgt ggactcgctg atccttggga gggtcctcc agattgattg actgcccacc     480 tcggggtct ttcatttgga ggttccaccg agatttggag accctgccc agggaccacc     540 gacccccccg ccgggaggta agctggccag cggtcgtttc gtgtctgtct ctgtctttgt     600
gcgtgtttgt gccggcatct aatgtttgcg cctgcgtctg tactagttgg ctaactagat     660
ctgtatctgg cggtcccgcg gaagaactga cgagttcgta ttcccggccg cagcccctgg     720
gagacgtccc agcggcctcg ggggcccgtt ttgtggccca ttctgtatca gttaacctac     780
ccgagtcgga cttttggag ctccgccact gtccgagggg tacgtggctt tgttggggga     840
cgagagacag agacacttcc cgcccccgtc tgaattttg cttcggtttt tacgccgaaa     900
ccgcgccgcg cgtcttgtct gctgcagcat cgttctgtgt tgtctctgtc tgactgtgtt     960
tctgtatttg tctgaaaatt agctcgacaa agttaagtaa tagtccctct ctccaagctc    1020
acttacaggc ggccgccacc atgctgtctt tgttgctgct gctgctgggc ctgggcagcg    1080
tgttctctgc cgtgatcagc cagaagccca gccgggacat ctgcagaga ggcaccagcc    1140 tgaccatcca gtgccaggtg gacagccaag tgaccatgat gttctggtac agacagcagc    1200
ccggccagag cctgacctg atcgccacag ccaatcaggg cagcgaggcc atacgagag    1260 gcggcttcgt gatcgacaag ttccccatca gccggcccaa cctgaccttc agcaccctga    1320
ccgtgtccaa catgagcccc gaggacagca gcatctacct gtgcagcgtg aacaggaca    1380 ccaacaccgg cgagctgttc ttcggcgagg gcagcagact gaccgtgctg aagatctgc    1440
```

```
ggaacgtgac cccccccaag gtgtccctgt tcgagcctag caaggccgag atcgccaaca    1500
agcagaaagc cacccctcgtg tgcctggcca gaggcttctt ccccgaccac gtggaactgt    1560
cttggtgggt caacggcaaa gaggtgcaca gcggcgtgtc caccgatccc caggcctaca    1620
aagagagcaa ctacagctac tgcctgagca gcaggctgcg ggtgtccgcc accttctggc    1680 acaaccccg  gaaccacttc agatgccagg tgcagtttca cggcctgagc gaagaggaca    1740
agtggcctga gggcagcccc aagcccgtga cccagaatat ttctgccgaa gcctggggca    1800
gagccgactg cggaatcaca agcgccagct accatcaggg cgtgctgagc gccacaatcc    1860
tgtacgagat cctgctgggc aaggccaccc tgtacgccgt gctggtgtct ggcctggtgc    1920
tgatggccat ggtcaagaag aagaactccg gcagcggcgc caccaacttt agcctgctga    1980
aacaggccgg cgacgtggaa gagaaccctg gccctatgac cagcatccgg gccgtgttca    2040
tcttcctgtg gctgcagctg acctcgtga  acggcgagaa tgtggaacag caccccctcca   2100 ccctgagcgt gcaggaaggc gatagcgccg tgattaagtg cacctacagc gacagcgcca    2160
gcaactactt cccctggtac aagcaggaac tgggaaaggg ccccccagctg atcatcgaca   2220 tccggtccaa cgtgggcgag aagaaggacc agagaatcgc cgtgaccctg aacaagaccg    2280
ccaagcactt cagcctgcac atcaccgaga cacagcccga ggactccgcc gtgtacttct    2340
gtgccgccag acccaacagc ggcaacaccc tctggtgtt  cggcaagggc acacggctga    2400
gcgtgatcgc caatatccag aaccccgagc ctgccgtgta ccagctgaag gaccccagaa    2460
gccaggatag caccctgtgc ctgttcaccg acttcgacag ccagatcaac gtgcccaaga    2520
ccatggaaag cggcaccttc atcaccgaca agacagtgct ggacatgaag gccatggaca    2580
gcaagagcaa cggcgccatt gcctggtcca accagaccag cttcacatgc caggacatct    2640
tcaaagagac aaacgccacc tacccccagca gcgacgtgcc ctgtgatgcc accctgacag    2700
agaagtcctt cgagacagac atgaacctga acttccagaa cctgtccgtg atgggcctga    2760
gaatcctgct gctgaaagtg gccggattca acctgctgat gaccctgcgg ctgtggtcca    2820
gctgaattcg agcatcttac cgccatttat tcccatattt gttctgtttt tcttgatttg    2880
ggtatacatt taaatgttaa taaaacaaaa tggtggggca atcatttaca ttttatggga    2940
tatgtaatta ctagttcagg tgtattgcca caagacaaac atgttaagaa actttcccgt    3000
tatttacgct ctgttcctgt taatcaacct ctggattaca aaatttgtga aagattgact    3060
gatattctta actatgttgc tccttttacg ctgtgtggat atgctgcttt aatgcctctg    3120
tatcatgcta ttgcttcccg tacggctttc gttttctcct ccttgtataa atcctggttg    3180
ctgtctcttt atgaggagtt gtggcccgtt gtccgtcaac gtggcgtggt gtgctctgtg    3240
tttgctgacg caaccccac  tggctggggc attgccacca cctgtcaact cctttctggg    3300
actttcgctt tccccctccc gatcgccacg gcagaactca tcgccgcctg ccttgcccgc    3360
tgctggacag gggctaggtt gctgggcact gataattccg tggtgttgtc ggggaagctg    3420
acgtcctttc catggctgct cgcctgtgtt gccaactgga tcctgcgcgg gacgtccttc    3480
tgctacgtcc cttcggctct caatccagcg gacctccctt cccgaggcct tctgccggtt    3540
ctgcggcctc tcccgcgtct tcgctttcgg cctccgacga tcggatctc  cctttgggcc    3600 gcctccccgc ctgtttcgcc tcggcgtccg gtccgtgttg cttggtcgtc acctgtgcag    3660
aattgcgaac catggattcc accgtgaact ttgtctcctg gcatgcaaat cgtcaacttg    3720
gcatgccaag aattaattcg gatccaagct taggcctgct cgctttcttg ctgtcccatt    3780
```

```
tctattaaag gttcctttgt tccctaagtc caactactaa actgggggat attatgaagg    3840
gccttgagca tctggattct gcctagcgct aagcttaaca cgagccatag atagaataaa    3900
agattttatt tagtctccag aaaaagggggg gaatgaaaga ccccacctgt aggtttggca    3960
agctagctta agtaacgcca ttttgcaagg catggaaaat acataactga gaatagagaa    4020
gttcagatca aggttaggaa cagagagaca gcagaatatg ggccaaacag gatatctgtg    4080
gtaagcagtt cctgccccgg ctcagggcca agaacagttg gaacagcaga atatgggcca    4140
aacaggatat ctgtggtaag cagttcctgc cccggctcag ggccaagaac agatggtccc    4200
cagatgcggt cccgccctca gcagtttcta gagaaccatc agatgtttcc agggtgcccc    4260
aaggacctga aatgaccctg tgccttattt gaactaacca atcagttcgc ttctcgcttc    4320
tgttcgcgcg cttctgctcc ccgagctcaa taaagagcc cacaaccccct cactcggcgc    4380 gccagtcctc cgatagactg cgtcgcccgg gtacccgtgt tctcaataaa ccctcttgca    4440
gttgcatccg actcgtggtc tcgctgttcc ttgggagggt ctcctctgag tgattgactg    4500
cccacctcgg gggtctttca ttctcgagca gcttggcgta atcatggtca tagctgtttc    4560
ctgtgtgaaa ttgttatccg ctcacaattc cacacaacat acgagccgga agcataaagt    4620
gtaaagcctg gggtgcctaa tgagtgagct aactcacatt aattgcgttg cgctcactgc    4680 ccgcttttcca gtcgggaaac ctgtcgtgcc agctgcatta tgaatcggc caacgcgcgg    4740 ggagaggcgg tttgcgtatt gggcgctctt ccgcttcctc gctcactgac tcgctgcgct    4800
cggtcgttcg gctgcggcga gcggtatcag ctcactcaaa ggcggtaata cggttatcca    4860
cagaatcagg ggataacgca ggaaagaaca tgtgagcaaa aggccagcaa aaggccagga    4920
accgtaaaaa ggccgcgttg ctggcgtttt tccataggct ccgcccccct gacgagcatc    4980
acaaaaatcg acgctcaagt cagaggtggc gaaacccgac aggactataa agataccagg    5040
cgtttccccc tggaagctcc ctcgtgcgct ctcctgttcc gaccctgccg cttaccggat    5100
acctgtccgc ctttctccct tcgggaagcg tggcgctttc tcatagctca cgctgtaggt    5160
atctcagttc ggtgtaggtc gttcgctcca agctgggctg tgtgcacgaa ccccccgttc    5220
agcccgaccg ctgcgcctta tccggtaact atcgtcttga gtccaacccg gtaagacacg    5280
acttatcgcc actggcagca gccactggta acaggattag cagagcgagg tatgtaggcg    5340
gtgctacaga gttcttgaag tggtggccta actacggcta cactagaaga acagtatttg    5400
gtatctgcgc tctgctgaag ccagttacct tcggaaaaag agttggtagc tcttgatccg    5460
gcaaacaaac caccgctggt agcggtggtt tttttgtttg caagcagcag attacgcgca    5520
gaaaaaaagg atctcaagaa gatcctttga tcttttctac ggggtctgac gctcagtgga    5580
acgaaaactc acgttaaggg attttggtca tgagattatc aaaaaggatc ttcacctaga    5640
tccttttaaa ttaaaaatga agttttaaat caatctaaag tatatatgag taaacttggt    5700
ctgacagtta ccaatgctta atcagtgagg cacctatctc agcgatctgt ctatttcgtt    5760
catccatagt tgcctgactc cccgtcgtgt agataactac gatacgggag ggcttaccat    5820
ctggccccag tgctgcaatg ataccgcgag acccacgctc accggctcca gatttatcag    5880
caataaacca gccagccgga agggccgagc gcagaagtgg tcctgcaact ttatccgcct    5940
ccatccagtc tattaattgt tgccgggaag ctagagtaag tagttcgcca gttaatagtt    6000
tgcgcaacgt tgttgccatt gctacaggca tcgtggtgtc acgctcgtcg tttggtatgg    6060
cttcattcag ctccggttcc caacgatcaa ggcgagttac atgatccccc atgttgtgca    6120
aaaaagcggt tagctccttc ggtcctccga tcgttgtcag aagtaagttg gccgcagtgt    6180
```

-continued

| | |
|---|---|
| tatcactcat ggttatggca gcactgcata attctcttac tgtcatgcca tccgtaagat | 6240 |
| gcttttctgt gactggtgag tactcaacca agtcattctg agaatagtgt atgcggcgac | 6300 |
| cgagttgctc ttgcccggcg tcaatacggg ataataccgc gccacatagc agaactttaa | 6360 |
| aagtgctcat cattggaaaa cgttcttcgg ggcgaaaact ctcaaggatc ttaccgctgt | 6420 |
| tgagatccag ttcgatgtaa cccactcgtg cacccaactg atcttcagca tcttttactt | 6480 |
| tcaccagcgt ttctgggtga gcaaaaacag gaaggcaaaa tgccgcaaaa aagggaataa | 6540 |
| gggcgacacg gaaatgttga atactcatac tcttcctttt tcaatattat tgaagcattt | 6600 |
| atcagggtta ttgtctcatg agcggataca tatttgaatg tatttagaaa aataaacaaa | 6660 |
| taggggttcc gcgcacattt ccccgaaaag tgccacctga cgtctaagaa accattatta | 6720 |
| tcatgacatt aacctataaa aataggcgta tcacgaggcc ctttcgtctc gcgcgtttcg | 6780 |
| gtgatgacgg tgaaaacctc tgacacatgc agctcccgga cgggtcaca gcttgtctgt | 6840 |
| aagcggatgc cgggagcaga caagcccgtc agggcgcgtc agcgggtgtt ggcgggtgtc | 6900 |
| ggggctggct taactatgcg gcatcagagc agattgtact gagagtgcac catatgcggt | 6960 |
| gtgaaatacc gcacagatgc gtaaggagaa aataccgcat caggcgccat cgccattca | 7020 |
| ggctgcgcaa ctgttgggaa gggcgatcgg tgcgggcctc ttcgctatta cgccagctgg | 7080 |
| cgaaaggggg atgtgctgca agcgattaa gttgggtaac gccagggttt cccagtcac | 7140 |
| gacgttgtaa aacgacggcc agtgaattag tactctagct taagtaacgc cattttgcaa | 7200 |
| ggcatggaaa atacataact gagaatagag aagttcaga | 7239 |

<210> SEQ ID NO 18
<211> LENGTH: 7269
<212> TYPE: DNA
<213> ORGANISM: artificial
<220> FEATURE:
<223> OTHER INFORMATION: pMP71-TCR1405mmc

<400> SEQUENCE: 18

| | |
|---|---|
| tcaaggttag gaacagagag acagcagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgataga ctgcgtcgcc cgggtacccg tattcccaat aaagcctctt gctgtttgca | 420 |
| tccgaatcgt ggactcgctg atccttggga gggtctcctc agattgattg actgcccacc | 480 |
| tcgggggtct ttcatttgga ggttccaccg agatttggag acccctgccc agggaccacc | 540 |
| gacccccccg ccgggaggta agctggccag cggtcgtttc gtgtctgtct ctgtctttgt | 600 |
| gcgtgtttgt gccggcatct aatgtttgcg cctgcgtctg tactagttgg ctaactagat | 660 |
| ctgtatctgg cggtcccgcg gaagaactga cgagttcgta ttcccggccg cagcccctgg | 720 |
| gagacgtccc agcggcctcg ggggcccgtt ttgtggccca ttctgtatca gttaacctac | 780 |
| ccgagtcgga cttttggag ctccgccact gtccgagggg tacgtggctt tgttggggga | 840 |
| cgagagacag agacacttcc cgcccccgtc tgaattttg ctttcggttt tacgccgaaa | 900 |
| ccgcgccgcg cgtcttgtct gctgcagcat cgttctgtgt tgtctctgtc tgactgtgtt | 960 |

-continued

```
tctgtatttg tctgaaaatt agctcgacaa agttaagtaa tagtccctct ctccaagctc    1020
acttacaggc ggccgccacc atgctgtctt tgttgctgct gctgctgggc ctgggcagcg    1080
tgttctctgc cgtgatcagc cagaagccca gccgggacat ctgccagaga ggcaccagcc    1140
tgaccatcca gtgccaggtg dacagccaag tgaccatgat gttctggtac agacagcagc    1200
ccggccagag cctgaccctg atcgccacag ccaatcaggg cagcgaggcc acatacgaga    1260
gcggcttcgt gatcgacaag ttccccatca gccggcccaa cctgaccttc agcaccctga    1320
ccgtgtccaa catgagcccc gaggacagca gcatctacct gtgcagcgtg aacaggaca    1380
ccaacaccgg cgagctgttc ttcggcgagg gcagcagact gaccgtgctg aagacctga    1440
agaacgtgtt cccccccgag gtggccgtgt cgagcccag caaggccgag atcgcccaca    1500
cccagaaagc caccctggtg tgcctggcca ccggcttcta ccccgaccac gtggaactgt    1560
cttggtgggt gaacggcaaa gaggtgcaca cgggcgtgtg taccgacccc cagcccctga    1620
aagagcagcc tgccctgaac gactccggt actgcctgag cagccggctg agagtgtccg    1680
ccaccttctg gcagaacccc cggaaccact tcagatgcca ggtgcagttc tacgcctga    1740
gcgagaacga cgagtggacc caggaccggg ccaagcccgt gacccagatt gtgtctgccg    1800
aggcctgggg cagagctgat tgtggcatca ccagcgccag ctaccaccag ggcgtgctga    1860
gcgccaccat cctgtacgag atcctgctgg gcaaggccac cctgtacgcc gtgctggtgt    1920
ccgccctggt gctgatggcc atggtgaaac ggaaggacag cagaggcggc agcggcgcca    1980
ccaactttag cctgctgaaa caggccggcg acgtggaaga aaccctggc cctatgacca    2040
gcatccgggc cgtgttcatc ttcctgtggc tgcagctgga cctcgtgaac ggcgagaatg    2100
tggaacagca cccctccacc ctgagcgtgc aggaaggcga tagcgccgtg attaagtgca    2160
cctacagcga cagcgccagc aactacttcc cctggtacaa gcaggaactg ggaaagggcc    2220
cccagctgat catcgacatc cggtccaacg tgggcgagaa aaggaccag agaatcgccg    2280
tgaccctgaa caagaccgcc aagcacttca gcctgcacat caccgagaca cagcccgagg    2340
actccgccgt gtacttctgt gccgccagac ccaacagcgg caacacccct ctggtgttcg    2400
gcaagggcac acggctgagc gtgatcgcca atatccagaa ccccgacccc gccgtgtacc    2460
agctgcggga cagcaagagc agcgacaaga gcgtgtgcct gttcaccgac ttcgacagcc    2520
agaccaacgt gtcccagagc aaggacagcg acgtgtacat caccgacaag tgcgtgctgg    2580
acatgcggag catggacttc aagagcaact ccgccgtggc ctggtccaac aagagcgact    2640
tcgcctgcgc caacgccttc aacaacagca tcatccccga ggacacattc ttccccagct    2700
ccgacgtgcc ctgcgacgtg aagctggtgg aaaagagctt cgagacagac accaacctga    2760
acttccagaa cctgagcgtg atcggcttcc ggatcctgct gctgaaggtg gctggcttca    2820
acctgctgat gaccctgcgg ctgtggagca gctgaattcg agcatcttac cgccatttat    2880
tcccatattt gttctgtttt tcttgatttg ggtatacatt taaatgttaa taaaacaaaa    2940
tggtggggca atcatttaca ttttatggga tatgtaatta ctagttcagg tgtattgcca    3000
caagacaaac atgttaagaa actttcccgt tatttacgct ctgttcctgt taatcaacct    3060
ctggattaca aaatttgtga agattgact gatattctta actatgttgc tccttttacg    3120
ctgtgtggat atgctgcttt aatgcctctg tatcatgcta ttgcttcccg tacggctttc    3180
gttttctcct ccttgtataa atcctggttg ctgtctcttt atgaggagtt gtggcccgtt    3240
gtccgtcaac gtggcgtggt gtgctctgtg tttgctgacg caacccccac tggctggggc    3300
attgccacca cctgtcaact ccttctctggg acttcgctt tccccctccc gatcgccacg    3360
```

```
gcagaactca tcgccgcctg ccttgcccgc tgctggacag gggctaggtt gctgggcact    3420
gataattccg tggtgttgtc ggggaagctg acgtcctttc catggctgct cgcctgtgtt    3480
gccaactgga tcctgcgcgg gacgtccttc tgctacgtcc cttcggctct caatccagcg    3540
gacctcccct cccgaggcct tctgccggtt ctgcggcctc tcccgcgtct tcgctttcgg    3600
cctccgacga gtcggatctc cctttgggcc gcctccccgc tgtttcgcc tcggcgtccg     3660
gtccgtgttg cttggtcgtc acctgtgcag aattgcgaac catggattcc accgtgaact    3720
ttgtctcctg gcatgcaaat cgtcaacttg gcatgccaag aattaattcg gatccaagct    3780
taggcctgct cgcttcttg ctgtcccatt tctattaaag gttcctttgt tccctaagtc     3840
caactactaa actgggggat attatgaagg gccttgagca tctggattct gcctagcgct    3900
aagcttaaca cgagccatag atagaataaa agattttatt tagtctccag aaaaaggggg    3960
gaatgaaaga ccccacctgt aggtttggca agctagctta agtaacgcca ttttgcaagg    4020
catggaaaat acataactga aatagagaa gttcagatca aggttaggaa cagagagaca     4080
gcagaatatg ggccaaacag gatatctgtg gtaagcagtt cctgccccgg ctcagggcca    4140
agaacagttg gaacagcaga atatgggcca acaggatat ctgtggtaag cagttcctgc     4200
cccggctcag ggccaagaac agatggtccc cagatgcggt cccgccctca gcagtttcta    4260
gagaaccatc agatgtttcc agggtgcccc aaggacctga atgaccctg tgccttattt     4320
gaactaacca atcagttcgc ttctcgcttc tgttcgcgcg cttctgctcc ccgagctcaa    4380
taaaagagcc cacaacccct cactcggcgc gccagtcctc cgatagactg cgtcgcccgg    4440
gtacccgtgt tctcaataaa ccctcttgca gttgcatccg actcgtggtc tcgctgttcc    4500
ttgggagggt ctcctctgag tgattgactg cccacctcgg gggtcttca ttctcgagca     4560
gcttggcgta atcatggtca tagctgtttc ctgtgtgaaa ttgttatccg ctcacaattc    4620
cacacaacat acgagccgga agcataaagt gtaaagcctg gggtgcctaa tgagtgagct    4680
aactcacatt aattgcgttg cgctcactgc ccgctttcca gtcgggaaac ctgtcgtgcc    4740
agctgcatta atgaatcggc caacgcgcgg ggagaggcgg tttgcgtatt gggcgctctt    4800
ccgcttcctc gctcactgac tcgctgcgct cggtcgttcg gctgcggcga gcggtatcag    4860
ctcactcaaa ggcggtaata cggttatcca cagaatcagg ggataacgca ggaaagaaca    4920
tgtgagcaaa aggccagcaa aaggccagga accgtaaaaa ggccgcgttg ctggcgtttt    4980
tccataggct ccgcccccct gacgagcatc acaaaaatcg acgctcaagt cagaggtggc    5040
gaaacccgac aggactataa agataccagg cgtttccccc tggaagctcc ctcgtgcgct    5100
ctcctgttcc gaccctgccg cttaccggat acctgtccgc ctttctccct tcgggaagcg    5160
tggcgctttc tcatagctca cgctgtaggt atctcagttc ggtgtaggtc gttcgctcca    5220
agctgggctg tgtgcacgaa ccccccgttc agcccgaccg ctgcgcctta tccggtaact    5280
atcgtcttga gtccaacccg gtaagacacg acttatcgcc actggcagca gccactggta    5340
acaggattag cagagcgagg tatgtaggcg gtgctacaga gttcttgaag tggtggccta    5400
actacggcta cactagaaga acagtatttg gtatctgcgc tctgctgaag ccagttacct    5460
tcggaaaaag agttggtagc tcttgatccg gcaaacaaac caccgctggt agcggtggtt    5520
ttttgtttg caagcagcag attacgcgca gaaaaaagg atctcaagaa gatcctttga     5580
tcttttctac ggggtctgac gctcagtgga acgaaaactc acgttaaggg attttggtca    5640
tgagattatc aaaaaggatc ttcacctaga tccttttaaa ttaaaaatga agttttaaat    5700
```

```
caatctaaag tatatatgag taaacttggt ctgacagtta ccaatgctta atcagtgagg      5760
cacctatctc agcgatctgt ctatttcgtt catccatagt tgcctgactc cccgtcgtgt      5820
agataactac gatacgggag ggcttaccat ctggccccag tgctgcaatg ataccgcgag      5880
acccacgctc accggctcca gatttatcag caataaacca gccagccgga agggccgagc      5940
gcagaagtgg tcctgcaact ttatccgcct ccatccagtc tattaattgt tgccgggaag      6000
ctagagtaag tagttcgcca gttaatagtt tgcgcaacgt tgttgccatt gctacaggca      6060
tcgtggtgtc acgctcgtcg tttggtatgg cttcattcag ctccggttcc caacgatcaa      6120
ggcgagttac atgatccccc atgttgtgca aaaaagcggt tagctccttc ggtcctccga      6180
tcgttgtcag aagtaagttg gccgcagtgt tatcactcat ggttatggca gcactgcata      6240
attctcttac tgtcatgcca tccgtaagat gcttttctgt gactggtgag tactcaacca      6300
agtcattctg agaatagtgt atgcggcgac cgagttgctc ttgcccggcg tcaatacggg      6360
ataataccgc gccacatagc agaactttaa aagtgctcat cattggaaaa cgttcttcgg      6420
ggcgaaaact ctcaaggatc ttaccgctgt tgagatccag ttcgatgtaa cccactcgtg      6480
cacccaactg atcttcagca tcttttactt tcaccagcgt ttctgggtga gcaaaaacag      6540
gaaggcaaaa tgccgcaaaa aagggaataa gggcgacacg gaaatgttga atactcatac      6600
tcttcctttt tcaatattat tgaagcattt atcagggtta ttgtctcatg agcggataca      6660
tatttgaatg tatttagaaa aataaacaaa taggggttcc gcgcacattt ccccgaaaag      6720
tgccacctga cgtctaagaa accattatta tcatgacatt aacctataaa aataggcgta      6780
tcacgaggcc ctttcgtctc gcgcgtttcg gtgatgacgg tgaaaacctc tgacacatgc      6840
agctcccgga gacggtcaca gcttgtctgt aagcggatgc cgggagcaga caagcccgtc      6900
agggcgcgtc agcgggtgtt ggcgggtgtc ggggctggct taactatgcg gcatcagagc      6960
agattgtact gagagtgcac catatgcggt gtgaaatacc gcacagatgc gtaaggagaa      7020
aataccgcat caggcgccat tcgccattca ggctgcgcaa ctgttgggaa gggcgatcgg      7080
tgcgggcctc ttcgctatta cgccagctgg cgaaaggggg atgtgctgca aggcgattaa      7140
gttgggtaac gccagggttt tcccagtcac gacgttgtaa aacgacggcc agtgaattag      7200
tactctagct taagtaacgc catttttgcaa ggcatggaaa atacataact gagaatagag      7260
aagttcaga                                                             7269

<210> SEQ ID NO 19
<211> LENGTH: 7308
<212> TYPE: DNA
<213> ORGANISM: artificial
<220> FEATURE:
<223> OTHER INFORMATION: pMP71-TCR1705hc

<400> SEQUENCE: 19
tcaaggttag gaacagagag acagcagaat atgggccaaa caggatatct gtggtaagca        60
gttcctgccc cggctcaggg ccaagaacag ttggaacagc agaatatggg ccaaacagga       120
tatctgtggt aagcagttcc tgccccggct cagggccaag acagatggt ccccagatgc       180 ggtcccgccc tcagcagttt ctagagaacc atcagatgtt tccagggtgc cccaaggacc       240
tgaaatgacc ctgtgcctta tttgaactaa ccaatcagtt cgcttctcgc ttctgttcgc       300
gcgcttctgc tccccgagct caataaaaga gcccacaacc cctcactcgg cgcgccagtc       360
ctccgataga ctgcgtcgcc cgggtacccg tattcccaat aaagcctctt gctgtttgca       420
tccgaatcgt ggactcgctg atccttggga gggtctcctc agattgattg actgcccacc       480
```

```
tcgggggtct ttcatttgga ggttccaccg agatttggag acccctgccc agggaccacc    540
gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttggag ctccgccact gtccgagggg tacgtggctt tgttggggga    840
cgagagacag agacacttcc cgccccgtc tgaattttg ctttcggttt tacgccgaaa      900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atgctgtctc cagatctgcc tgacagcgcc tggaacacca   1080
gactgctgtg ccacgtgatg ctgtgcctgc tgggagccgt gtctgtggct gctggcgtga   1140
tccagagccc cagacacctg atcaaagaga agagagagac agccaccctg aagtgctacc   1200
ccatccccag gcacgacacc gtgtactggt atcagcaggg cccaggccag gacccccagt   1260
tcctgatcag cttctacgag aagatgcaga gcgacaaggg cagcatcccc gacagattca   1320
gcgcccagca gttcagcgac taccacagcg agctgaacat gagcagcctg gaactgggcg   1380
acagcgccct gtacttctgc gccagctcct ttagaggcgg cggagccaac gtgctgacct   1440
ttggcgctgg cagcagactg accgtgctgg aagacctgaa gaacgtgttc cccccgagg    1500
tggccgtgtt cgagcccagc gaggccgaga tcagccacac ccagaaagcc acctggtgt   1560
gcctggccac cggcttctac cccgaccacg tggagctgtc ttggtgggtg aacggcaaag   1620
aggtgcacag cggcgtcagc accgaccccc agccctgaa agagcagccc gccctgaacg   1680
acagccggta ctgcctgagc agccggctga gagtgagcgc caccttctgg cagaaccccc   1740
ggaaccactt ccggtgccag gtgcagttct acggcctgag cgagaacgac gagtggaccc   1800
aggacagagc caagcccgtg acccagatcg tgagcgccga ggcctggggc agagccgact   1860
gcggcttcac cagcgagagc taccagcagg gcgtgctgtc cgccacaatc ctgtacgaga   1920
tcctgctggg caaggccacc ctgtacgccg tgctggtgtc cgccctggtg ctgatggcca   1980
tggtgaagcg gaaggacagc cggggcggca gcggcgccac caactttagc ctgctgaaac   2040
aggccggcga cgtggaagag aaccctggcc ccatgatgaa gtccctgcgg gtgctgctcg   2100
tgatcctgtg gctgcagctg agctgggtgt ggtcccagca gaaagaggtg gaacaggacc   2160
caggccctct gagcgtgcca gagggcgcta tcgtgtccct gaattgcacc tacagcaaca   2220
gcgccttcca gtacttcatg tggtacagac agtacagccg gaagggcccc gagctgctga   2280
tgtacaccta ctccagcggc aacaaagagg acggccggtt cacagccag gtggacaaga   2340
gcagcaagta catctcccgt ttcatccggg acagccagcc cagcgactct gccacatacc   2400
tgtgcgccat gagcgacacc ggcaaccagt tctacttcgg caccggcacc tccctgaccg   2460
tgatccccaa catccagaac cccgaccccg ccgtgtacca gctgcgggac agcaagagca   2520
gcgacaagag cgtgtgcctg ttcaccgact tcgacagcca gaccaacgtg agccagagca   2580
aggactccga cgtgtacatc accgacaaga ccgtgctgga catgcggagc atggacttca   2640
agagcaactc cgccgtggcc tggtccaaca agagcgactt cgcctgcgcc aacgccttca   2700
acaacagcat catccccgag gacacctttt tccccagccc cgagagcagc tgcgacgtga   2760
aactggtgga gaagagcttc gagaccgaca ccaacctgaa cttccagaac ctgtccgtga   2820
```

```
tcggcttccg gatcctgctg ctgaaggtgg ccggcttcaa cctgctgatg accctgcggc    2880
tgtggagcag ctgaattcga gcatcttacc gccatttatt cccatatttg ttctgttttt    2940
cttgatttgg gtatacattt aaatgttaat aaaacaaaat ggtggggcaa tcatttacat    3000
tttatgggat atgtaattac tagttcaggt gtattgccac aagacaaaca tgttaagaaa    3060 cttttcccgtt atttacgctc tgttcctgtt aatcaacctc tggattacaa aatttgtgaa    3120
agattgactg atattcttaa ctatgttgct ccttttacgc tgtgtggata tgctgcttta    3180
atgcctctgt atcatgctat tgcttcccgt acggctttcg ttttctcctc cttgtataaa    3240
tcctggttgc tgtctcttta tgaggagttg tggcccgttg tccgtcaacg tggcgtggtg    3300
tgctctgtgt ttgctgacgc aacccccact ggctggggca ttgccaccac ctgtcaactc    3360 cttctctggga ctttcgcttt cccctcccg atcgccacgg cagaactcat cgccgcctgc    3420
cttgcccgct gctggacagg ggctaggttg ctgggcactg ataattccgt ggtgttgtcg    3480
gggaagctga cgtccttttcc atggctgctc gcctgtgttg ccaactggat cctgcgcggg    3540
acgtccttct gctacgtccc ttcggctctc aatccagcgg acctcccttc cgaggcctt    3600 ctgccggttc tgcggcctct cccgcgtctt cgctttcggc ctccgacgag tcggatctcc    3660
ctttgggccg cctccccgcc tgtttcgcct cggcgtccgg tccgtgttgc ttggtcgtca    3720
cctgtgcaga attgcgaacc atggattcca ccgtgaactt tgtctcctgg catgcaaatc    3780
gtcaacttgg catgccaaga attaattcgg atccaagctt aggcctgctc gctttcttgc    3840
tgtcccattt ctattaaagg ttcctttgtt ccctaagtcc aactactaaa ctggggggata    3900 ttatgaaggg ccttgagcat ctggattctg cctagcgcta agcttaacac gagccataga    3960
tagaataaaa gattttattt agtctccaga aaaagggggg aatgaaagac cccacctgta    4020
ggtttggcaa gctagcttaa gtaacgccat tttgcaaggc atggaaaata caactgag      4080 aatagagaag ttcagatcaa ggttaggaac agagagacag cagaatatgg ccaaacagg    4140 atatctgtgg taagcagttc ctgccccggc tcagggccaa gaacagttgg aacagcagaa    4200
tatgggccaa acaggatatc tgtggtaagc agttcctgcc ccggctcagg gccaagaaca    4260
gatggtcccc agatgcggtc ccgccctcag cagtttctag agaaccatca gatgtttcca    4320
gggtgcccca aggacctgaa atgaccctgt gccttatttg aactaaccaa tcagttcgct    4380
tctcgcttct gttcgcgcgc ttctgctccc gagctcaat aaaagagccc acaacccctc    4440
actcggcgcg ccagtcctcc gatagactgc gtcgcccggg tacccgtgtt ctcaataaac    4500
cctcttgcaa ttgcatccga ctcgtggtct cgctgttcct tgggagggtc tcctctgagt    4560
gattgactgc ccacctcggg ggtctttcat tctcgagcag cttggcgtaa tcatggtcat    4620 agctgttttcc tgtgtgaaat tgttatccgc tcacaattcc acacaacata cgagccggaa    4680
gcataaagtg taaagcctgg ggtgcctaat gagtgagcta actcacatta attgcgttgc    4740
gctcactgcc cgctttccag tcgggaaacc tgtcgtgcca gctgcattaa tgaatcggcc    4800
aacgcgcggg gagaggcggt ttgcgtattg ggcgctcttc cgcttcctcg ctcactgact    4860
cgctgcgctc ggtcgttcgg ctgcggcgag cggtatcagc tcactcaaag gcggtaatac    4920
ggttatccac agaatcaggg gataacgcag gaaagaacat gtgagcaaaa ggccagcaaa    4980
aggccaggaa ccgtaaaaag gccgcgttgc tggcgttttt ccataggctc cgcccccctg    5040
acgagcatca caaaaatcga cgctcaagtc agaggtggcg aaacccgaca ggactataaa    5100
gataccaggc gtttccccct ggaagctccc tcgtgcgctc tcctgttccg accctgccgc    5160
ttaccggata cctgtccgcc tttctccctt cgggaagcgt ggcgctttct catagctcac    5220
```

-continued

```
gctgtaggta tctcagttcg gtgtaggtcg ttcgctccaa gctgggctgt gtgcacgaac    5280
cccccgttca gcccgaccgc tgcgccttat ccggtaacta tcgtcttgag tccaacccgg    5340
taagacacga cttatcgcca ctggcagcag ccactggtaa caggattagc agagcgaggt    5400
atgtaggcgg tgctacagag ttcttgaagt ggtggcctaa ctacggctac actagaagaa    5460
cagtatttgg tatctgcgct ctgctgaagc cagttacctt cggaaaaaga gttggtagct    5520
cttgatccgg caaacaaacc accgctggta gcggtggttt ttttgtttgc aagcagcaga    5580
ttacgcgcag aaaaaagga tctcaagaag atcctttgat cttttctacg ggtctgacg    5640 ctcagtggaa cgaaaactca cgttaaggga ttttggtcat gagattatca aaaaggatct    5700
tcacctagat ccttttaaat taaaaatgaa gttttaaatc aatctaaagt atatatgagt    5760
aaacttggtc tgacagttac caatgcttaa tcagtgaggc acctatctca gcgatctgtc    5820
tatttcgttc atccatagtt gcctgactcc ccgtcgtgta gataactacg atacgggagg    5880
gcttaccatc tggccccagt gctgcaatga taccgcgaga cccacgctca ccggctccag    5940
atttatcagc aataaaccag ccagccggaa gggccgagcg cagaagtggt cctgcaactt    6000
tatccgcctc catccagtct attaattgtt gccgggaagc tagagtaagt agttcgccag    6060
ttaatagttt gcgcaacgtt gttgccattg ctacaggcat cgtggtgtca cgctcgtcgt    6120
ttggtatggc ttcattcagc tccggttccc aacgatcaag gcgagttaca tgatccccca    6180
tgttgtgcaa aaaagcggtt agctccttcg gtcctccgat cgttgtcaga agtaagttgg    6240
ccgcagtgtt atcactcatg gttatggcag cactgcataa ttctcttact gtcatgccat    6300
ccgtaagatg cttttctgtg actggtgagt actcaaccaa gtcattctga atagtgta    6360 tgcggcgacc gagttgctct tgcccggcgt caatacggga taataccgcg ccacatagca    6420
gaactttaaa agtgctcatc attggaaaac gttcttcggg gcgaaaactc tcaaggatct    6480
taccgctgtt gagatccagt tcgatgtaac ccactcgtgc acccaactga tcttcagcat    6540
cttttacttt caccagcgtt tctgggtgag caaaaacagg aaggcaaaat gccgcaaaaa    6600
agggaataag ggcgacacgg aaatgttgaa tactcatact cttcctttt caatattatt    6660 gaagcattta tcagggttat tgtctcatga gcggatacat atttgaatgt atttagaaaa    6720
ataaacaaat aggggttccg cgcacatttc cccgaaaagt gccacctgac gtctaagaaa    6780
ccattattat catgacatta acctataaaa ataggcgtat cacgaggccc tttcgtctcg    6840
cgcgtttcgg tgatgacggt gaaaacctct gacacatgca gctcccggag acggtcacag    6900
cttgtctgta agcggatgcc gggagcagac aagcccgtca gggcgcgtca gcgggtgttg    6960
gcgggtgtcg ggctggctt aactatgcgg catcagagca gattgtactg agagtgcacc    7020
atatgcggtg tgaaataccg cacagatgcg taaggagaaa ataccgcatc aggcgccatt    7080
cgccattcag gctgcgcaac tgttgggaag ggcgatcggt gcgggcctct tcgctattac    7140
gccagctggc gaaaggggga tgtgctgcaa ggcgattaag ttgggtaacg ccagggtttt    7200
cccagtcacg acgttgtaaa acgacggcca gtgaattagt actctagctt aagtaacgcc    7260
attttgcaag gcatggaaaa tacataactg agaatagaga agttcaga              7308
```

```
<210> SEQ ID NO 20
<211> LENGTH: 7278
<212> TYPE: DNA
<213> ORGANISM: artificial
<220> FEATURE:
<223> OTHER INFORMATION: pMP71_1705_mc
```

```
<400> SEQUENCE: 20
tcaaggttag gaacagagag acagcagaat atgggccaaa caggatatct gtggtaagca      60
gttcctgccc cggctcaggg ccaagaacag ttggaacagc agaatatggg ccaaacagga     120
tatctgtggt aagcagttcc tgccccggct cagggccaag aacagatggt ccccagatgc     180
ggtcccgccc tcagcagttt ctagagaacc atcagatgtt tccagggtgc cccaaggacc     240
tgaaatgacc ctgtgcctta tttgaactaa ccaatcagtt cgcttctcgc ttctgttcgc     300
gcgcttctgc tccccgagct caataaaaga gcccacaacc cctcactcgg cgcgccagtc     360
ctccgataga ctgcgtcgcc cgggtacccg tattcccaat aaagcctctt gctgtttgca     420
tccgaatcgt ggactcgctg atccttggga gggtctcctc agattgattg actgcccacc     480
tcggggtct ttcatttgga ggttccaccg agatttggag accctgccc agggaccacc      540
gaccccccg ccgggaggta agctggccag cggtcgtttc gtgtctgtct ctgtctttgt      600
gcgtgtttgt gccggcatct aatgtttgcg cctgcgtctg tactagttgg ctaactagat     660
ctgtatctgg cggtcccgcg gaagaactga cgagttcgta ttcccggccg cagccctgg     720
gagacgtccc agcggcctcg ggggcccgtt ttgtggccca ttctgtatca gttaacctac     780
ccgagtcgga cttttggag ctccgccact gtccgagggg tacgtggctt tgttggggga     840
cgagagacag agacacttcc cgcccccgtc tgaattttttg ctttcggttt tacgccgaaa    900
ccgcgccgcg cgtcttgtct gctgcagcat cgttctgtgt tgtctctgtc tgactgtgtt     960
tctgtatttg tctgaaaatt agctcgacaa agttaagtaa tagtccctct ctccaagctc    1020
acttacaggc ggccgccacc atgctgtctc cagatctgcc tgacagcgcc tggaacacca    1080
gactgctgtg ccacgtgatg ctgtgcctgc tgggagccgt gtctgtggct gctggcgtga    1140
tccagagccc cagacacctg atcaaagaga agagagagac agccaccctg aagtgctacc    1200
ccatccccag gcacgacacc gtgtactggt atcagcaggg cccaggccag gaccccagt     1260
tcctgatcag cttctacgag aagatgcaga gcgacaaggg cagcatcccc gacagattca    1320
gcgcccagca gttcagcgac taccacagcg agctgaacat gagcagcctg gaactgggcg    1380
acagcgccct gtacttctgc gccagctcct ttagaggcgg cggagccaac gtgctgacct    1440
ttggcgctgg cagcagactg accgtgctgg aagatctgcg gaacgtgacc cccccaagg    1500
tgtccctgtt cgagcctagc aaggccgaga tcgccaacaa gcagaaagcc acactcgtgt    1560
gcctggccag aggcttcttc cccgaccacg tggaactgtc ttggtgggtc aacggcaaag    1620
aggtgcacag cggcgtgtcc accgatcctc aggcctacaa agagagcaac tacagctact    1680
gcctgagcag caggctgcgg gtgtccgcca ccttctggca acccccgg aaccacttca      1740
gatgccaggt gcagtttcac ggcctgagcg aagaggacaa gtggcccgag gcagccctta    1800
agcccgtgac ccagaatatc tctgccgagg cctggggcag agccgactgt ggaattacca    1860
gcgccagcta ccaccaggg gtgctgtctc tccaccatcct gtacgagatc ctgctgggca    1920
aggccaccct gtacgccgtg ctggtgtctg gcctggtgct gatggccatg gtcaagaaga    1980
agaacagcgg cagcggcgcc accaactta gcctgctgaa acaggccggc gacgtggaag    2040
agaaccctgg ccccatgatg aagtccctgc gggtgctgct cgtgatcctg tggctgcagc    2100
tgagctgggt gtggtcccag cagaaagagg tggaacagga cccaggccct ctgagcgtgc    2160
cagagggcgc tatcgtgtcc ctgaattgca cctacagcaa cagcgccttc cagtacttca    2220
tgtggtacag acagtacagc cggaagggcc ccgagctgct gatgtacacc tactccagcg    2280
gcaacaaaga ggacggccgg ttcacagccc aggtggacaa gagcagcaag tacatctccc    2340
```

```
tgttcatccg ggacagccag cccagcgact ctgccacata cctgtgcgcc atgagcgaca    2400
ccggcaacca gttctacttc ggcaccggca cctccctgac cgtgatcccc aacatccaga    2460
accccgagcc cgccgtgtac cagctgaagg accctagaag ccaggacagc accctgtgcc    2520
tgttcaccga cttcgacagc cagatcaacg tgcccaagac catggaaagc ggcaccttca    2580
tcaccgacaa gacagtgctg gacatgaagg ccatggacag caagagcaac ggcgccattg    2640
cctggtccaa ccagaccagc ttcacatgcc aggacatctt caagagagac aacgccacct    2700
accccagcag cgacgtgccc tgtgatgcca cactgaccga agtccttc gagacagaca     2760 tgaacctgaa cttccagaac ctgagcgtga tgggcctgag aatcctgctg ctgaaggtgg    2820
ccggcttcaa cctgctgatg accctgagac tgtggtccag ctgaattcga gcatcttacc    2880
gccatttatt cccatatttg ttctgttttt cttgatttgg gtatacattt aaatgttaat    2940
aaaacaaaat ggtggggcaa tcatttacat tttatgggat atgtaattac tagttcaggt    3000
gtattgccac aagacaaaca tgttaagaaa ctttcccgtt atttacgctc tgttcctgtt    3060
aatcaacctc tggattacaa aatttgtgaa agattgactg atattcttaa ctatgttgct    3120 cctttacgc tgtgtggata tgctgcttta atgcctctgt atcatgctat tgcttcccgt     3180
acggctttcg ttttctcctc cttgtataaa tcctggttgc tgtctcttta tgaggagttg    3240
tggcccgttg tccgtcaacg tggcgtggtg tgctctgtgt ttgctgacgc aacccccact    3300
ggctggggca ttgccaccac ctgtcaactc cttttctggga ctttcgcttt ccccctcccg   3360
atcgccacgg cagaactcat cgccgcctgc cttgcccgct gctggacagg gctaggttg     3420 ctgggcactg ataattccgt ggtgttgtcg gggaagctga cgtcctttcc atggctgctc    3480
gcctgtgttg ccaactggat cctgcgcggg acgtccttct gctacgtccc ttcggctctc    3540
aatccagcgg acctcccttc ccgaggcctt ctgccggttc tgcggcctct cccgcgtctt    3600
cgctttcggc ctccgacgag tcggatctcc ctttgggccg cctccccgcc tgtttcgcct    3660
cggcgtccgg tccgtgttgc ttggtcgtca cctgtgcaga attgcgaacc atggattcca    3720
ccgtgaactt tgtctcctgg catgcaaatc gtcaacttgg catgccaaga attaattcgg    3780
atccaagctt aggcctgctc gctttcttgc tgtcccattt ctattaaagg ttcctttgtt    3840
ccctaagtcc aactactaaa ctgggggata ttatgaaggg ccttgagcat ctggattctg    3900
cctagcgcta agcttaacac gagccataga tagaataaaa gatttatttt agtctccaga    3960
aaaagggggg aatgaaagac cccacctgta ggtttggcaa gctagcttaa gtaacgccat    4020
tttgcaaggc atggaaaata cataactgag aatagaaag ttcagatcaa ggttaggaac     4080
agagagacag cagaatatgg gccaaacagg atatctgtgg taagcagttc ctgccccggc    4140
tcagggccaa gaacagttgg aacagcagaa tatgggccaa acaggatatc tgtggtaagc    4200
agttcctgcc ccggctcagg gccaagaaca gatggtcccc agatgcggtc cgccctcag    4260 cagtttctag agaaccatca gatgtttcca gggtgcccca aggacctgaa atgaccctgt    4320
gccttatttg aactaaccaa tcagttcgct tctcgcttct gttcgcgcgc ttctgctccc    4380
cgagctcaat aaaagagccc acaaccctc actcggcgcg ccagtcctcc gatagactgc     4440
gtcgcccggg tacccgtgtt ctcaataaac cctcttgcag ttgcatccga ctcgtggtct    4500
cgctgttcct tgggagggtc tcctctgagt gattgactgc ccacctcggg ggtctttcat    4560
tctcgagcag cttggcgtaa tcatggtcat agctgtttcc tgtgtgaaat tgttatccgc    4620
tcacaattcc acacaacata cgagccggaa gcataaagtg taaagcctgg ggtgcctaat    4680
```

```
gagtgagcta actcacatta attgcgttgc gctcactgcc cgctttccag tcgggaaacc    4740
tgtcgtgcca gctgcattaa tgaatcggcc aacgcgcggg gagaggcggt ttgcgtattg    4800
ggcgctcttc cgcttcctcg ctcactgact cgctgcgctc ggtcgttcgg ctgcggcgag    4860
cggtatcagc tcactcaaag gcggtaatac ggttatccac agaatcaggg gataacgcag    4920
gaaagaacat gtgagcaaaa ggccagcaaa aggccaggaa ccgtaaaaag gccgcgttgc    4980
tggcgttttt ccataggctc cgcccccctg acgagcatca caaaaatcga cgctcaagtc    5040
agaggtggcg aaacccgaca ggactataaa gataccaggc gtttccccct ggaagctccc    5100
tcgtgcgctc tcctgttccg accctgccgc ttaccggata cctgtccgcc tttctccctt    5160
cgggaagcgt ggcgctttct catagctcac gctgtaggta tctcagttcg gtgtaggtcg    5220
ttcgctccaa gctgggctgt gtgcacgaac cccccgttca gcccgaccgc tgcgccttat    5280
ccggtaacta tcgtcttgag tccaacccgg taagacacga cttatcgcca ctggcagcag    5340
ccactggtaa caggattagc agagcgaggt atgtaggcgg tgctacagag ttcttgaagt    5400
ggtggcctaa ctacggctac actagaagaa cagtatttgg tatctgcgct ctgctgaagc    5460
cagttacctt cggaaaaaga gttggtagct cttgatccgg caaacaaacc accgctggta    5520
gcggtggttt ttttgtttgc aagcagcaga ttacgcgcag aaaaaaagga tctcaagaag    5580
atcctttgat cttttctacg gggtctgacg ctcagtggaa cgaaaactca cgttaaggga    5640
ttttggtcat gagattatca aaaaggatct tcacctagat ccttttaaat taaaaatgaa    5700
gttttaaatc aatctaaagt atatatgagt aaacttggtc tgacagttac caatgcttaa    5760
tcagtgaggc acctatctca gcgatctgtc tatttcgttc atccatagtt gcctgactcc    5820
ccgtcgtgta gataactacg atacgggagg gcttaccatc tggccccagt gctgcaatga    5880
taccgcgaga cccacgctca ccggctccag atttatcagc aataaaccag ccagccggaa    5940
gggccgagcg cagaagtggt cctgcaactt tatccgcctc catccagtct attaattgtt    6000
gccgggaagc tagagtaagt agttcgccag ttaatagttt gcgcaacgtt gttgccattg    6060
ctacaggcat cgtggtgtca cgctcgtcgt ttggtatggc ttcattcagc tccggttccc    6120
aacgatcaag gcgagttaca tgatccccca tgttgtgcaa aaaagcggtt agctccttcg    6180
gtcctccgat cgttgtcaga agtaagttgg ccgcagtgtt atcactcatg gttatggcag    6240
cactgcataa ttctcttact gtcatgccat ccgtaagatg cttttctgtg actggtgagt    6300
actcaaccaa gtcattctga atagtgtata tgcggcgacc gagttgctct tgcccggcgt    6360
caatacggga taataccgcg ccacatagca gaactttaaa agtgctcatc attggaaaac    6420
gttcttcggg gcgaaaactc tcaaggatct taccgctgtt gagatccagt tcgatgtaac    6480
ccactcgtgc acccaactga tcttcagcat cttttacttt caccagcgtt tctgggtgag    6540
caaaaacagg aaggcaaaat gccgcaaaaa agggaataag ggcgacacgg aaatgttgaa    6600
tactcatact cttcctttt caatattatt gaagcattta tcagggttat tgtctcatga    6660
gcggatacat atttgaatgt atttagaaaa ataaacaaat aggggttccg cgcacatttc    6720
cccgaaaagt gccacctgac gtctaagaaa ccattattat catgacatta acctataaaa    6780
ataggcgtat cacgaggccc tttcgtctcg cgcgtttcgg tgatgacggt gaaaacctct    6840
gacacatgca gctcccggag acggtcacag cttgtctgta agcggatgcc gggagcagac    6900
aagcccgtca gggcgcgtca gcgggtgttg gcgggtgtcg ggctggctt aactatgcgg    6960 catcagagca gattgtactg agagtgcacc atatgcggtg tgaaataccg cacagatgcg    7020
taaggagaaa ataccgcatc aggcgccatt cgccattcag gctgcgcaac tgttgggaag    7080
```

-continued

```
ggcgatcggt gcgggcctct tcgctattac gccagctggc gaaaggggga tgtgctgcaa   7140
ggcgattaag ttgggtaacg ccagggtttt cccagtcacg acgttgtaaa acgacggcca   7200
gtgaattagt actctagctt aagtaacgcc attttgcaag gcatggaaaa tacataactg   7260
agaatagaga agttcaga                                                 7278

<210> SEQ ID NO 21
<211> LENGTH: 7308
<212> TYPE: DNA
<213> ORGANISM: artificial
<220> FEATURE:
<223> OTHER INFORMATION: pMP71-TCR1705mmc

<400> SEQUENCE: 21
tcaaggttag gaacagagag acagcagaat atgggccaaa caggatatct gtggtaagca     60
gttcctgccc cggctcaggg ccaagaacag ttggaacagc agaatatggg ccaaacagga    120
tatctgtggt aagcagttcc tgccccggct cagggccaag aacagatggt ccccagatgc    180
ggtcccgccc tcagcagttt ctagagaacc atcagatgtt tccagggtgc cccaaggacc    240
tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtcctcc agattgattg actgcccacc    480 tcggggtct ttcatttgga ggttccaccg agatttggag accctgccc agggaccacc    540 gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt tgtggcccca ttctgtatca gttaacctac    780
ccgagtcgga cttttttgag ctccgccact gtccgagggg tacgtggctt tgttggggga    840
cgagagacag agacacttcc cgcccccgtc tgaattttg ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccacc atgctgtctc agatctgcc tgacagcgcc tggaacacca   1080
gactgctgtg ccacgtgatg ctgtgcctgc tgggagccgt gtctgtggct gctggcgtga   1140
tccagagccc cagacacctg atcaaagaga agagagagac agccaccctg aagtgctacc   1200
ccatccccag gcacgacacc gtgtactggt atcagcaggg cccaggccag gaccccagt   1260 tcctgatcag cttctacgag aagatgcaga gcgacaaggg cagcatcccc gacagattca   1320
gcgcccagca gttcagcgac taccacagcg agctgaacat gagcagcctg gaactgggcg   1380
acagcgccct gtacttctgc gccagctcct tagaggcgg cggagccaac gtgctgacct   1440
ttggcgctgg cagcagactg accgtgctgg aagacctgaa gaacgtgttc cccccgagg   1500 tggccgtgtt cgagcccagc aaggccgaga tcgcccacac ccagaaagcc acctggtgt   1560 gcctggccac cggcttctac cccgaccacg tggaactgtc ttggtgggtg aacggcaaag   1620
aggtgcacag cggcgtgtgt accgaccccc agccctgaa agagcagcct gccctgaacg   1680
actcccggta ctgcctgagc agccggctga gagtgtccgc caccttctgg cagaaccccc   1740
ggaaccactt cagatgccag gtgcagttct acggcctgag cgagaacgac gagtggaccc   1800
```

```
aggaccgggc caagcccgtg acccagattg tgtctgccga ggcctggggc agagctgatt    1860
gtggcatcac cagcgccagc taccaccagg gcgtgctgag cgccaccatc ctgtacgaga    1920
tcctgctggg caaggccacc ctgtacgccg tgctggtgtc cgccctggtg ctgatggcca    1980
tggtgaaacg gaaggacagc agaggcggca cggcgccac caactttagc ctgctgaaac    2040
aggccggcga cgtggaagag aaccctggcc ccatgatgaa gtccctgcgg gtgctgctcg    2100
tgatcctgtg gctgcagctg agctgggtgt ggtcccagca gaaagaggtg aacaggacc    2160
caggccctct gagcgtgcca gagggcgcta tcgtgtccct gaattgcacc tacagcaaca    2220
gcgccttcca gtacttcatg tggtacagac agtacagccg gaagggcccc gagctgctga    2280
tgtacaccta ctccagcggc aacaaagagg acggccggtt cacagcccag gtggacaaga    2340
gcagcaagta catctccctg ttcatccggg acagccagcc cagcgactct gccacatacc    2400
tgtgcgccat gagcgacacc ggcaaccagt tctacttcgg caccggcacc tccctgaccg    2460
tgatccccaa catccagaac cccgaccccg ccgtgtacca gctgcgggac agcaagagca    2520
gcgacaagag cgtgtgcctg ttcaccgact cgacagcca ccaacgtg tcccagagca    2580
aggacagcga cgtgtacatc accgacaagt gcgtgctgga catgcggagc atggacttca    2640
agagcaactc cgccgtggcc tggtccaaca gagcgactt cgcctgcgcc aacgccttca    2700
acaacagcat catccccgag gacacattct tccccagctc cgacgtgccc tgcgacgtga    2760
agctggtgga aaagagcttc gagacagaca ccaacctgaa cttccagaac ctgagcgtga    2820
tcggcttccg gatcctgctg ctgaaggtgg ctggcttcaa cctgctgatg accctgcggc    2880
tgtggagcag ctgaattcga gcatcttacc gccatttatt cccatatttg ttctgttttt    2940
cttgatttgg gtatacattt aaatgttaat aaaacaaaat ggtgggcaa tcatttacat    3000
tttatgggat atgtaattac tagttcaggt gtattgccac aagacaaaca tgttaagaaa    3060
cttttcccgtt atttacgctc tgttcctgtt aatcaacctc tggattacaa atttgtgaa    3120
agattgactg atattcttaa ctatgttgct ccttttacgc tgtgtggata tgctgcttta    3180
atgcctctgt atcatgctat tgcttcccgt acggctttcg ttttctcctc cttgtataaa    3240
tcctggttgc tgtctctta tgaggagttg tggcccgttg tccgtcaacg tggcgtggtg    3300
tgctctgtgt ttgctgacgc aacccccact ggctggggca ttgccaccac ctgtcaactc    3360
cttttctggga ctttcgcttt cccctcccg atcgccacgg cagaactcat cgccgcctgc    3420
cttgcccgct gctggacagg ggctaggttg ctgggcactg ataattccgt ggtgttgtcg    3480
gggaagctga cgtcctttcc atggctgctc gcctgtgttg ccaactggat cctgcgcggg    3540
acgtccttct gctacgtccc ttcggctctc aatccagcgg acctcccttc ccgaggcctt    3600
ctgccggttc tgcggcctct cccgcgtctt cgctttcggc ctccgacgag tcggatctcc    3660
ctttgggccg cctccccgcc tgtttcgcct cggcgtccgg tccgtgttgc ttggtcgtca    3720
cctgtgcaga attgcgaacc atggattcca ccgtgaactt gtctcctgg catgcaaatc    3780
gtcaacttgg catgccaaga attaattcgg atccaagctt aggcctgctc gctttcttgc    3840
tgtcccattt ctattaaagg ttcctttgtt ccctaagtcc aactactaaa ctggggata    3900
ttatgaaggg ccttgagcat ctggattctg cctagcgcta agcttaacac gagccataga    3960
tagaataaaa gatttatttt agtctccaga aaaagggggg aatgaaagac cccacctgta    4020
ggtttggcaa gctagcttaa gtaacgccat tttgcaaggc atggaaaata cataactgag    4080
aatagagaag ttcagatcaa ggttaggaac agagagacag cagaatatgg gccaaacagg    4140
atatctgtgg taagcagttc ctgccccggc tcagggccaa gaacagttgg aacagcagaa    4200
```

```
tatgggccaa acaggatatc tgtggtaagc agttcctgcc ccggctcagg gccaagaaca    4260
gatggtcccc agatgcggtc ccgccctcag cagtttctag agaaccatca gatgtttcca    4320
gggtgcccca aggacctgaa atgaccctgt gccttatttg aactaaccaa tcagttcgct    4380
tctcgcttct gttcgcgcgc ttctgctccc cgagctcaat aaaagagccc acaacccctc    4440
actcggcgcg ccagtcctcc gatagactgc gtcgcccggg tacccgtgtt ctcaataaac    4500
cctcttgcag ttgcatccga ctcgtggtct cgctgttcct tgggagggtc tcctctgagt    4560
gattgactgc ccacctcggg ggtctttcat tctcgagcag cttggcgtaa tcatggtcat    4620
agctgtttcc tgtgtgaaat tgttatccgc tcacaattcc acacaacata cgagccggaa    4680
gcataaagtg taaagcctgg ggtgcctaat gagtgagcta actcacatta attgcgttgc    4740
gctcactgcc cgctttccag tcgggaaacc tgtcgtgcca gctgcattaa tgaatcggcc    4800
aacgcgcggg gagaggcggt ttgcgtattg ggcgctcttc cgcttcctcg ctcactgact    4860
cgctgcgctc ggtcgttcgg ctgcggcgag cggtatcagc tcactcaaag gcggtaatac    4920
ggttatccac agaatcaggg gataacgcag gaaagaacat gtgagcaaaa ggccagcaaa    4980
aggccaggaa ccgtaaaaag gccgcgttgc tggcgttttt ccataggctc cgcccccctg    5040
acgagcatca caaaaatcga cgctcaagtc agaggtggcg aaacccgaca ggactataaa    5100
gataccaggc gtttccccct ggaagctccc tcgtgcgctc tcctgttccg accctgccgc    5160
ttaccggata cctgtccgcc tttctccctt cgggaagcgt ggcgctttct catagctcac    5220
gctgtaggta tctcagttcg gtgtaggtcg ttcgctccaa gctgggctgt gtgcacgaac    5280
cccccgttca gcccgaccgc tgcgccttat ccggtaacta tcgtcttgag tccaacccgg    5340
taagacacga cttatcgcca ctggcagcag ccactggtaa caggattagc agagcgaggt    5400
atgtaggcgg tgctacagag ttcttgaagt ggtggcctaa ctacggctac actagaagaa    5460
cagtatttgg tatctgcgct ctgctgaagc cagttacctt cggaaaaaga gttggtagct    5520
cttgatccgg caaacaaacc accgctggta gcggtggttt ttttgtttgc aagcagcaga    5580
ttacgcgcag aaaaaaagga tctcaagaag atcctttgat cttttctacg ggtctgacg    5640 ctcagtggaa cgaaaactca cgttaaggga ttttggtcat gagattatca aaaaggatct    5700
tcacctagat ccttttaaat taaaaatgaa gttttaaatc aatctaaagt atatatgagt    5760
aaacttggtc tgacagttac caatgcttaa tcagtgaggc acctatctca gcgatctgtc    5820
tatttcgttc atccatagtt gcctgactcc ccgtcgtgta gataactacg atacgggagg    5880
gcttaccatc tggccccagt gctgcaatga taccgcgaga cccacgctca ccggctccag    5940
atttatcagc aataaaccag ccagccggaa gggccgagcg cagaagtggt cctgcaactt    6000
tatccgcctc catccagtct attaattgtt gccgggaagc tagagtaagt agttcgccag    6060
ttaatagttt gcgcaacgtt gttgccattg ctacaggcat cgtggtgtca cgctcgtcgt    6120
ttggtatggc ttcattcagc tccggttccc aacgatcaag gcgagttaca tgatccccca    6180
tgttgtgcaa aaaagcggtt agctccttcg gtcctccgat cgttgtcaga agtaagttgg    6240
ccgcagtgtt atcactcatg gttatggcag cactgcataa ttctcttact gtcatgccat    6300
ccgtaagatg cttttctgtg actggtgagt actcaaccaa gtcattctga aatagtgta    6360 tgcggcgacc gagttgctct tgcccggcgt caatacggga taataccgcg ccacatagca    6420
gaactttaaa agtgctcatc attggaaaac gttcttcggg gcgaaaactc tcaaggatct    6480
taccgctgtt gagatccagt tcgatgtaac ccactcgtgc acccaactga tcttcagcat    6540
```

```
cttttacttt caccagcgtt tctgggtgag caaaaacagg aaggcaaaat gccgcaaaaa    6600
agggaataag ggcgacacgg aaatgttgaa tactcatact cttcctttt caatattatt    6660
gaagcattta tcagggttat tgtctcatga gcggatacat atttgaatgt atttagaaaa   6720
ataaacaaat aggggttccg cgcacatttc cccgaaaagt gccacctgac gtctaagaaa   6780
ccattattat catgacatta acctataaaa ataggcgtat cacgaggccc tttcgtctcg   6840
cgcgtttcgg tgatgacggt gaaaacctct gacacatgca gctcccggag acggtcacag   6900
cttgtctgta agcggatgcc gggagcagac aagcccgtca gggcgcgtca gcgggtgttg   6960
gcgggtgtcg ggctggctt aactatgcgg catcagagca gattgtactg agagtgcacc    7020
atatgcggtg tgaaataccg cacagatgcg taaggagaaa ataccgcatc aggcgccatt   7080
cgccattcag gctgcgcaac tgttgggaag ggcgatcggt gcgggcctct tcgctattac   7140
gccagctggc gaaaggggga tgtgctgcaa ggcgattaag ttgggtaacg ccagggtttt   7200
cccagtcacg acgttgtaaa acgacggcca gtgaattagt actctagctt aagtaacgcc   7260
attttgcaag gcatggaaaa tacataactg agaatagaga agttcaga                7308
```

<210> SEQ ID NO 22
<211> LENGTH: 275
<212> TYPE: PRT
<213> ORGANISM: Artificial
<220> FEATURE:
<223> OTHER INFORMATION: TCR1367hc - TCRa15

<400> SEQUENCE: 22

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Ile Gly Ser Asn Ser Gly Tyr Ala Leu Asn Phe Gly Lys Gly Thr
        115                 120                 125

Ser Leu Leu Val Thr Pro His Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr

```
                225                 230                 235                 240

Asp Thr Asn Leu Asn Phe Gln Asn Leu Ser Val Ile Gly Phe Arg Ile
                    245                 250                 255

Leu Leu Leu Lys Val Ala Gly Phe Asn Leu Met Thr Leu Arg Leu
                260                 265                 270

Trp Ser Ser
        275

<210> SEQ ID NO 23
<211> LENGTH: 310
<212> TYPE: PRT
<213> ORGANISM: Artificial
<220> FEATURE:
<223> OTHER INFORMATION: TCR1367hc - TCRb3

<400> SEQUENCE: 23

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gly Leu Ala Gly Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
290                 295                 300

Arg Lys Asp Ser Arg Gly
```

-continued

```
         305                 310

<210> SEQ ID NO 24
<211> LENGTH: 275
<212> TYPE: PRT
<213> ORGANISM: Artificial
<220> FEATURE:
<223> OTHER INFORMATION: TCR1367mmc - TCRa15mmc

<400> SEQUENCE: 24

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Ile Gly Ser Asn Ser Gly Tyr Ala Leu Asn Phe Gly Lys Gly Thr
        115                 120                 125

Ser Leu Leu Val Thr Pro His Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Ser Asp Val Pro Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 25
<211> LENGTH: 310
<212> TYPE: PRT
<213> ORGANISM: Artificial
<220> FEATURE:
<223> OTHER INFORMATION: TCR1367mmc - TCRb3mmc

<400> SEQUENCE: 25

Met Gly Ile Arg Leu Leu Cys Arg Val Ala Phe Cys Phe Leu Ala Val
1               5                   10                  15
```

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gly Leu Ala Gly Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Lys Ala Glu Ile Ala His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 26
<211> LENGTH: 273
<212> TYPE: PRT
<213> ORGANISM: Artificial
<220> FEATURE:
<223> OTHER INFORMATION: TCR1405hc - TCRa8

<400> SEQUENCE: 26

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Arg
            100                 105                 110

Pro Asn Ser Gly Asn Thr Pro Leu Val Phe Gly Lys Gly Thr Arg Leu
        115                 120                 125

Ser Val Ile Ala Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 27
<211> LENGTH: 309
<212> TYPE: PRT
<213> ORGANISM: Artificial
<220> FEATURE:
<223> OTHER INFORMATION: TCR1405hc - TCRb4

<400> SEQUENCE: 27

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Gln
            100                 105                 110

Asp Thr Asn Thr Gly Glu Leu Phe Phe Gly Glu Gly Ser Arg Leu Thr
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val

```
            145                 150                 155                 160
    Cys Leu Ala Thr Gly Phe Tyr Pro Asp His Val Glu Leu Ser Trp Trp
                    165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
    225                 230                 235                 240

Gln Asp Arg Ala Lys Pro Val Thr Gln Ile Val Ser Ala Glu Ala Trp
                    245                 250                 255

Gly Arg Ala Asp Cys Gly Phe Thr Ser Glu Ser Tyr Gln Gln Gly Val
                    260                 265                 270

Leu Ser Ala Thr Ile Leu Tyr Glu Ile Leu Leu Gly Lys Ala Thr Leu
                    275                 280                 285

Tyr Ala Val Leu Val Ser Ala Leu Val Leu Met Ala Met Val Lys Arg
                290                 295                 300

Lys Asp Ser Arg Gly
    305

<210> SEQ ID NO 28
    <211> LENGTH: 273
    <212> TYPE: PRT
    <213> ORGANISM: Artificial
    <220> FEATURE:
    <223> OTHER INFORMATION: TCR1405mmc - TCRa8mmc

<400> SEQUENCE: 28

Met Thr Ser Ile Arg Ala Val Phe Ile Phe Leu Trp Leu Gln Leu Asp
    1               5                   10                  15

Leu Val Asn Gly Glu Asn Val Glu Gln His Pro Ser Thr Leu Ser Val
                    20                  25                  30

Gln Glu Gly Asp Ser Ala Val Ile Lys Cys Thr Tyr Ser Asp Ser Ala
                35                  40                  45

Ser Asn Tyr Phe Pro Trp Tyr Lys Gln Glu Leu Gly Lys Gly Pro Gln
                50                  55                  60

Leu Ile Ile Asp Ile Arg Ser Asn Val Gly Glu Lys Lys Asp Gln Arg
    65                  70                  75                  80

Ile Ala Val Thr Leu Asn Lys Thr Ala Lys His Phe Ser Leu His Ile
                    85                  90                  95

Thr Glu Thr Gln Pro Glu Asp Ser Ala Val Tyr Phe Cys Ala Ala Arg
                    100                 105                 110

Pro Asn Ser Gly Asn Thr Pro Leu Val Phe Gly Lys Gly Thr Arg Leu
                115                 120                 125

Ser Val Ile Ala Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
    145                 150                 155                 160

Asp Ser Gln Thr Asn Val Ser Gln Ser Lys Asp Ser Asp Val Tyr Ile
                    165                 170                 175

Thr Asp Lys Cys Val Leu Asp Met Arg Ser Met Asp Phe Lys Ser Asn
                    180                 185                 190

Ser Ala Val Ala Trp Ser Asn Lys Ser Asp Phe Ala Cys Ala Asn Ala
```

195             200             205

Phe Asn Asn Ser Ile Ile Pro Glu Asp Thr Phe Phe Pro Ser Ser Asp
        210                 215                 220

Val Pro Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
        260                 265                 270

Ser

<210> SEQ ID NO 29
<211> LENGTH: 309
<212> TYPE: PRT
<213> ORGANISM: Artificial
<220> FEATURE:
<223> OTHER INFORMATION: TCR1405mmc - TCRb4mmc

<400> SEQUENCE: 29

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Gln
            100                 105                 110

Asp Thr Asn Thr Gly Glu Leu Phe Phe Gly Glu Gly Ser Arg Leu Thr
        115                 120                 125

Val Leu Glu Asp Leu Lys Asn Val Phe Pro Pro Glu Val Ala Val Phe
    130                 135                 140

Glu Pro Ser Lys Ala Glu Ile Ala His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Ser Arg Gly
305

<210> SEQ ID NO 30
<211> LENGTH: 273
<212> TYPE: PRT
<213> ORGANISM: Artificial
<220> FEATURE:
<223> OTHER INFORMATION: TCR1705hc - TCRa2

<400> SEQUENCE: 30

Met Met Lys Ser Leu Arg Val Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Asp Thr Gly Asn Gln Phe Tyr Phe Gly Thr Gly Thr Ser Leu
        115                 120                 125

Thr Val Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 31
<211> LENGTH: 322
<212> TYPE: PRT
<213> ORGANISM: Artificial
<220> FEATURE:
<223> OTHER INFORMATION: TCR1705hc - TCRb13

<400> SEQUENCE: 31

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Phe Arg Gly Gly Gly
        115                 120                 125

Ala Asn Val Leu Thr Phe Gly Ala Gly Ser Arg Leu Thr Val Leu Glu
130                 135                 140

Asp Leu Lys Asn Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
            165                 170                 175

Thr Gly Phe Tyr Pro Asp His Val Glu Leu Ser Trp Trp Val Asn Gly
        180                 185                 190

Lys Glu Val His Ser Gly Val Ser Thr Asp Pro Gln Pro Leu Lys Glu
            195                 200                 205

Gln Pro Ala Leu Asn Asp Ser Arg Tyr Cys Leu Ser Ser Arg Leu Arg
210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
            245                 250                 255

Ala Lys Pro Val Thr Gln Ile Val Ser Ala Glu Ala Trp Gly Arg Ala
        260                 265                 270

Asp Cys Gly Phe Thr Ser Glu Ser Tyr Gln Gln Gly Val Leu Ser Ala
            275                 280                 285

Thr Ile Leu Tyr Glu Ile Leu Leu Gly Lys Ala Thr Leu Tyr Ala Val
        290                 295                 300

Leu Val Ser Ala Leu Val Leu Met Ala Met Val Lys Arg Lys Asp Ser
305                 310                 315                 320

Arg Gly

<210> SEQ ID NO 32
<211> LENGTH: 273
<212> TYPE: PRT
<213> ORGANISM: Artificial
<220> FEATURE:
<223> OTHER INFORMATION: TCR1705mmc - TCRa2mmc

<400> SEQUENCE: 32

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

-continued

```
Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
 50                  55                  60

Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
                 85                  90                  95

Phe Ile Arg Asp Ser Gln Pro Ser Asp Ser Ala Thr Tyr Leu Cys Ala
            100                 105                 110

Met Ser Asp Thr Gly Asn Gln Phe Tyr Phe Gly Thr Gly Thr Ser Leu
            115                 120                 125

Thr Val Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Ser Asp
    210                 215                 220

Val Pro Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 33
<211> LENGTH: 322
<212> TYPE: PRT
<213> ORGANISM: Artificial
<220> FEATURE:
<223> OTHER INFORMATION: TCR1705mmc - TCRb13mmc

<400> SEQUENCE: 33

Met Leu Ser Pro Asp Leu Pro Asp Ser Ala Trp Asn Thr Arg Leu Leu
 1               5                  10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                 85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Phe Arg Gly Gly Gly
```

```
                    115                 120                 125
Ala Asn Val Leu Thr Phe Gly Ala Gly Ser Arg Leu Thr Val Leu Glu
    130                 135                 140

Asp Leu Lys Asn Val Phe Pro Pro Glu Val Ala Val Phe Glu Pro Ser
145                 150                 155                 160

Lys Ala Glu Ile Ala His Thr Gln Lys Ala Thr Leu Val Cys Leu Ala
                165                 170                 175

Thr Gly Phe Tyr Pro Asp His Val Glu Leu Ser Trp Trp Val Asn Gly
            180                 185                 190

Lys Glu Val His Ser Gly Val Cys Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Ile Thr Ser Ala Ser Tyr His Gln Gly Val Leu Ser Ala
        275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Ser
305                 310                 315                 320

Arg Gly

<210> SEQ ID NO 34
<211> LENGTH: 271
<212> TYPE: PRT
<213> ORGANISM: Artificial
<220> FEATURE:
<223> OTHER INFORMATION: 1367_mc - TCRa15mc

<400> SEQUENCE: 34

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Ile Gly Ser Asn Ser Gly Tyr Ala Leu Asn Phe Gly Lys Gly Thr
        115                 120                 125

Ser Leu Leu Val Thr Pro His Ile Gln Asn Pro Glu Pro Ala Val Tyr
130                 135                 140

Gln Leu Lys Asp Pro Arg Ser Gln Asp Ser Thr Leu Cys Leu Phe Thr
145                 150                 155                 160
```

Asp Phe Asp Ser Gln Ile Asn Val Pro Lys Thr Met Glu Ser Gly Thr
            165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
            210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
            245                 250                 255

Val Ala Gly Phe Asn Leu Leu Met Thr Leu Arg Leu Trp Ser Ser
            260                 265                 270

<210> SEQ ID NO 35
<211> LENGTH: 304
<212> TYPE: PRT
<213> ORGANISM: Artificial
<220> FEATURE:
<223> OTHER INFORMATION: 1367_mc - TCRb3mc

<400> SEQUENCE: 35

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
            100                 105                 110

Arg Gly Leu Ala Gly Tyr Glu Gln Tyr Phe Gly Pro Gly Thr Arg Leu
            115                 120                 125

Thr Val Thr Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
            165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
            210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
            245                 250                 255

```
Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Gly Leu Val Leu Met Ala Met Val Lys Lys Lys Asn Ser
            290                 295                 300

<210> SEQ ID NO 36
<211> LENGTH: 269
<212> TYPE: PRT
<213> ORGANISM: Artificial
<220> FEATURE:
<223> OTHER INFORMATION: 1405_mc - TCRa8mc

<400> SEQUENCE: 36

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Arg
            100                 105                 110

Pro Asn Ser Gly Asn Thr Pro Leu Val Phe Gly Lys Gly Thr Arg Leu
        115                 120                 125

Ser Val Ile Ala Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 37
<211> LENGTH: 303
<212> TYPE: PRT
<213> ORGANISM: Artificial
<220> FEATURE:
<223> OTHER INFORMATION: 1405_mc - TCRb4mc
```

<400> SEQUENCE: 37

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
                35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Glu Gln
            100                 105                 110

Asp Thr Asn Thr Gly Glu Leu Phe Phe Gly Glu Gly Ser Arg Leu Thr
            115                 120                 125

Val Leu Glu Asp Leu Arg Asn Val Thr Pro Pro Lys Val Ser Leu Phe
130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Gly Leu Val Leu Met Ala Met Val Lys Lys Lys Asn Ser
290                 295                 300

<210> SEQ ID NO 38
<211> LENGTH: 269
<212> TYPE: PRT
<213> ORGANISM: Artificial
<220> FEATURE:
<223> OTHER INFORMATION: 1705_mc - TCRa2mc

<400> SEQUENCE: 38

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys

```
                    50                  55                  60
Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
                 85                  90                  95

Phe Ile Arg Asp Ser Gln Pro Ser Asp Ser Ala Thr Tyr Leu Cys Ala
            100                 105                 110

Met Ser Asp Thr Gly Asn Gln Phe Tyr Phe Gly Thr Gly Thr Ser Leu
            115                 120                 125

Thr Val Ile Pro Asn Ile Gln Asn Pro Glu Pro Ala Val Tyr Gln Leu
            130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 39
<211> LENGTH: 316
<212> TYPE: PRT
<213> ORGANISM: Artificial
<220> FEATURE:
<223> OTHER INFORMATION: 1705_mc - TCRb13mc

<400> SEQUENCE: 39

Met Leu Ser Pro Asp Leu Pro Asp Ser Ala Trp Asn Thr Arg Leu Leu
 1               5                  10                  15

Cys His Val Met Leu Cys Leu Leu Gly Ala Val Ser Val Ala Ala Gly
                 20                  25                  30

Val Ile Gln Ser Pro Arg His Leu Ile Lys Glu Lys Arg Glu Thr Ala
             35                  40                  45

Thr Leu Lys Cys Tyr Pro Ile Pro Arg His Asp Thr Val Tyr Trp Tyr
         50                  55                  60

Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                 85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Phe Arg Gly Gly Gly
            115                 120                 125

Ala Asn Val Leu Thr Phe Gly Ala Gly Ser Arg Leu Thr Val Leu Glu
            130                 135                 140

Asp Leu Arg Asn Val Thr Pro Pro Lys Val Ser Leu Phe Glu Pro Ser
```

```
            145                 150                 155                 160
Lys Ala Glu Ile Ala Asn Lys Gln Lys Ala Thr Leu Val Cys Leu Ala
                165                 170                 175
Arg Gly Phe Phe Pro Asp His Val Glu Leu Ser Trp Trp Val Asn Gly
            180                 185                 190
Lys Glu Val His Ser Gly Val Ser Thr Asp Pro Gln Ala Tyr Lys Glu
        195                 200                 205
Ser Asn Tyr Ser Tyr Cys Leu Ser Ser Arg Leu Arg Val Ser Ala Thr
    210                 215                 220
Phe Trp His Asn Pro Arg Asn His Phe Arg Cys Gln Val Gln Phe His
225                 230                 235                 240
Gly Leu Ser Glu Glu Asp Lys Trp Pro Glu Gly Ser Pro Lys Pro Val
                245                 250                 255
Thr Gln Asn Ile Ser Ala Glu Ala Trp Gly Arg Ala Asp Cys Gly Ile
            260                 265                 270
Thr Ser Ala Ser Tyr His Gln Gly Val Leu Ser Ala Thr Ile Leu Tyr
        275                 280                 285
Glu Ile Leu Leu Gly Lys Ala Thr Leu Tyr Ala Val Leu Val Ser Gly
    290                 295                 300
Leu Val Leu Met Ala Met Val Lys Lys Lys Asn Ser
305                 310                 315

<210> SEQ ID NO 40
<211> LENGTH: 6
<212> TYPE: PRT
<213> ORGANISM: Homo sapiens

<400> SEQUENCE: 40

Asp Ser Ser Ser Thr Tyr
1               5

<210> SEQ ID NO 41
<211> LENGTH: 7
<212> TYPE: PRT
<213> ORGANISM: Homo sapiens

<400> SEQUENCE: 41

Ile Phe Ser Asn Met Asp Met
1               5

<210> SEQ ID NO 42
<211> LENGTH: 6
<212> TYPE: PRT
<213> ORGANISM: Homo sapiens

<400> SEQUENCE: 42

Asp Ser Ala Ser Asn Tyr
1               5

<210> SEQ ID NO 43
<211> LENGTH: 7
<212> TYPE: PRT
<213> ORGANISM: Homo sapiens

<400> SEQUENCE: 43

Ile Arg Ser Asn Val Gly Glu
1               5

<210> SEQ ID NO 44
<211> LENGTH: 6
```

```
<212> TYPE: PRT
<213> ORGANISM: Homo sapiens

<400> SEQUENCE: 44

Asn Ser Ala Phe Gln Tyr
1               5

<210> SEQ ID NO 45
<211> LENGTH: 6
<212> TYPE: PRT
<213> ORGANISM: Homo sapiens

<400> SEQUENCE: 45

Thr Tyr Ser Ser Gly Asn
1               5

<210> SEQ ID NO 46
<211> LENGTH: 5
<212> TYPE: PRT
<213> ORGANISM: Homo sapiens

<400> SEQUENCE: 46

Met Asp His Glu Asn
1               5

<210> SEQ ID NO 47
<211> LENGTH: 6
<212> TYPE: PRT
<213> ORGANISM: Homo sapiens

<400> SEQUENCE: 47

Ser Tyr Asp Val Lys Met
1               5

<210> SEQ ID NO 48
<211> LENGTH: 5
<212> TYPE: PRT
<213> ORGANISM: Homo sapiens

<400> SEQUENCE: 48

Ser Gln Val Thr Met
1               5

<210> SEQ ID NO 49
<211> LENGTH: 7
<212> TYPE: PRT
<213> ORGANISM: Homo sapiens

<400> SEQUENCE: 49

Ala Asn Gln Gly Ser Glu Ala
1               5

<210> SEQ ID NO 50
<211> LENGTH: 5
<212> TYPE: PRT
<213> ORGANISM: Homo sapiens

<400> SEQUENCE: 50

Pro Arg His Asp Thr
1               5
```

```
<210> SEQ ID NO 51
<211> LENGTH: 6
<212> TYPE: PRT
<213> ORGANISM: Homo sapiens

<400> SEQUENCE: 51

Phe Tyr Glu Lys Met Gln
1               5

<210> SEQ ID NO 52
<211> LENGTH: 31
<212> TYPE: PRT
<213> ORGANISM: Homo sapiens

<400> SEQUENCE: 52

Ala Leu Ala Glu Thr Ser Tyr Val Lys Val Leu Glu Tyr Val Ile Lys
1               5                   10                  15

Val Ser Ala Arg Val Arg Phe Phe Pro Ser Leu Arg Glu Ala
            20                  25                  30

<210> SEQ ID NO 53
<211> LENGTH: 31
<212> TYPE: PRT
<213> ORGANISM: Mus musculus

<400> SEQUENCE: 53

Ala Phe Ala Glu Thr Ser Lys Met Lys Val Leu Gln Phe Phe Ala Ser
1               5                   10                  15

Ile Asn Lys Thr His Pro Arg Ala Tyr Pro Glu Lys Tyr Ala Glu
            20                  25                  30

<210> SEQ ID NO 54
<211> LENGTH: 9
<212> TYPE: PRT
<213> ORGANISM: Homo sapiens

<400> SEQUENCE: 54

Lys Val Leu Glu Phe Val Ala Lys Val
1               5

<210> SEQ ID NO 55
<211> LENGTH: 9
<212> TYPE: PRT
<213> ORGANISM: Homo sapiens

<400> SEQUENCE: 55

Lys Val Leu Glu Tyr Leu Ala Lys Val
1               5
```

HIGH AVIDITY ANTIGEN RECOGNIZING CONSTRUCTS

CROSS REFERENCE TO RELATED APPLICATIONS

This application is a National Stage Application of International Application Number PCT/EP2014/051726, filed Jan. 29, 2014; which claims priority to European Application No. 13153081.8, filed Jan. 29, 2013; both of which are incorporated herein by reference in their entirety.

The Sequence Listing for this application is labeled "SeqList-15Feb17-ST25.txt, which was created on Feb. 15,2017, and is 135 KB. The entire content is incorporated herein by reference in its entirety.

FIELD OF THE INVENTION

The present invention pertains to novel high avidity antigen recognizing constructs, such as antibodies or T cell receptors, which specifically bind to the melanoma associated antigen (MAGE) A1. The constructs of the invention are particularly useful for the diagnosis, prevention or therapy of tumorous diseases which are characterized by the specific expression of the MAGE-A1 antigen. Furthermore provided are nucleic acids, vectors and host cells—such as CD4 or CD8 positive T cells—which encode, comprise or present the antigen recognizing constructs of the invention. The invention thus provides new means for immune therapy, specifically adoptive T cell therapy, for treating cancer.

DESCRIPTION

Despite remarkable technological advancements in the diagnosis and treatment options available to patients diagnosed with cancer, the prognosis still often remains poor and many patients cannot be cured. Immunotherapy holds the promise of offering a potent, yet targeted, treatment to patients diagnosed with various tumors, with the potential to eradicate the malignant tumor cells without damaging normal tissues. In theory the T cells of the immune system are capable of recognizing protein patterns specific for tumor cells and to mediate their destruction through a variety of effector mechanisms. Adoptive T-cell therapy is an attempt to harness and amplify the tumor-eradicating capacity of a patient's own T cells and then return these effectors to the patient in such a state that they effectively eliminate residual tumor, however without damaging healthy tissue. Although this approach is not new to the field of tumor immunology, still many drawbacks in the clinical use of adoptive T cell therapy impair the full use of this approach in cancer treatments.

Figure 1:
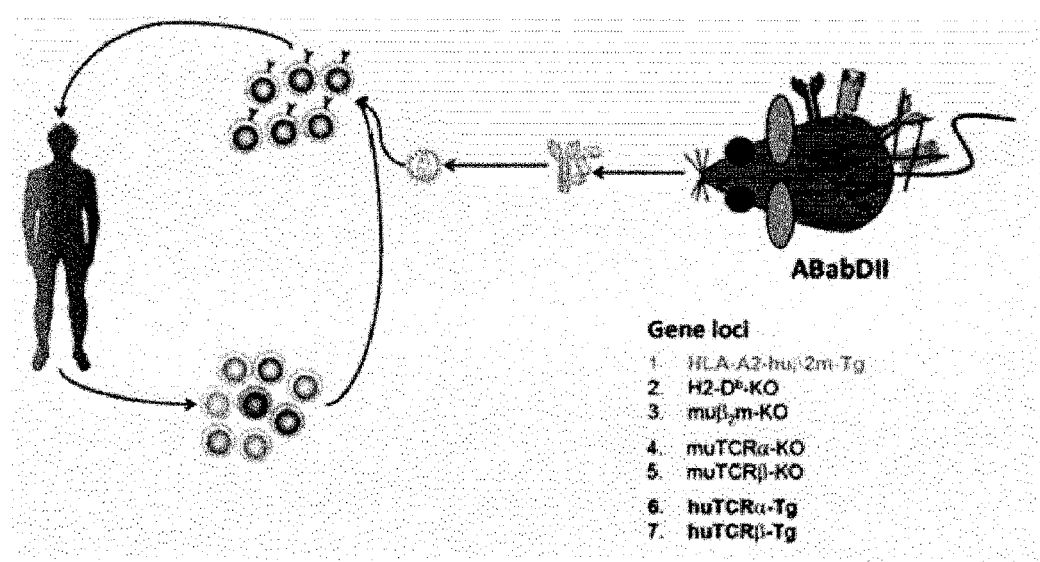

A TCR is a heterodimeric cell surface protein of the immunoglobulin super-family which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR consists of two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression. Transgenic mice expressing human MHC molecules and a diverse human TCR repertoire serve as a tool to rapidly analyze whether peptide antigens are immunogenic, i.e. are they efficiently processed and presented by MHC molecules, do they efficiently induce T cell responses following immunization (Li et al. 2010 Nat Med). The concept of adoptive T cell therapy using the ABabDII mouse published by Li et al is shown in FIG. 1.

In brief, CD8+ T cells in ABabDII mice harbor human T cell receptors (TCRs) which recognize antigens presented by human MHC class I molecules. As opposed to humans, ABabDII mice are not tolerant to human tumor associated antigens (TAAs). Therefore, when vaccinated with a human TAA, ABabDII mice generate an efficient adaptive immune response against those foreign antigens including the expansion of high avidity antigen specific T cells (FIG. 1, right side). After immunization with a suitable human TAA the genetic information coding for the high avidity TCRs of the ABabDII mice can be extracted (FIG. 1, center). These TCRs can subsequently be re-expressed in T cells from tumor patients through retroviral transduction. Those re-targeted T cells can be transferred back into the patient fighting the tumor (FIG. 1, left side).

Using the human TCR transgenic mouse, any human peptide sequence not encoded by the mouse genome is thus suitable for immunization and will yield TCRs with optimal affinity. Optimal affinity means that the T cells are restricted to human self-MHC molecules and recognize the peptide antigen as foreign, e.g. represent the non-tolerant repertoire. By using peptide/MHC multimers, specific T cells of the transgenic mice can be sorted, human TCRs isolated, e.g. by single cell PCR, the TCRs optimized for efficient expression while avoiding mispairing with endogenous TCR and used for transduction of patients' T cells with viral vectors (Uckert et al. 2008 Cancer Immunol Immunother; Kammertoens T et al. 2009 Eur J Im-munol).

The melanoma antigen genes (MAGE-A) were found to be expressed in a variety of tumors of different histological origin. Proteins encoded by the MAGE genes are tumor rejection antigens, which can induce specific cytotoxic T-lymphocytes (CTL) having the ability to recognize and kill cancerous cells. MAGE genes and proteins are thus a preferential target for the development of novel drugs to fight cancer by immunotherapy. MAGE-A proteins constitute a sub-family of Cancer-Testis Antigens which are expressed mainly, but not exclusively, in the germ line. They are however also expressed in various human cancers where they are associated with, and may drive, malignancy. This specific expression of MAGE antigens in tumors and not the normal surrounding healthy tissue makes this family of antigens very interesting for targeted adoptive T cell transfer. However, to date no satisfactory immune therapy is known due to the lack of specific and highly avid antibodies or T cell receptors targeting the MAGE antigen.

In view of the above described major drawbacks in the background art, it is the objective of the present invention to provide new antigen recognizing constructs with high avidity and specificity against the MAGE-A antigen. Furthermore, the present invention intends to provide novel methods that allow for the production of such constructs. In more general terms the invention seeks to provide novel means for immuno cancer therapy.

The above problem is solved in a first aspect by an antigen recognizing construct comprising an amino acid sequence having at least 50%, 60%, 70%, 80%, 90%, 95%, 98%, 99% or 100% sequence identity to an amino acid sequence selected from SEQ ID Nos. 1 to 6. SEQ ID No 1 to 6 corresponds to CDR3 regions shown in FIG. 4 of this application. It was surprisingly discovered that the TCRs provided in the examples of the present invention are highly avid compared to state of the art TCRs directed at MAGE antigens. In one preferred embodiment of the present invention the antigen recognizing construct comprises a complementary determining region 3 (CDR3) having at least 50%, 60%, 70%, 80%, 90%, 95%, 98%, 99% or 100% sequence identity to an amino acid sequence selected from SEQ ID Nos. 1 to 6.

Preferred in the context of the invention is also that the antigen recognizing construct further comprises a V element selected from TRAV5, TRAV13-1, TRAV12-3, TRBV28, TRBV29-1, TRBV13, TRBV20, TRBV12, and/or a J element selected from TRAJ41, TRAJ29, TRAJ31, TRAJ49, TRAJ34, TRBJ2-7, TRBJ2-2, TRBJ2-6, TRBJ7, TRBJ1-2; preferably in the combination as depicted in table 1.

The antigen recognizing construct in accordance with the invention is specific for and/or binds specifically to an antigen of the melanoma associated antigen MAGE family. Various proteins are known to be part of the MAGE family which includes also some pseudo genes. One region of homology shared by all of the members of the MAGE family is a stretch of about 200 amino acids which has been named the MAGE conserved domain. The MAGE conserved domain is usually located close to the C-terminal, although it can also be found in a more central position in some proteins. The MAGE conserved domain is generally present as a single copy but it is duplicated in some proteins. MAGE genes which are detectable by the antigen recognizing constructs of the invention are selected from MAGE-B1, MAGE-A1, MAGE-A10, MAGE-A11, MAGE-A12, MAGE-A2B, MAGE-A3, MAGE-A4, MAGE-A6, MAGE-A8, MAGE-A9, MAGE-B1, MAGE-B10, MAGE-B16, MAGE-B18, MAGE-B2, MAGE-B3, MAGE-B4, MAGE-B5, MAGE-B6, MAGE-B6B, MAGE-C1, MAGE-C2, MAGE-C3, MAGE-D1, MAGE-D2, MAGE-D4, MAGE-E1, MAGE-E2, MAGE-F1, MAGE-H1, MAGE-L2, NDN, NDNL2. Preferred in the context of the present invention are the 12 homologous MAGE proteins selected from MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12. Most preferred is an antigen recognizing construct having specificity for MAGE-A1.

The term "specificity" or "antigen specificity" or "specific for" a given antigen, as used herein means that the antigen recognizing construct can specifically bind to and immunologically recognize said antigen, preferably MAGE-A1, more preferably with high avidity. For example, a TCR may be considered to have "antigenic specificity" for MAGE-A1 if T cells expressing the TCR secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a MAGE peptide, such as the MAGE-A1 HLA-A02 restricted MAGE-A1$_{278-286}$ peptide (e.g., about $10^{-11}$ mol/l, $10^{-10}$ mol/l, $10^{-9}$ mol/l, $10^{-8}$ mol/l, $10^{-7}$ mol/l, $10^{-6}$ mol/l, $10^{-5}$ mol/l). Alternatively or additionally, a TCR may be considered to have "antigenic specificity" for MAGE-A1 if T cells expressing the TCR secrete at least twice as much IFN-γ as the untransduced background level of IFN-γ upon co-culture with target cells pulsed with a low concentration of HLA-A02 restricted MAGE-A1. Such a "specificity" as described above can—for example—be analyzed with an ELISA.

Preferred embodiments of the present invention disclose antigen recognizing constructs which are in the form of an antibody, or derivative or fragment thereof, or a T cell receptor (TCR), or derivative or fragment thereof. Fragments or derivatives of the herein disclosed antibodies or TCRs preferably still harbor the antigenic specificity (the binding function with respect to the antigen) as the original antibody or TCR, respectively.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number.

Thus, a further embodiment of the present invention pertains to an ARC comprising an alpha chain variable region, wherein said alpha chain variable region comprises a CDR1, CDR2 and CDR3 that comprise an amino acid sequence that is at least 50%, 60%, 70%, 80%, 90%, 95%, 98%, 99% or preferably 100% identical to the amino acid sequence of the corresponding CDR1 and CDR2 of the Vα-type TRAV5 (according to IMGT nomenclature) and CDR3: CAESIGSNSGYALNF (SEQ ID NO: 1 );or a CDR1 and CDR2 of the Vα-type TRAV13-1 and CDR3: CAARPNSGNTPLVF (SEQ ID NO:2); or a CDR1 and CDR2 of the Vα-type TRAV12-3 and CAMSDTGNQFYF (SEQ ID NO:3). Another embodiment of the present invention pertains to an ARC comprising a beta chain variable region, wherein said beta chain variable region comprises a CDR1, CDR2 and CDR3 that comprise an amino acid sequence that is at least 50%, 60%, 70%, 80%, 90%, 95%, 98%, 99% or preferably 100% identical to the respective amino acid sequence of a CDR1 and CDR2 of the Vβ-type TRBV28 (according to IMGT nomenclature) and CDR3: CASRGLAGYEQYF (SEQ ID NO:4; or a CDR1 and CDR2 of the Vβ-type TRBV29-1 and CDR3: CSVEQDTNTGELFF (SEQ ID NO:4); or a CDR1and CDR2 of the Vβ-type TRBV13 and the CDR3: CASSFRGGGANVLTF (SEQ ID NO:6).

In one preferred embodiment the aforementioned ARC comprises an alpha chain and beta chain with the above referenced variable regions, preferably in the combination as indicated in table 1 below.

Preferred are ARCs of the invention which comprise at least one, preferably all three CDR sequences CDR1, CDR2 and CDR3. ARCs of the invention may comprise:

CDR 1 and CDR2 regions of the respective known Vα and Vβ types are according to the IMGT database:

TRAV5: CDR1: DSSSTY, (SEQ ID NO: 40)

CDR2: IFSNMDM (SEQ ID NO: 41)

TRAV13-1 CDR1: DSASNY, (SEQ ID NO: 42)

CDR2: IRSNVGE (SEQ ID NO: 43)

TRAV12-3 CDR1: NSAFQY, (SEQ ID NO: 44)

CDR2: TYSSGN (SEQ ID NO: 45)

TRBV28: CDR1: MDHEN, (SEQ ID NO: 46)

CDR2: SYDVKM. (SEQ ID NO: 47)

TRBV29-1: CDR1: SQVTM, (SEQ ID NO: 48)

CDR2: ANQGSEA (SEQ ID NO: 49)

TRBV13: CDR1: PRHDT, (SEQ ID NO: 50)

CDR2: FYEKMQ. (SEQ ID NO: 51)

Therefore, an ARC of the invention in a preferred embodiment comprises an alpha chain comprising the CDR sequences shown in SEQ ID NO: 40, 41 and 1; or SEQ ID NO: 42, 43, and 2; or SEQ ID NO: 44, 45, and 3. Alternatively or additionally the ARC of the invention comprises a beta chain having the sequences shown in SEQ ID NO: 46, 47, and 4; or SEQ OD NO: 48, 49, and 5; or SEQ ID NO: 50, 51, and 6.

Preferred according to the invention is a TCR or an antibody, or their respective antigenic binding fragments, with
a. an alpha chain comprising the CDR sequences shown in SEQ ID NO: 40, 41, and 1; and a beta chain comprising the CDR sequences shown in SEQ ID NO: 46, 47, and 4; or
b. an alpha chain comprising the CDR sequences shown in SEQ ID NO: 42, 43, and 2; and a beta chain comprising the CDR sequences shown in SEQ ID NO: 48, 49, and 5; or
c. an alpha chain comprising the CDR sequences shown in SEQ ID NO: 44, 45, and 3; and a beta chain comprising the CDR sequences shown in SEQ ID NO: 50, 51, and 6.

The ARC is in preferred embodiments selected from an antibody or a TCR, but TCRs are preferred.

For the purposes of the present invention, a TCR is a moiety having at least one TCR alpha and/or TCR beta variable domain. Generally they comprise both a TCR alpha variable domain and a TCR beta variable domain. They may be αβ heterodimers or may be single chain format. For use in adoptive therapy, an αβ heterodimeric TCR may, for example, be transfected as full length chains having both cytoplasmic and transmembrane domains. If desired, an introduced disulfide bond between residues of the respective constant domains may be present.

In one preferred embodiment of the first aspect of the invention, the antigen recognizing construct is as described above a TCR. The TCR preferably comprises at least one alpha and/or beta TCR chain, wherein said TCR chain is encoded by at least one nucleic acid, the nucleic acid comprising a nucleotide sequence selected from (i) the TCR chain encoding sequences comprised in SEQ ID No. 13 to 21, or (ii) a sequence having at least 50%, 60%, 70%, 80%, 90%, 95%, 98%, 99% or 100% identity to a TCR encoding sequence comprised in SEQ ID No. 13 to 21, or (iii) a sequence that due to the degeneracy of the genetic code encodes for an identical TCR as any one of the TCR en-coding sequences comprised in SEQ ID No. 13 to 21, but has a different sequence.

SEQ ID Nos. 13 to 21 depict the nucleotide sequences of the vector maps of FIGS. 8 to 16. Each of these vectors comprise an alpha and a beta chain of a TCR of the present invention. In the figures the beta chain is located upstream of the alpha chain sequence. As also described below, the invention exemplary describes three isolated TCRs, which were to different degrees optimized by murinization of the original sequence of the constant domain of the TCR chains. The abbreviation in the vector designation "hc" stands for the complete human variant of the TCR, "mc" for a complete murinized constant domain in the TCR chain, whereas "mmc" depicts minimal murinization in the constant domain of the TCR chain. The exact location of the alpha and beta chains in the vector maps (and thus in the corresponding sequences) can be derived from the figure legend.

In one preferred embodiment of alternative (i) as described before, the TCR comprises the alpha and beta chain sequence as comprised together in any one of SEQ ID No. 13 to 21.

In one additional preferred embodiment of the first aspect of the invention, the antigen recognizing construct is as described above a TCR. The TCR preferably comprises at least one alpha and/or beta TCR chain, wherein said TCR chain comprises an amino acid sequence according to any one of the TCR chains shown in SEQ ID Nos. 22 -39, or an amino acid sequence having at least 50%, 60%, 70%, 80%, 90%, 95%, 98%, 99% or 100% identity to an amino acid sequence shown in SEQ ID No. 22 to 39.

An scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide which joins together two single chains, as described herein.

Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, and wherein said scTCRs are interconnected by biotin-strepavidin interaction to allow the formation of said multimeric complex. Also provided are multimeric complexes of a higher order, comprising more than two scTCR of the invention.

In one embodiment the antigen recognizing construct according to the invention is an antibody, or a fragment thereof. The term "antibody" in its various grammatical forms is used herein to refer to immunoglobulin molecules and immunologically active portions of immunoglobulin molecules, i.e., molecules that contain an antibody combining site or a paratope. Such molecules are also referred to as "antigen binding fragments" of immunoglobulin molecules.

The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The invention also provides antigen binding portions of any of the antibodies described herein. The antigen binding portion can be any portion that has at least one antigen binding site, such as Fab, F(ab')2, dsFv, sFv, diabodies, and triabodies. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

In an embodiment of the invention the antigen recognizing construct binds to a human leucocyte antigen (HLA) presented peptide, preferably by HLA-A02, of MAGE. In a preferred embodiment the antigen recognizing construct specifically binds to the human MAGE-A1$_{278-286}$ epitope.

In a preferred embodiment the antigen recognizing construct is a human TCR, or fragment or derivative thereof. A human TCR or fragment or derivative thereof is a TCR which comprises over 50% of the corresponding human TCR sequence. Preferably only a small part of the TCR sequence is of artificial origin or derived from other species. It is known however, that chimeric TCRs e.g. from human origin with murine sequences in the constant domains, are advantageous. Particularly preferred are therefore TCRs in accordance with the present invention, which contain murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by HLA.

The antigen recognizing construct in accordance with the invention in one embodiment preferably induces an immune response, preferably wherein the immune response is characterized by the increase in interferon (IFN) γ levels.

Figure 4:
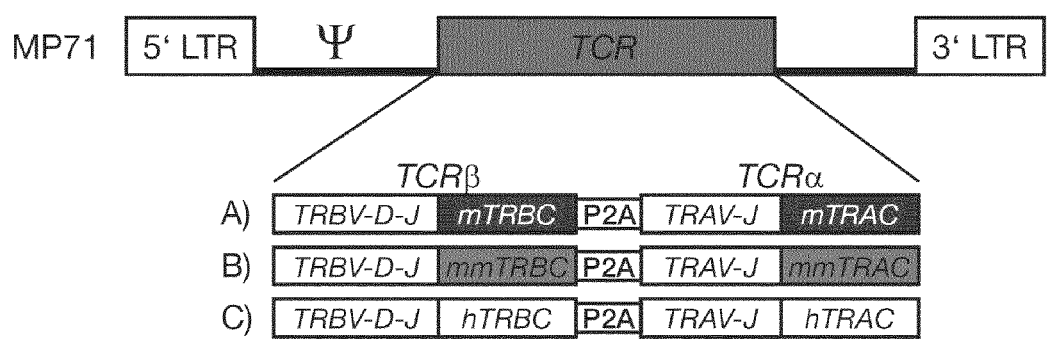

A preferred embodiment of the invention pertains to the antigen recognizing construct which is a T cell receptor, and which comprises in its alpha chain a CDR3 having at least 50%, 60%, 70%, 80%, 90%, 95%, 98%, 99% or 100% sequence identity to an amino acid sequence selected from SEQ ID Nos. 1 to 3, and/or comprises in its beta chain an CDR3 having at least 50%, 60%, 70%, 80%, 90%, 95%, 98%, 99% or 100% sequence identity to an amino acid sequence selected from SEQ ID Nos. 4 to 6. Further preferred is a TCR wherein the alpha chain comprises an CDR3 having at least 50%, 60%, 70%, 80%, 90%, 95%, 98%, 99% or 100% sequence identity to SEQ ID No. 1, and the beta chain comprises an CDR3 having at least 50%, 60%, 70%, 80%, 90%, 95%, 98%, 99% or 100% sequence identity to SEQ ID No. 4; or wherein the alpha chain comprises an CDR3 having at least 50%, 60%, 70%, 80%, 90%, 95%, 98%, 99% or 100% sequence identity to SEQ ID No. 2, and the beta chain comprises an CDR3 having at least 50%, 60%, 70%, 80%, 90%, 95%, 98%, 99% or 100% sequence identity to SEQ ID No. 5; or wherein the alpha chain comprises an CDR3 having at least 50%, 60%, 70%, 80%, 90%, 95%, 98%, 99% or 100% sequence identity to SEQ ID No. 3, and the beta chain comprises an CDR3 having at least 50%, 60%, 70%, 80%, 90%, 95%, 98%, 99% or 100% sequence identity to SEQ ID No. 6. Preferably, the CDR3 regions are combined with a CDJ element as depicted in any of the figures, in particular in the combination as shown in FIG. 4.

Furthermore preferred is that the antigen recognizing construct of the invention, which is a T cell receptor, comprises an amino acid sequence having at least 50%, 60%, 70%, 80%, 90%, 95%, 98%, 99% or 100% sequence identity to an amino acid sequence shown in SEQ ID No. 22 to 39. Particularly preferred are TCRs having at least 50%, 60%, 70%, 80%, 90%, 95%, 98%, 99% or 100% sequence identity to a TCR selected from TCR1367hc, TCR1367mc, TCR1367mmc, TCR1405hc, TCR1405mc, TCR1405mmc, TCR1705hc, TCR1705mc an TCR1705mmc. Most preferred is a TCR selected from the group consisting of TCR1367hc, TCR1367mc, TCR1367mmc, TCR1405hc, TCR1405mc, TCR1405mmc, TCR1705hc, TCR1705mc an TCR1705mmc. The amino acid sequences of the above referenced TCRs of the invention are depicted in SEQ ID No. 22 to 39.

The antigen recognizing construct in accordance with the invention are high avidity TCRs.

The problem of the invention is solved in another aspect by providing a nucleic acid encoding for an antigen recognizing construct in accordance with the present invention. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform a presenting cell, which shall not be restricted to classical antigen-presenting cells such as dendritic cells, in such a way that they themselves produce the corresponding proteins on their cellular surface.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "re-combinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-C1, pMAM and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal) into which the vector is to be introduced and in which the expression of the nucleic acid of the invention shall be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence which is complementary to or which hybridizes to the nucleotide sequence encoding the constructs of the invention. The selection of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precurser from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4positive and/or CD8positive, CD4 positive helper T cells, e.g., Th1 and Th2 cells, CD8 positive T cells (e.g., cytotoxic T cells), tumor infiltrating cells (TILS), memory T cells, naive T cells, and the like. Preferably, the T cell is a CD8 positive T cell or a CD4 positive T cell.

Preferably, the host cell of the invention is a lymphocyte, preferably a T lymphocyte, such as a CD4 or CD8 positive T-cell. The host cell furthermore preferably is a tumor reactive T cell specific for MAGE-A1 expressing tumor cells.

One further aspect of the present invention relates to the herein disclosed antigen recognizing constructs, nucleic acids, vectors and/or host cell for use in medicine. The use in medicine in one preferred embodiment includes the use in the diagnosis, prevention and/or treatment of a proliferative disease, such as a malignant or benign tumor disease.

Thus also provided by the present invention is a method for treating a subject suffering from a tumor or tumor disease comprising the administration of the antigen recognizing constructs, nucleic acids, vectors and/or host cell as disclosed by the present invention. Preferably the subject is a subject in need of such a treatment. The subject in preferred embodiments is a mammalian subject, preferably a human patient, suffering from a tumor or tumor disease.

In one preferred aspect of the invention the tumor or tumor disease is a disease characterized by the expression of a MAGE antigen as described herein above. Most preferably the tumor or tumor disease expresses the MAGE-A1 antigen, even more preferably wherein the tumor or tumor disease presents via HLA the MAGE-A1$_{278-286}$ epitope. Further preferred is that the tumor or tumor disease is characterized by the differential expression of the MAGE-A1 antigen compared to healthy tissue. The MAGE-A1 antigen may be expressed to a low extend in normal (non-cancerous) cells, whereas the antigen is significantly stronger expressed in the tumor cells.

Also, in one preferred aspect of the invention the expression of MAGE-A1 in the tumor is induced or enhanced by prior pharmacologic treatment, e.g. with 5-aza-2-deoxycitabine.

The term "tumor" or "tumor disease" in the context of the present invention denotes a disease selected from melanomas, hepatocellular carcinomas, intra- and extrahepatic cholangiocellular carcinomas, squamous cell carcinomas, adenocarcinomas as well as undifferentiated carcinomas of the head, neck, lung or esophagus, colorectal carcinomas, chondrosarcomas, osteosarcomas, medulloblastomas, neuroblastomas, non-squamous cell carcinomas of the head or neck, ovarian tumors, lymphomas, acute and chronic lymphocytic leukemias, acute and chronic myeloid leukemia, bladder carcinomas, prostate carcinomas, pancreatic adenocarcinomas, mammary carcinomas and gastric carcinomas. Preferred diseases to be treated by the products and/or methods of the invention include melanoma, non-small-cell lung cancer, pancreatic adenocarcinoma and cholangiocellular carcinoma.

One preferred medicinal use of the invention relates to immune therapy, preferably adoptive T cell therapy. The product and methods of the invention are particularly useful in the context of adoptive T cell therapy. The administration of the compounds of the invention can for example involve the infusion of T cells of the invention into said patient. Preferably such T cells are autologous T cells of the patient which were in vitro transduced with a nucleic acid or antigen recognizing constructs of the present invention.

The invention in one further aspect discloses a method for the manufacturing of a MAGE-A1 specific antigen recognizing construct (ARC) expressing cell line, comprising
a. Providing a suitable host cell,
b. Providing a genetic construct encoding for an ARC, wherein said ARC comprises a CDR3 having an amino acid sequence with at least 50%, 60%, 70%, 80%, 90%, 95%, 98%, 99% or 100% sequence identity to an amino acid sequence selected from SEQ ID Nos. 1 to 6,
c. Introducing into said suitable host cell said genetic construct,
d. Expressing said genetic construct by said suitable host cell.

The above method may in one preferred embodiment further comprise the step of including a cell surface presentation of said ARC.

Of course it is also preferred that context of this aspect of the invention said ARC is an ARC according to the inventive aspects as described herein above. In this respect it is also additionally or alternatively preferred that said ARC is of mammalian origin, preferably of human origin.

The preferred suitable host cell for use in the method of the invention is a mammalian, in particular a human cell, such as a human T-cell. T cells for use in the invention are described in detail herein above.

The ARC produced according to the method of the invention is in one embodiment a TCR. For example also included are TCRs with additional (functional) domains or a TCR provided with alternative domains, e.g. a TCR provided with a foreign transmembrane-domain as membrane anchor. A TCR produced in accordance with the present invention is for example an alpha/beta TCR, gamma/delta TCR or a single chain TCR (scTCR). Also, TCR forms which are included by the present invention are generally any TCR known in the art, specifically those described herein above.

Desirably, the transfection system for use in the method in accordance with the invention is a retroviral vector system. Such systems are well known to the skilled artisan.

Also comprised by the present invention is in one embodiment the additional method step of purification of the ARC from the cell and, optionally, the reconstitution of the translated ARC-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention for example a human or non-human T-cell, preferably a human TCR.

Thus also provided is a pharmaceutical composition, comprising any of the herein described products of the invention, specifically any proteins, nucleic acids or host cells. In a preferred embodiment the pharmaceutical composition is for immune therapy.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 1: shows the concept of adoptive T cell therapy

Figure 2:
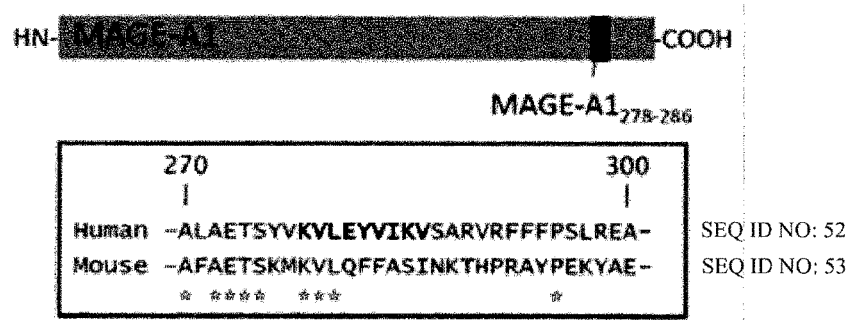

FIG. 2: shows MAGE-A1 and its epitope localization

Figure 3:
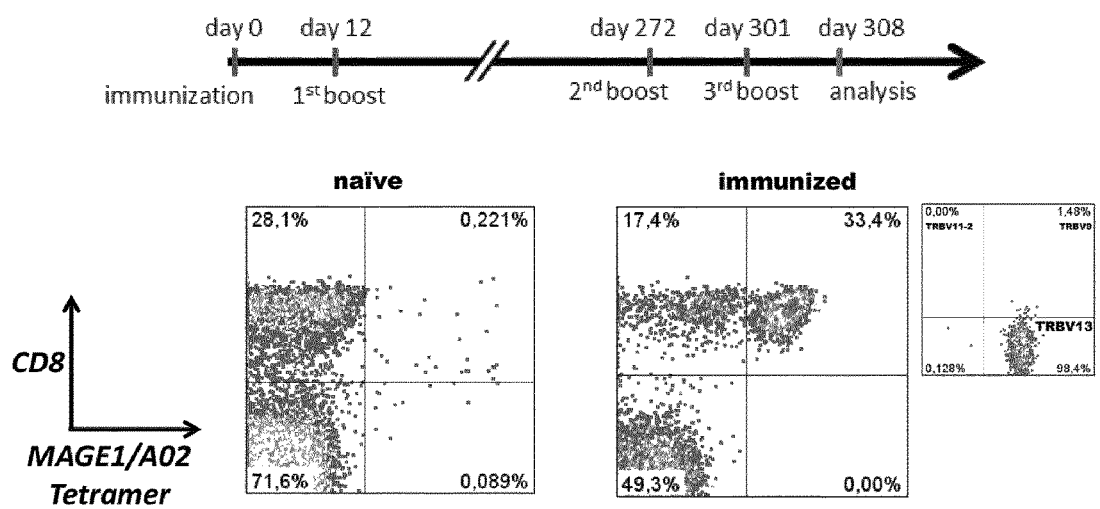

FIG. 3: shows the immune response against MAGE-A1 in ABabDII mice

FIG. 4: shows a schematic representation of the TCR vectors

Figure 5:
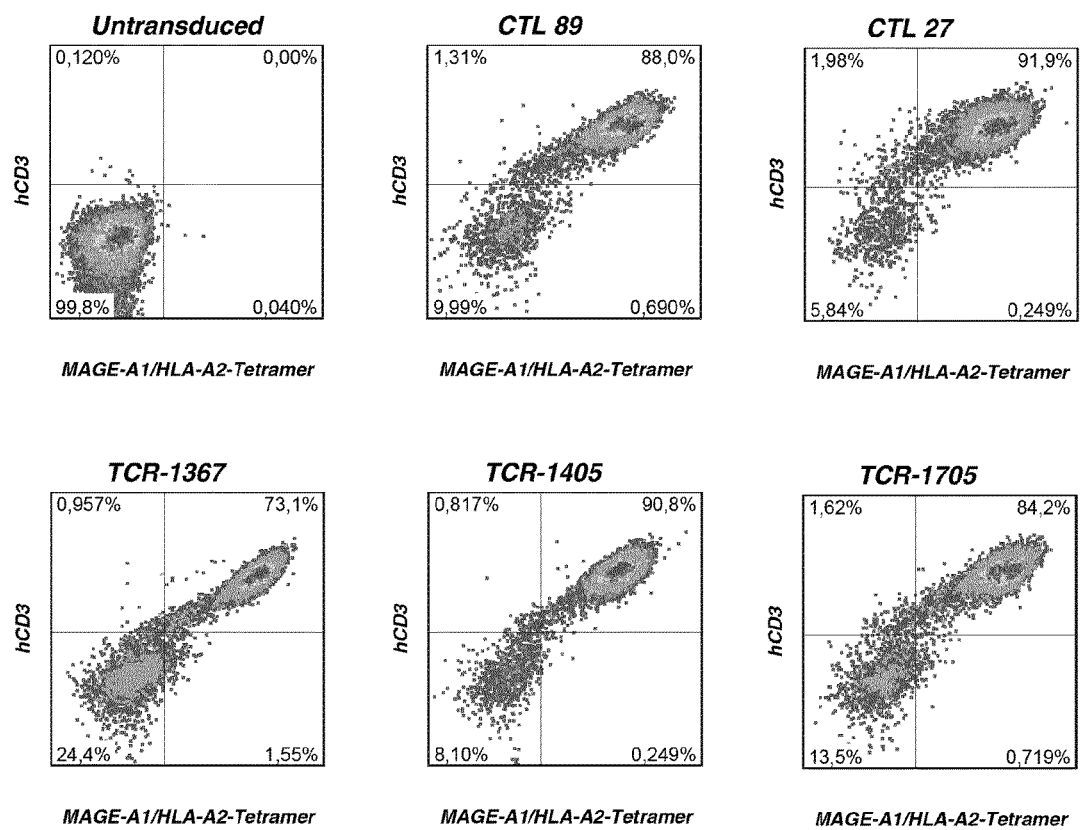

FIG. 5: shows FACS results of TCR transduced Jurkat 76 cells

Figure 6:
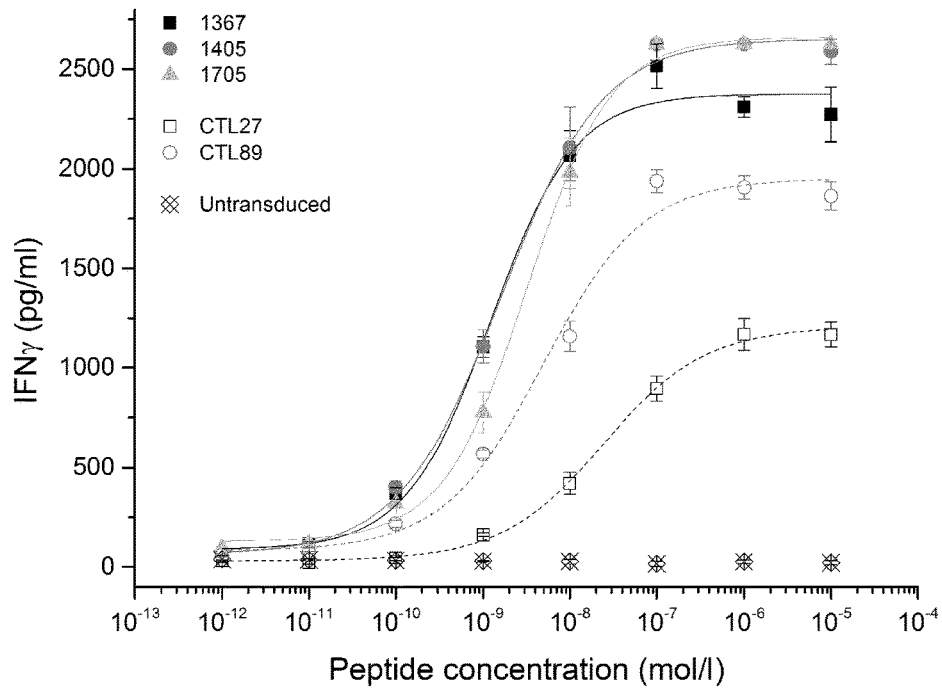

FIG. 6: shows the functional avidity of MAGE-A1 specific T cells

Figure 7:
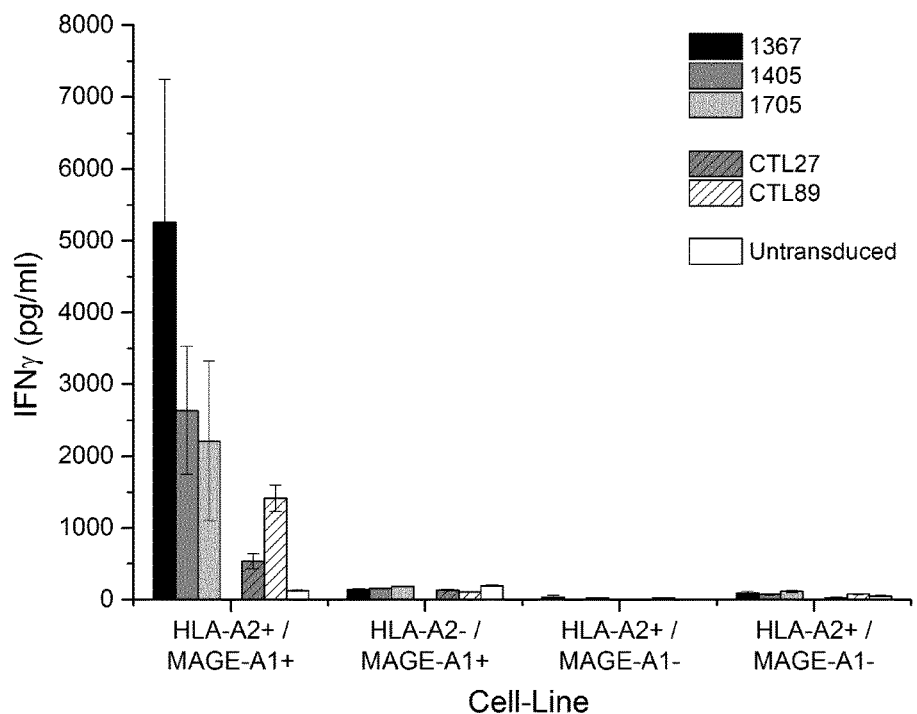

FIG. 7: shows the tumor cell recognition MAGE-A1 by T cells transduced with the MAGE-A1 specific TCRs of the invention.

Figure 8:
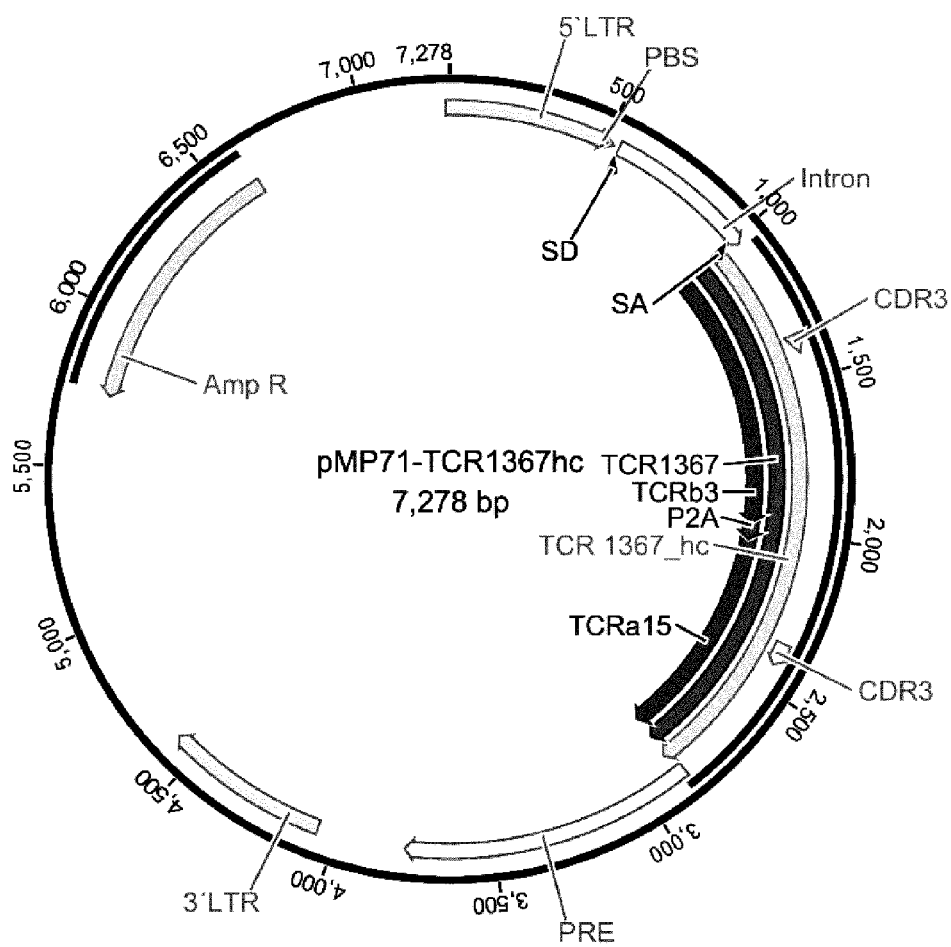

FIG. 8: Vector map of pMP71-TCR1367hc. The TCR encoding sequence is located between nucleotides 1041 and 2864 of SEQ ID No. 13. The TCR beta chain is located between nucleotides 1041 and 1970, the alpha chain between 2037 and 2864.

Figure 9:
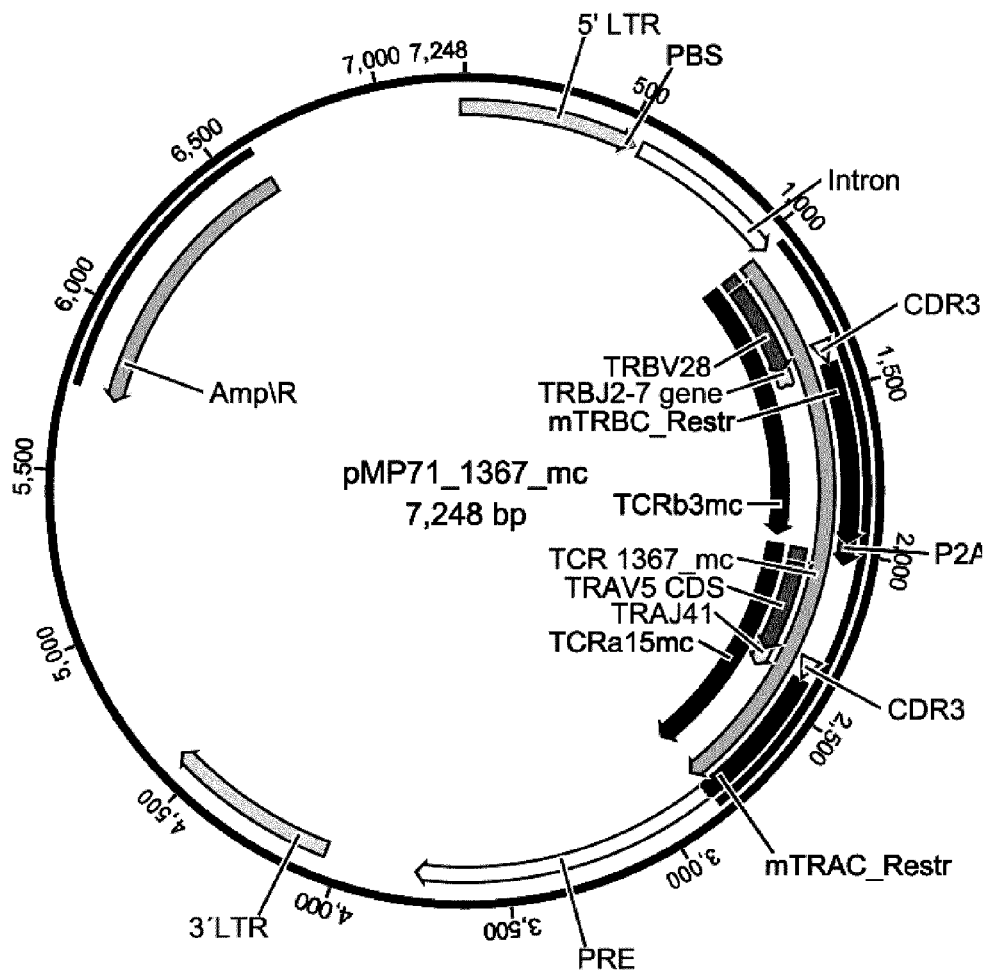

FIG. 9: Vector map of pMP71-TCR1367mc. The TCR encoding sequence is located between nucleotides 1041 and 2834 of SEQ ID No. 14. . The TCR beta chain is located between nucleotides 1041 and 1952, the alpha chain between 2019 and 2834.

Figure 10:
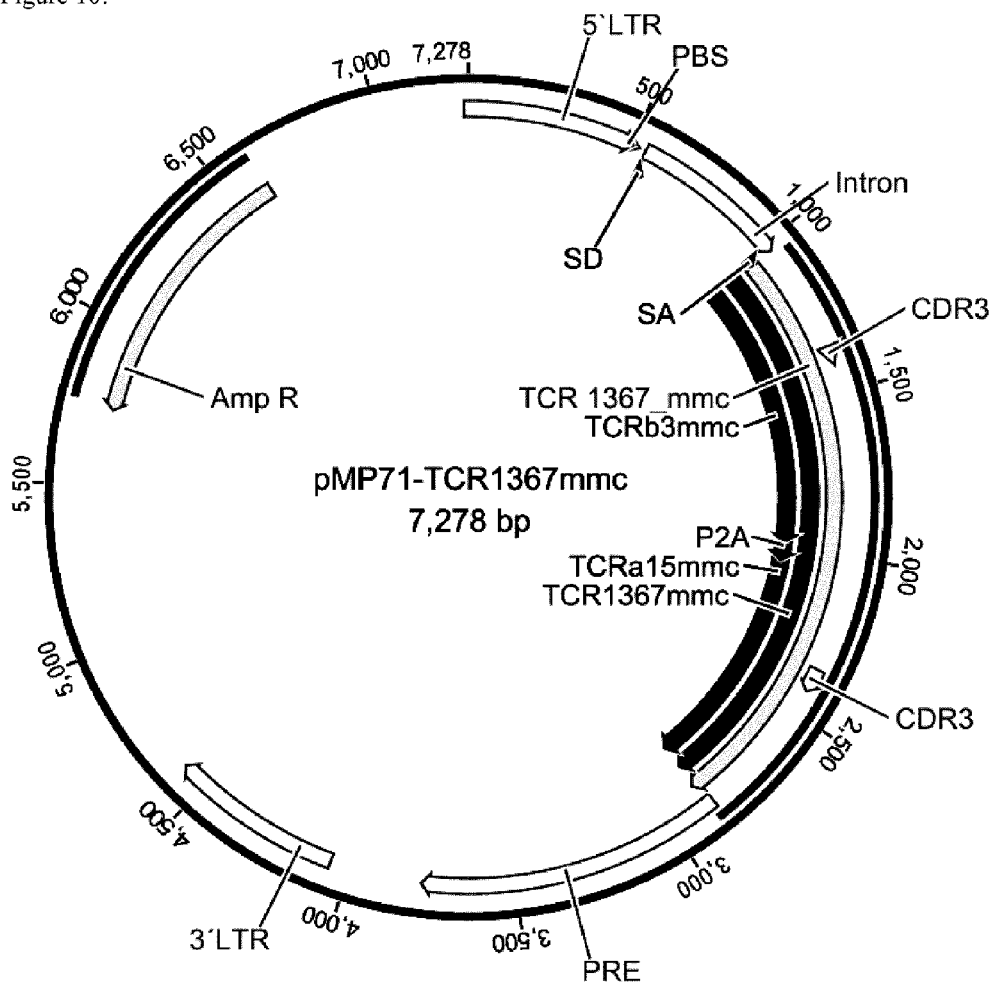

FIG. 10: Vector map of pMP71-TCR1367mmc. The TCR encoding sequence is located between nucleotides 1041 and 2864 of SEQ ID No. 15. The TCR beta chain is located between nucleotides 1041 and 1970, the alpha chain between 2037 and 2864.

Figure 11:
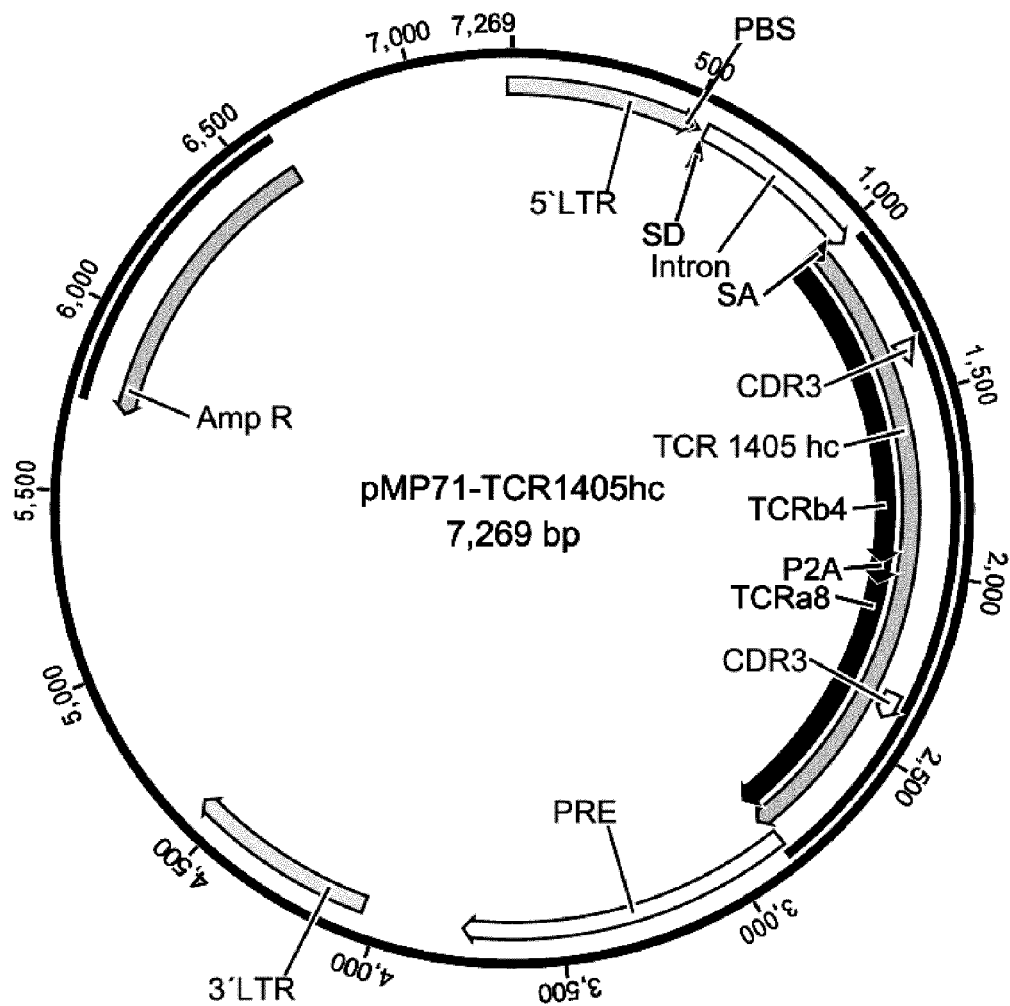

FIG. 11: Vector map of pMP71-TCR1405hc. The TCR encoding sequence is located between nucleotides 1041 and 2855 of SEQ ID No. 16. The TCR beta chain is located between nucleotides 1041 and 1967, the alpha chain between 2034 and 2855.

Figure 12:
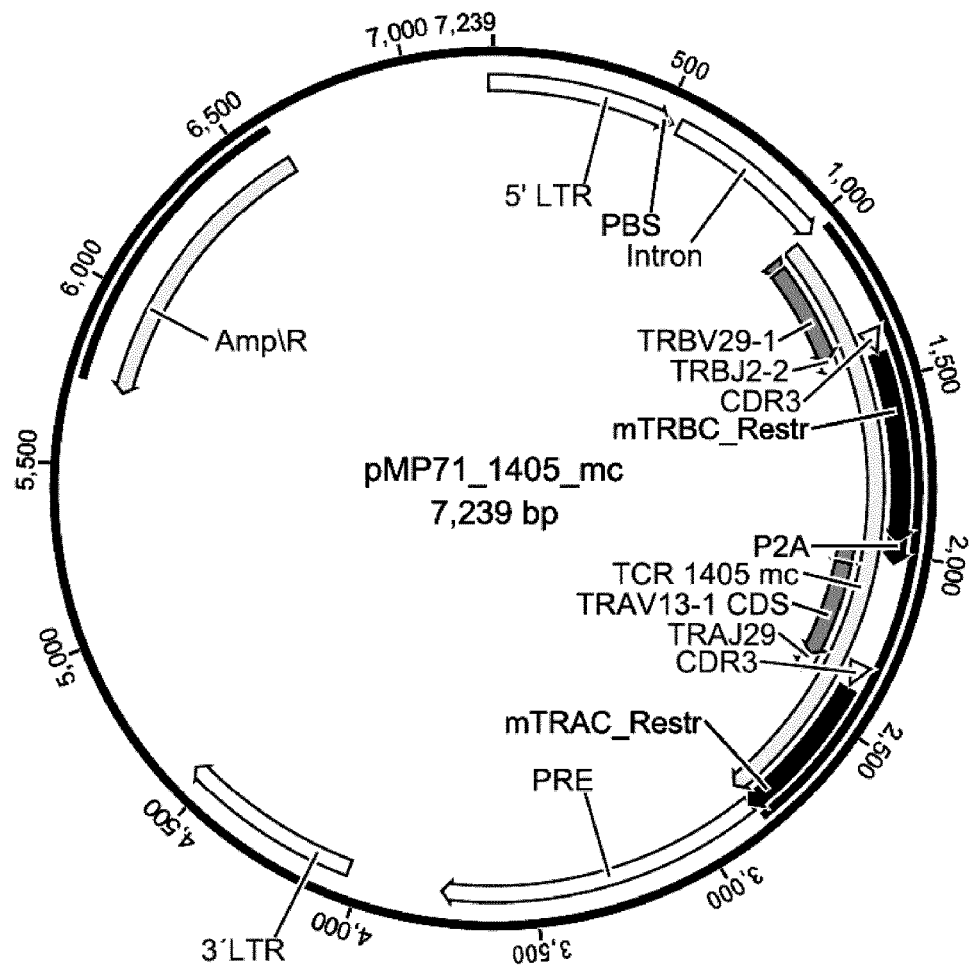

FIG. 12: Vector map of pMP71-TCR1405mc. The TCR encoding sequence is located between nucleotides 1041 and 2825 of SEQ ID No. 17. The TCR beta chain is located between nucleotides 1041 and 1949, the alpha chain between 2016 and 2825.

Figure 13:
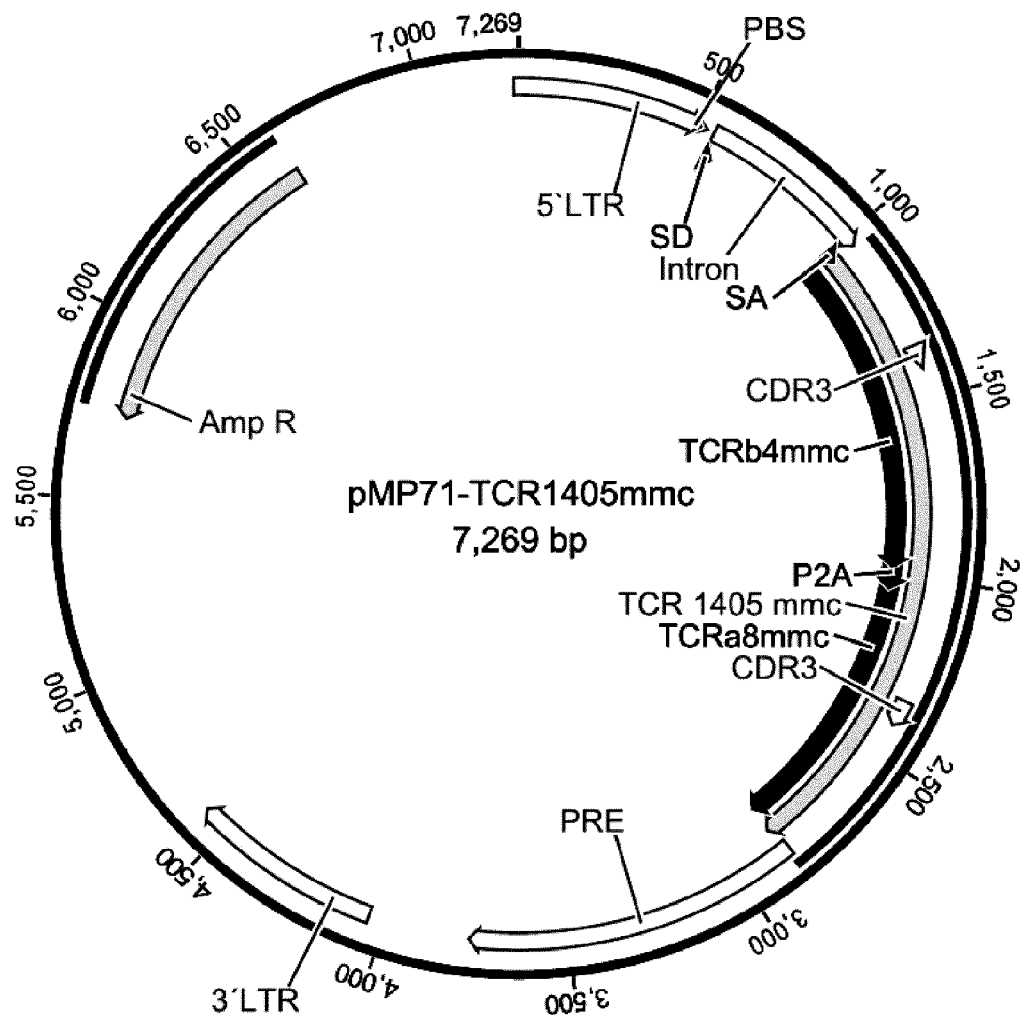

FIG. 13: Vector map of pMP71-TCR1405mmc. The TCR encoding sequence is located between nucleotides 1041 and 2854 of SEQ ID No. 18. The TCR beta chain is located between nucleotides 1041 and 1967, the alpha chain between 2034 and 2854.

Figure 14:
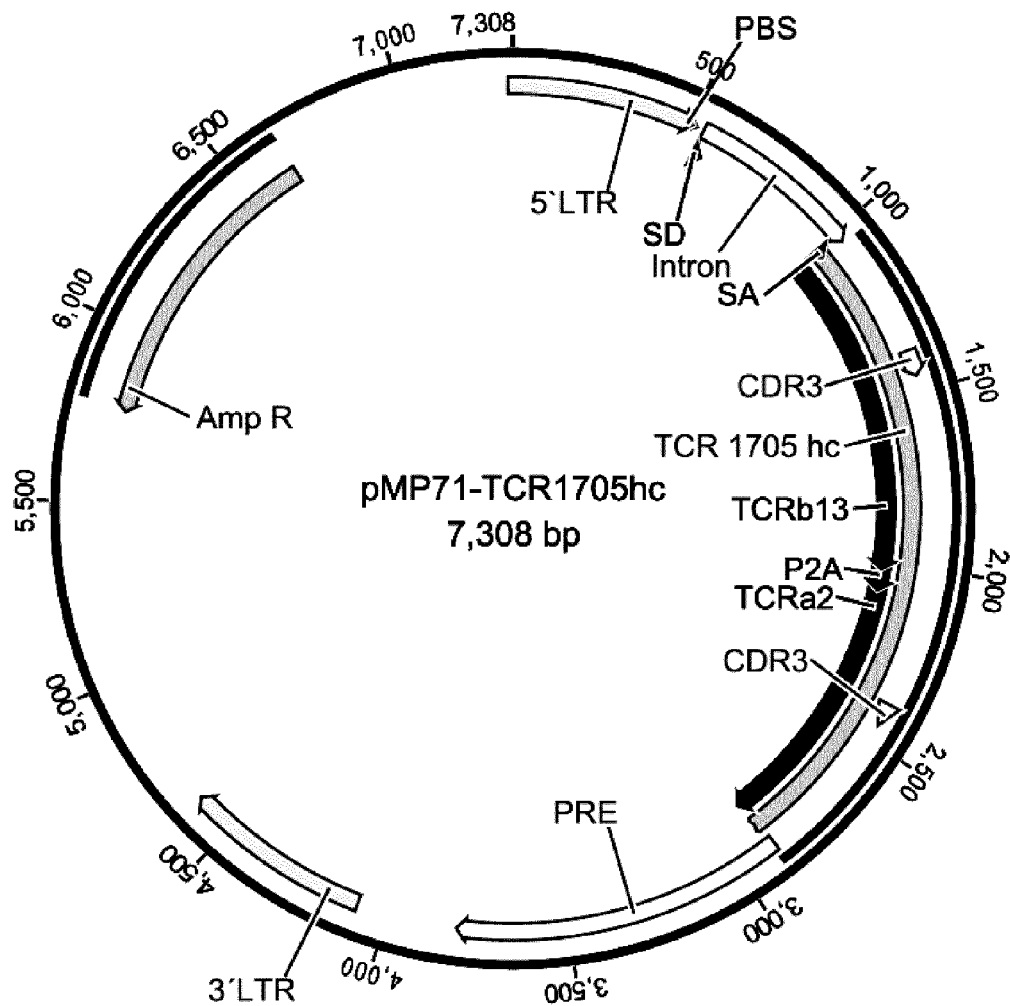

FIG. 14: Vector map of pMP71-TCR1705hc. The TCR encoding sequence is located between nucleotides 1041 and 2894 of SEQ ID No. 19. The TCR beta chain is located between nucleotides 1041 and 2006, the alpha chain between 2073 and 2894.

Figure 15:
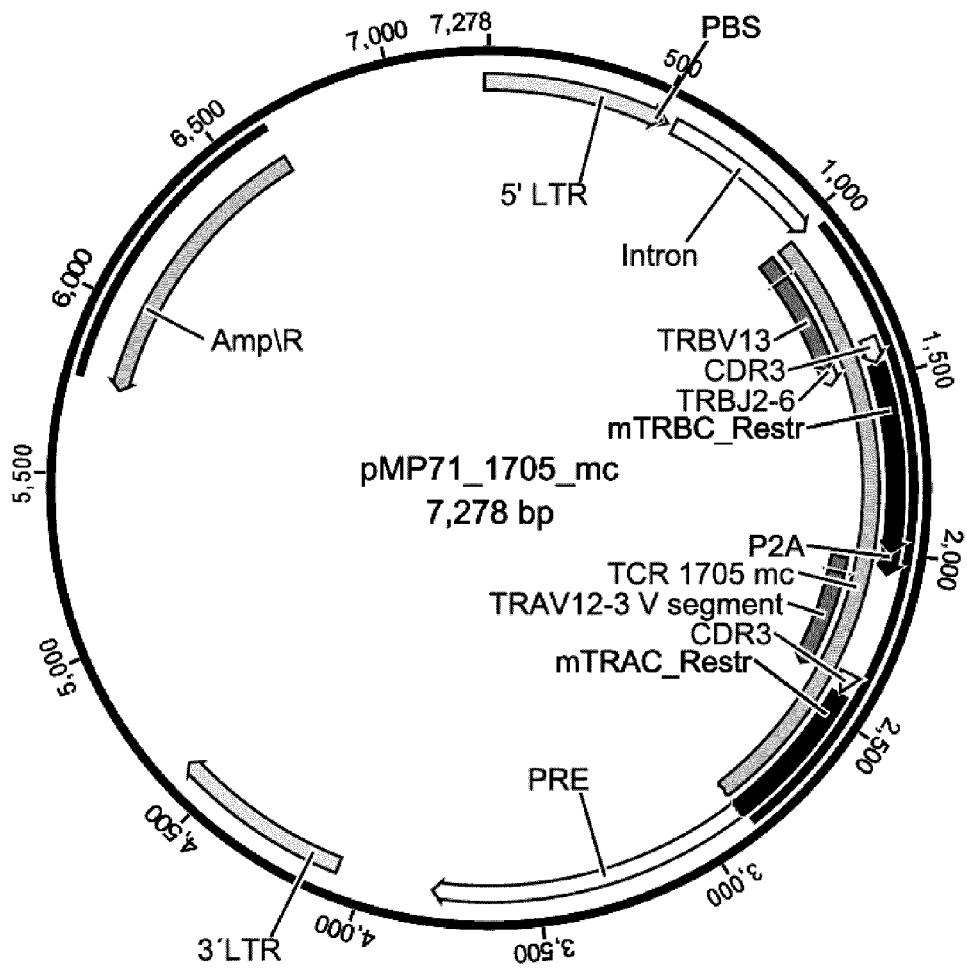

FIG. 15: Vector map of pMP71-TCR1705mc. The TCR encoding sequence is located between nucleotides 1041 and 2864 of SEQ ID No. 20. The TCR beta chain is located between nucleotides 1041 and 1988, the alpha chain between 2055 and 2864.

Figure 16:
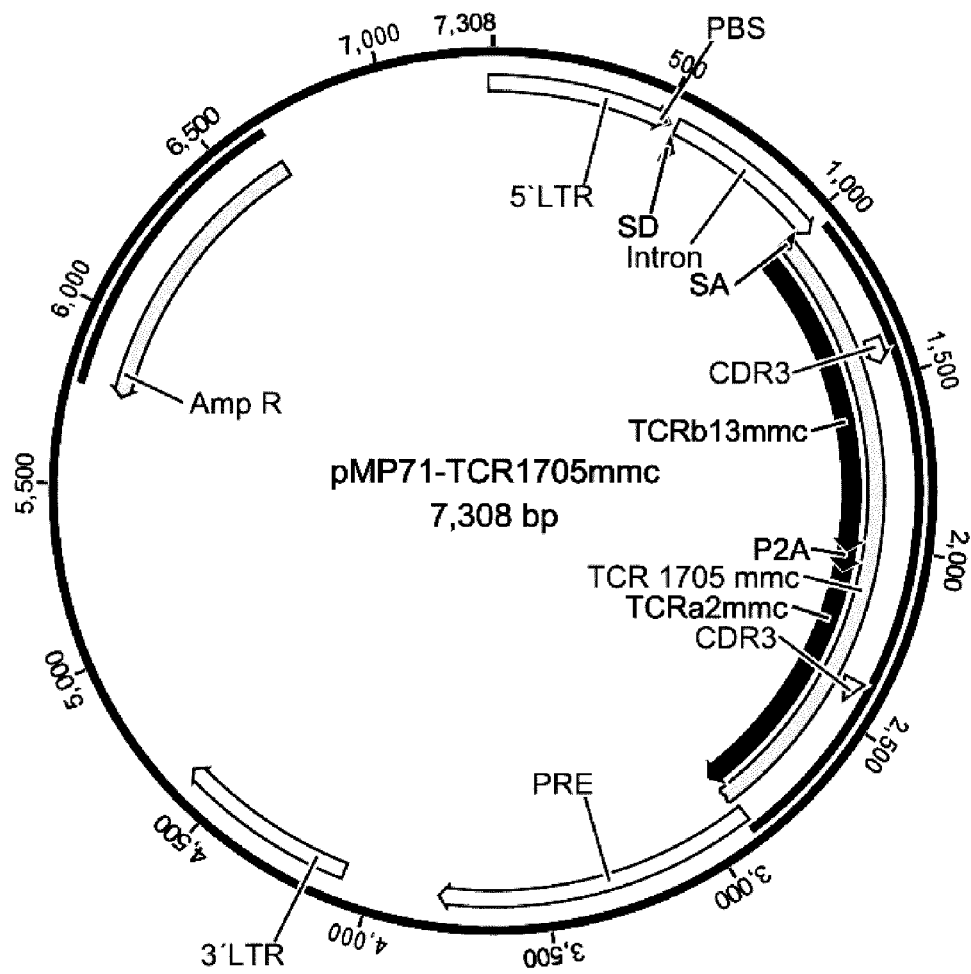

FIG. 16: Vector map of pMP71-TCR1705mmc. The TCR encoding sequence is located between nucleotides 1041 and 2894 of SEQ ID No. 21. The TCR beta chain is located between nucleotides 1041 and 2006, the alpha chain between 2073 and 2894.

Figure 17:
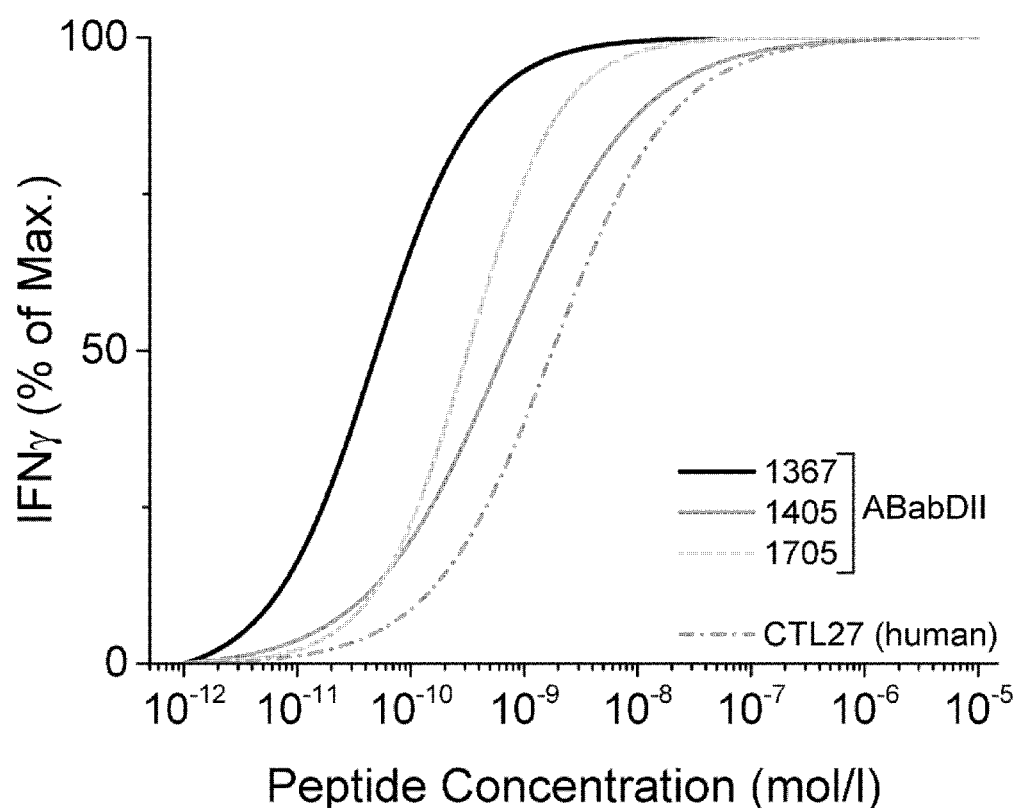

FIG. 17: T2 cells were incubated with increasing concentrations of MAGE-A1278 and cocultured with human T cells that had been transduced with different TCRs as indicated. After 12 hours, functional response was assessed by measuring IFNγ in the cultures.

Figure 18:
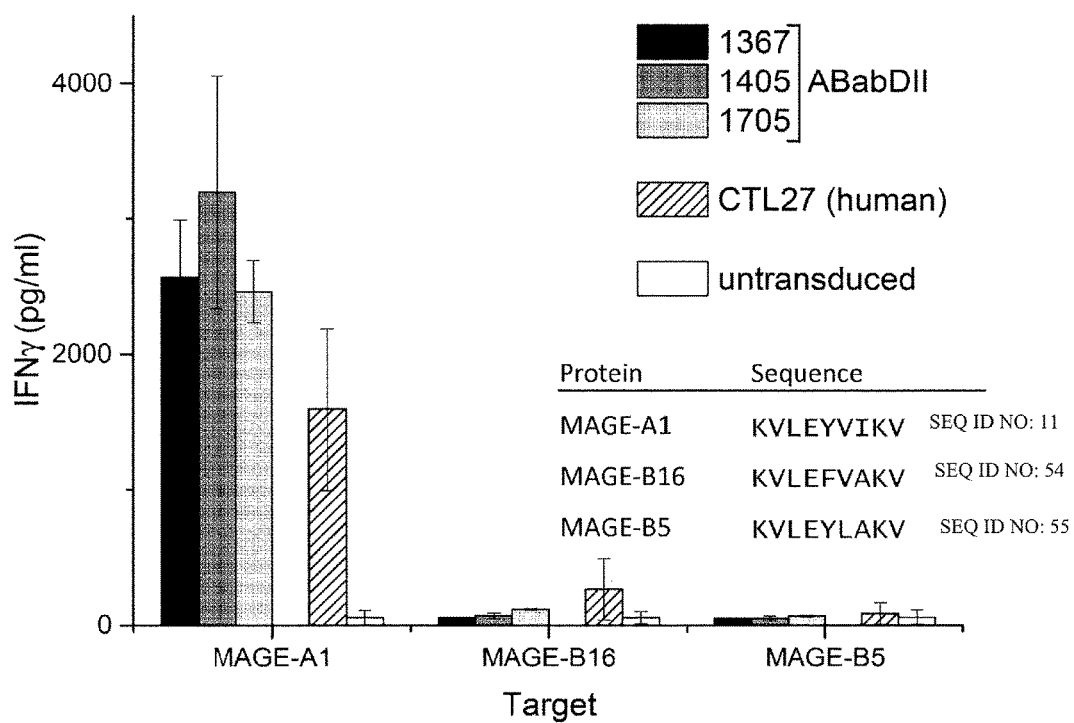

FIG. 18: T2 cells were loaded with 10-5 mol/l MAGE-A1278 (SEQ ID NO:11) or the 2 most similar epitopes in the human proteome (MAGE-B16 and MAGE-B5, SEQ ID NOs:54 and 55, respectively) differing in only 2 amino acids from MAGE-A1278 and co-cultured with TCR modified T cells. Functional response was assessed based on IFNγ production.

Figure 19:
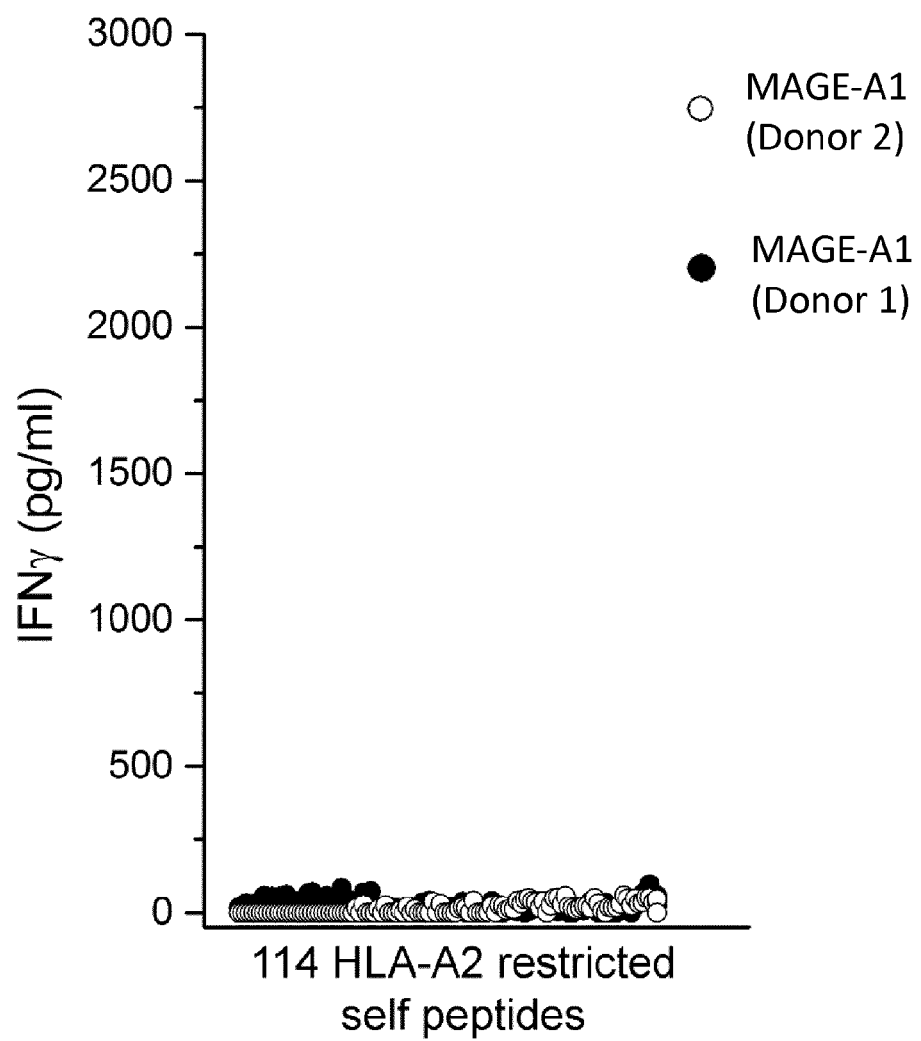

FIG. 19: T2 cells were loaded with one of 114 different HLA-A2 restricted self-peptides at a concentration of 10-5 mol/l and co-cultured with T cells from 2 different donors that were transduced with TCR 1367. The results of donor 1 are shown as black dots, the results of donor 2 by white dots.

SEQ ID No 1 to 6: show alpha and beta CDR3 sequences of the TCRs of the invention.

SEQ ID No 7 to 10: show alpha and beta chain CDR3 sequences of healthy humans.

SEQ ID No 11 to 12: show the epitope sequences of human (11) and mouse (12) MAGE-A1.

SEQ ID No 13 to 21: show the vector nucleotide sequences of FIGS. 8 to 16.

SEQ ID No 22 to 39: show the complete amino acid sequences of the alpha and beta chains of the TCRs of the invention SEQ ID No 40 to 51: show alpha and beta CDR1 and CDR2 sequences of Vα and Vβ genes.

EXAMPLES

Example 1

Generation of T-cells with a MAGE Epitope using the ABabDII Mouse

FIG. 2 shows the location of the HLA-A2 restricted epitope MAGE-A1$_{278-286}$ is shown in relation to the full-length MAGE-A1 protein (top). The human MAGE-A1$_{278-286}$ epitope is sufficiently different from its mouse homologue to prevent tolerance against human MAGE-A1$_{278-286}$ in ABabDII mice (bottom).

MAGE-A1 is expressed in a variety of human tumors, whereas its expression on normal human tissue is believed to be restricted to the testes. Therefore, specific targeting of MAGE-A1 expressing cells should limit toxicity to a minimum.

ABabDII mice were immunized with a 30mer peptide encompassing the nonamer MAGE-A1$_{278-286}$ plus CpG in incomplete Freund's adjuvant. Boosts were performed with the nonamer MAGE-A1$_{l278-286}$ plus CpG in incomplete Freund's adjuvant. On the day of analysis, blood was taken and stained with a MAGE-A1/HLA-A2 specific tetramer and with antibodies for certain TRBV chains (IMGT nomenclature). After several boosts a monoclonal population of MAGE-A1 specific T cells is detectable in the blood of ABabDII mice. FIG. 3 shows the immune response of the immunized animal and the immunization scheme. A significant shift in FACS analysis of the immunized cells is observed with the tetramer staining indicating that MAGE specific T cells were generated.

Example 2

Isolation and Characterization of T Cell Receptors

The cDNA from MAGE-A1 specific T cell clones as generated in Example 1 was amplified by 5'-RACE and sequenced.

The table 1 shows the amino acid sequences of complementary determining region 3 (CDR3) of the alpha and beta chains for three different TCRs from ABabDII mice and two TCRs obtained from healthy humans (Ottaviani, S., Zhang, Y., Boon, T., & van der Bruggen, P. (2005). *A MAGE-1 antigenic peptide recognized by human cytolytic T lymphocytes on HLA-A2 tumor cells. Cancer Immunology, Immunotherapy: CII,* 54(12), 1214-1220.).

TABLE 1

Amino acid sequences of the CDR3-regions for three different MAGE-A1 specific TCRs.

| TCR | alpha chain CDR3 | beta chain CDR3 |
| --- | --- | --- |
| 1367 | TRAV5-CAESIGSNSGYALNF-TRAJ41 (SEQ ID No. 1) | TRBV28-CASRGLAGYEQYF-TRBJ2-7(SEQ ID No. 4) |
| 1405 | TRAV13-1-CAARPNSGNTPLVF-TRAJ29 (SEQ ID No. 2) | TRBV29-1-CSVEQDTNTGELFF-TRBJ2-2(SEQ ID No. 5) |
| 1705 | TRAV12-3-CAMSDTGNQFYF-TRAJ49(SEQ ID No. 3) | TRBV13-CASSFRGGGANVLTF-TRBJ2-6(SEQ ID No. 6) |
| CTL27* | TRAV5-CAESYNARLMF-TRAJ31 (SEQ ID No. 7) | TRBV20-CSAREPGQGPYEQYFG-TRBJ7 (SEQ ID No. 9) |
| CTL89* | TRAV5-CAGSGGGTDKLIF-TRAJ34 (SEQ ID No. 8) | TRBV12-CASLSGVYTFG-TRBJ1-2 (SEQ ID No. 10) |

*human repertoire see: Ottaviani et al. (2005). Cancer Immunology, Immunotherapy, 54(12), 1214-1220

The isolated TCR which comprise the above CDR3 sequences were then cloned. The retroviral vector MP71 is used for transduction of primary human peripheral blood lymphocytes (hPBLs). The alpha and beta genes of each TCR are linked with a P2A element which is cut by a cellular protease during translation of the transduced TCR ensuring equimolar expression of both chains (FIG. 4).

All genes are codon optimized for optimal expression. In order to further optimize expression in hPBLs additional modifications were introduced into the wild-type TCR constant regions. Complete (A) and minimal (B) murinization of the constant regions of the TCR chains usually result in higher expression levels in hPBLs than the unmodified human constant region (C).

Then hCD8+ Jurkat 76 cells were transduced with different TCRs derived from ABabDII mice and human volunteers. Transduced cells stain positive for CD3. All transduced cells specifically bind the MAGE-A1/HLA-A2 tetramer (FIG. 5).

Surprisingly, the TCRs of the present invention provide an unusually high avidity compared to the TCRs of the state of the art. hPBLs were transduced with different MAGE-A1 specific TCRs. The transduced PBLs were then incubated with T2 cells, which had been pulsed with different concentrations of MAGE-A1$_{278-286}$ peptide. After overnight incubation IFNγ-production was measured by ELISA.

In response to stimulation with peptide pulsed T2 cells the TCRs from ABabDII mice (FIG. 6, closed circles) show a response at lower peptide concentrations and a higher amount of IFNγ-production than the TCRs derived from the tolerant human system (FIG. 6, open circles).

This was further confirmed by testing tumor cell recognition using the TCRs of the invention (FIG. 7). Transduced hBLs were incubated with different tumor cell lines. After overnight incubation IFNγ-production was measured by ELISA. The transduced hPBLs specifically recognize MAGE-A1 in the context of HLA-A2 restricted presentation. PBLs transduced with TCRs from ABabDII mice (full bars) produce higher amounts of IFNγ than those transduced with TCRs from the human repertoire (shaded bars) when incubated with MAGE-A1 expressing tumor cell lines.

Example 3

Sensitivity and Specificity of the TCR of the Invention

MAGE-A1$_{278}$ antigen was presented on T2 cells. The antigen presenting T2 cells were co-cultured with T-cells expressing the TCR of the invention or a control TCR (CTL27). As shown in FIG. 17 T cells modified with inventive TCRs from ABabDII mice (solid lines) respond to lower amounts of antigen than those modified with a human TCR (dash-dotted line). (One representative example out of 3 independent experiments is shown). These results indicate the surprisingly improved (by at least one order of magnitude) sensitivity of the TCR of the invention compared to state of the art TCR.

In order to test the specificity of the TCR of the invention over closely related MAGE antigenic epitopes, the TCRs were brought into contact with the MAGE antigens KVLEFVAKV (MAGE-B16) (SEQ ID NO:54) and KVLEYLAKV (MAGE-B5) (SEQ ID NO:55). The antigens were presented by T2 cells which were then co-cultured with T-cells expressing the TCR of the invention and a control. Interferon-γ release was measured. As can be seen from FIG. 18, the TCR of the invention significantly recognized the MAGE-A1$_{278}$ antigen and not the varients of the epitope. The specificity was much better compared to the control TCR.

The high specificity of the TCR of the invention was confirmed in an experiment testing 144 human HLA-A2 restricted self-antigens. FIG. 19 shows that donor T cells transfected with TCR 1367 specifically detected MAGE-A1 and not any other tested self-antigen, demonstrating the surprisingly high degree of specificity of the TCR of the invention.

Furthermore $10^6$ murine MAGE-A1 expressing fibrosarcoma cells were injected into immunodeficient mice and grown to a clinically relevant size of approximately 500 mm$^3$ tumor volume. To treat the tumors $10^6$ MAGE-A1 specific T cells bearing the either one of 2 TCRs from ABabDII mice (1367, 1405) or a human TCR (CTL27) were injected. In the control group, $10^6$ T cells bearing an irrelevant TCR were injected.

Treatment response was assessed 14 days after T-cell injection based on tumor volume. The results are provided in table 2 below. In the groups treated with ABabDII TCRs 100% and 67% of the animals responded to treatment. On the contrary, none of the animals treated with T cells transduced with a human TCR or an irrelevant TCR responded.

TABLE 2

| Treatment group | Response rate |
| --- | --- |
| 1367 | 5/5 (100%) |
| 1405 | 4/6 (67%) |
| CTL27 (human) | 0/6 (0%) |
| Irrelevant TCR | 0/3 (0%) |

The invention claimed is:

1. A T cell receptor (TCR), or derivative or fragment thereof, comprising:
   a) an alpha chain comprising CDR sequences comprising amino acid sequences of SEQ ID NO: 40, 41, and 1; and a beta chain comprising CDR sequences comprising amino acid sequences of SEQ ID NO: 46, 47, and 4; or
   b) an alpha chain comprising CDR sequences comprising amino acid sequences of SEQ ID NO: 42, 43, and 2; and a beta chain comprising CDR sequences comprising amino acid sequences of SEQ ID NO: 48, 49, and 5; or
   c) an alpha chain comprising CDR sequences comprising amino acid sequences of SEQ ID NO: 44, 45, and 3; and a beta chain comprising CDR sequences comprising amino acid sequences of SEQ ID NO: 50, 51, and 6.

2. The TCR, or derivative or fragment thereof, according to claim 1, wherein said TCR binds specifically to the MAGE-A1 antigen.

3. The TCR, or derivative or fragment thereof, according to claim 1, wherein said TCR induces an immune response.

4. The TCR, or derivative or fragment thereof, according to claim 3, wherein the immune response is characterized by an increase in interferon (IFN) γ levels.

5. The TCR, or derivative or fragment thereof, according to claim 1, wherein said TCR is in the form of an αβ heterodimer.

6. The TCR, or derivative or fragment thereof, according to claim 1, wherein said TCR is in a single chain format comprising said alpha chain and said beta chain.

7. The TCR, or derivative or fragment thereof, according to claim 6, wherein said TCR is fused to a human cytokine.

8. The TCR, or derivative or fragment thereof, according to claim 7, wherein said human cytokine is IL-2, IL-7 or IL-15.

* * * * *